(12) United States Patent
Soule

(10) Patent No.: US 11,446,277 B2
(45) Date of Patent: Sep. 20, 2022

(54) PENETRATING PAIN RELIEF CREAM

(71) Applicant: Felice Soule, West Hollywood, CA (US)

(72) Inventor: Felice Soule, West Hollywood, CA (US)

( * ) Notice: Subject to any disclaimer, the term of this patent is extended or adjusted under 35 U.S.C. 154(b) by 127 days.

(21) Appl. No.: 16/945,053

(22) Filed: Jul. 31, 2020

(65) Prior Publication Data
US 2021/0052542 A1 Feb. 25, 2021

Related U.S. Application Data

(60) Provisional application No. 62/881,727, filed on Aug. 1, 2019.

(51) Int. Cl.
| | | |
|---|---|---|
| *A61K 31/352* | (2006.01) | |
| *A61K 47/10* | (2017.01) | |
| *A61K 47/34* | (2017.01) | |
| *A61K 47/46* | (2006.01) | |
| *A61K 47/36* | (2006.01) | |
| *A61K 47/14* | (2017.01) | |
| *A61P 29/00* | (2006.01) | |
| *A61K 47/24* | (2006.01) | |
| *A61K 31/05* | (2006.01) | |
| *A61K 31/198* | (2006.01) | |
| *A61K 9/06* | (2006.01) | |
| *A61K 9/00* | (2006.01) | |
| *A61K 47/26* | (2006.01) | |

(52) U.S. Cl.
CPC .......... *A61K 31/352* (2013.01); *A61K 9/0014* (2013.01); *A61K 9/06* (2013.01); *A61K 31/05* (2013.01); *A61K 31/198* (2013.01); *A61K 47/10* (2013.01); *A61K 47/14* (2013.01); *A61K 47/24* (2013.01); *A61K 47/26* (2013.01); *A61K 47/34* (2013.01); *A61K 47/36* (2013.01); *A61K 47/46* (2013.01); *A61P 29/00* (2018.01)

(58) Field of Classification Search
None
See application file for complete search history.

*Primary Examiner* — Katherine Peebles
(74) *Attorney, Agent, or Firm* — Lathrop GPM LLP; Gordon Moriarty

(57) ABSTRACT

Provided herein are topical compositions, and their use in methods of treating pain and related disorders.

9 Claims, No Drawings

PENETRATING PAIN RELIEF CREAM

RELATED APPLICATION

This application claims the benefit of U.S. Provisional Patent Application No. 62/881,727, filed Aug. 1, 2019, the disclosure of which is incorporated by reference herein in its entirety.

BACKGROUND

Pain management is a challenge for health care professionals, as treatments using analgesic drugs are not always effective and may result in other health complications from long term use. Recent studies have supported the use of topical cannabinoid compositions as a safe alternative for pain relief. However, to be effective, the active ingredients of the composition must be able to penetrate the highly keratinized stratum corneum outside layer of the epidermis.

SUMMARY

The present disclosure is directed toward topical compositions for use in the treatment of PMS, neuropathy, arthritis, and pain. In an aspect, provided herein are topical compositions comprising:
  propanediol;
  dimethicone;
  glycerin;
  caprylic/capric triglycerides;
  *Olea europaea* fruit oil;
  biosaccharide gum-1;
  dimethyl isosorbide;
  ethoxydiglycol;
  polysorbate 20;
  a mixture consisting essentially of sodium acrylate/sodium acryloyl dimethyl taurate copolymer, cetyl alcohol, glycol stearate, and caprylic/capric triglycerides;
  a mixture consisting essentially of isopropyl pamitate, lecithin, water, and *Swertia chirata* extract;
  a mixture consisting essentially of propanediol and lecithin;
  a mixture consisting essentially of capryl glycol and ethylhexylglycerin;
  a mixture consisting essentially of water, glycerin, PEG-8, PEG-8/SMDI copolymer, palmitoyl myristyl stearate, and polyacrylate; and
  the balance of the composition comprises one or more components selected from the group consisting of cannabidiol, Δ9-tetrahydrocannabinol, cannabinol, cannabigerol, cannabidiolic acid, tetrahydrocannabinolic acid, cannabigerolic acid, cannabichromene, water, amni *visnaga* oil, *Petasites japonicus* root extract, arginine, bentofiamine, butylene glycol, cetyl hydroxyethylcellulose, rutin, palmitoyl tripeptide-1, palmitoyl tetrapeptide-7, *Phaseolus lunatus* seed extract, *cannabis* oil, *Capsicum frutescens* fruit extract, *chondrus* corpus extract, sodium hyaluronate, *Citrus paradisi* oil, *Corynanthe yohimbe* extract, butylene glycol, glycerin, carbomer, polysorbate 20, palmitoyl oligopeptide, glycolic acid, *Glycyrrhiza glabra* root extract, *Helianthis annuus* seed oil, *Rosmarinus officianalis* leaf extract, hexapeptide 30, hexapeptide 8, *Laminaria japonica* extract, *Melaluca alternifolia* leaf oil, *Mentha piperita* leaf oil, menthol, menthyl lactate, *Oenothera biennis* oil, *Persea gratissima* oil, *Physalis angulata* extract, capyrylic/capric triglycerides, *Pinus pinaster* bark extract, *Salix alba* bark extract, *Simmondsia chinensis* seed oil, *Tanacetum parthenium*, tocopherol, urea, *Valerian officinalis* extract, dextran, palmitoyl tripeptide-8, xanthan gum, *Euphausia superba* oil, and Cimisifuga *racemosa* extract.

In an embodiment, the composition comprises:
  about 4% by weight propanediol;
  about 5% by weight dimethicone;
  about 4% by weight glycerin;
  about 2% by weight caprylic/capric triglycerides;
  about 2% by weight *Olea europaea* fruit oil;
  about 3% by weight biosaccharide gum-1;
  about 2% by weight dimethyl isosorbide;
  about 2% by weight ethoxydiglycol;
  about 2% by weight polysorbate 20;
  about 5% by weight of a mixture consisting essentially of sodium acrylate/sodium acryloyl dimethyl taurate copolymer, cetyl alcohol, glycol stearate, and caprylic/capric triglycerides;
  about 2% by weight of a mixture consisting essentially of isopropyl pamitate, lecithin, water, and *Swertia chirata* extract;
  about 5% by weight of a mixture consisting essentially of propanediol and lecithin;
  about 1.2% by weight of a mixture consisting essentially of capryl glycol and ethylhexylglycerin;
  about 2% by weight of a mixture consisting essentially of water, glycerin, PEG-8, PEG-8/SMDI copolymer, palmitoyl myristyl stearate, and polyacrylate; and
  the balance of the composition comprises one or more components selected from the group consisting of cannabidiol, Δ9-tetrahydrocannabinol, cannabinol, cannabigerol, cannabidiolic acid, tetrahydrocannabinolic acid, cannabigerolic acid, cannabichromene, water, amni *visnaga* oil, *Petasites japonicus* root extract, arginine, bentofiamine, butylene glycol, cetyl hydroxyethylcellulose, rutin, palmitoyl tripeptide-1, palmitoyl tetrapeptide-7, *Phaseolus lunatus* seed extract, *cannabis* oil, *Capsicum frutescens* fruit extract, *chondrus* corpus extract, sodium hyaluronate, *Citrus paradisi* oil, *Corynanthe yohimbe* extract, butylene glycol, glycerin, carbomer, polysorbate 20, palmitoyl oligopeptide, glycolic acid, *Glycyrrhiza glabra* root extract, *Helianthis annuus* seed oil, *Rosmarinus officianalis* leaf extract, hexapeptide 30, hexapeptide 8, *Laminaria japonica* extract, *melaluca alternifolia* leaf oil, *Mentha piperita* leaf oil, menthol, menthyl lactate, *Oenothera biennis* oil, *Persea gratissima* oil, *Physalis angulata* extract, capyrylic/capric triglycerides, *Pinus pinaster* bark extract, *Salix alba* bark extract, *Simmondsia chinensis* seed oil, *Tanacetum parthenium*, tocopherol, urea, *Valerian officinalis* extract, dextran, palmitoyl tripeptide-8, xanthan gum, *Euphausia superba* oil, and Cimisifuga *racemosa* extract.

In another embodiment, the *cannabis* oil comprises from about 0.001% to about 10% by weight cannabidiol. In yet another embodiment, the *cannabis* oil comprises from about 0.001% to about 25% by weight Δ9-tetrahydrocannabinol.

In yet another embodiment, the balance of the mixture comprises:
  about 0.001% by weight amni *visnaga* oil;
  about 0.001% by weight of a mixture consisting essentially of *Petasites japonicus* root extract and water;
  about 0.001% by weight arginine;
  about 0.001% by weight bentofiamine;
  about 0.1% by weight of a mixture consisting essentially of butylene glycol, cetyl hydroxyethylcellulose, rutin, palmitoyl tripeptide-1, palmitoyl tetrapeptide-7, *Phaseolus lunatus* seed extract, and water;
  about 0.125% by weight of a component selected from the group consisting of *cannabis* oil, cannabidiol, Δ9-tetrahydrocannabinol, cannabinol, cannabigerol, cannabidiolic acid, tetrahydrocannabinolic acid, cannabigerolic acid, and cannabichromene;

about 0.001% by weight *Capsicum frutescens* fruit extract;

about 1% by weight of a mixture consisting essentially of *chondrus* corpus extract and sodium hyaluronate;

about 0.5% by weight *Citrus paradisi* oil;

about 0.1% by weight *Corynanthe yohimbe* extract;

about 0.1% by weight of a mixture consisting essentially of glycerin, water, butylene glycol, carbomer, polysorbate 20, palmitoyl oligopeptide, and palmitoyl tetrapeptide-7;

about 0.1% by weight glycolic acid;

about 0.1% by weight *Glycyrrhiza glabra* root extract;

about 0.2% by weight of a mixture consisting essentially of *Helianthis annuus* seed oil and *Rosmarinus officianalis* leaf extract;

about 0.001% by weight hexapeptide 30;

about 0.001% by weight hexapeptide 8;

about 1% by weight of *Laminaria japonica* extract;

about 0.001% by weight *Melaluca alternifolia* leaf oil;

about 0.1% by weight *Mentha piperita* leaf oil;

about 0.5% by weight of a mixture consisting essentially of menthol and menthyl lactate;

about 0.001% by weight *Oenothera biennis* oil;

about 0.125% by weight *Persea gratissima* oil;

about 0.5% by weight of a mixture consisting essentially of *Physalis angulata* extract and capyrylic/capric triglycerides;

about 0.1% by weight *Pinus pinaster* bark extract;

about 0.001% by weight *Salix alba* bark extract;

about 1% by weight *Simmondsia chinensis* seed oil;

about 0.1% by weight *Tanacetum parthenium;* about 0.1% by weight tocopherol;

about 1% by weight urea;

about 0.1% by weight *Valerian officinalis* extract;

about 0.3% by weight of a mixture consisting essentially of water, butylene glycol, dextran, and palmitoyl tripeptide-9;

about 0.25% by weight xanthan gum; and water.

In still another embodiment, the balance of the mixture comprises:

about 0.001% by weight amni *visnaga* oil;

about 0.001% by weight of a mixture consisting essentially of *Petasites japonicus* root extract and water;

about 0.001% by weight arginine;

about 0.001% by weight bentofiamine;

about 0.1% by weight of a mixture consisting essentially of butylene glycol, cetyl hydroxyethylcellulose, rutin, palmitoyl tripeptide-1, palmitoyl tetrapeptide-7, *Phaseolus lunatus* seed extract, and water;

about 0.125% by weight of a component selected from the group consisting of *cannabis* oil, cannabidiol, Δ9-tetrahydrocannabinol, cannabinol, cannabigerol, cannabidiolic acid, tetrahydrocannabinolic acid, cannabigerolic acid, and cannabichromene;

about 0.001% by weight *Capsicum frutescens* fruit extract;

about 1% by weight of a mixture consisting essentially of *chondrus* corpus extract and sodium hyaluronate;

about 0.4% by weight *Citrus paradisi* oil;

about 0.1% by weight of a mixture consisting essentially of glycerin, water, butylene glycol, carbomer, polysorbate 20, palmitoyl oligopeptide, and palmitoyl tetrapeptide-7;

about 0.1% by weight glycolic acid;

about 0.1% by weight *Glycyrrhiza glabra* root extract;

about 0.2% by weight of a mixture consisting essentially of *Helianthis annuus* seed oil and *Rosmarinus officianalis* leaf extract;

about 0.001% by weight hexapeptide 30;

about 0.001% by weight hexapeptide 8;

about 1% by weight of *Laminaria japonica* extract;

about 0.001% by weight *Melaluca alternifolia* leaf oil;

about 0.1% by weight *Mentha piperita* leaf oil;

about 0.5% by weight of a mixture consisting essentially of menthol and menthyl lactate;

about 0.001% by weight *Oenothera biennis* oil;

about 0.125% by weight *Persea gratissima* oil;

about 0.5% by weight of a mixture consisting essentially of *Physalis angulata* extract and capyrylic/capric triglycerides;

about 0.1% by weight *Pinus pinaster* bark extract;

about 0.001% by weight *Salix alba* bark extract;

about 1% by weight *Simmondsia chinensis* seed oil;

about 0.1% by weight *Tanacetum parthenium;* about 0.1% by weight tocopherol;

about 1% by weight urea;

about 0.1% by weight *Valerian officinalis* extract;

about 0.3% by weight of a mixture consisting essentially of water, butylene glycol, dextran, and palmitoyl tripeptide-9;

about 0.25% by weight xanthan gum; and water.

In another embodiment, the balance of the mixture comprises:

about 0.001% by weight amni *visnaga* oil;

about 0.001% by weight of a mixture consisting essentially of *Petasites japonicus* root extract and water;

about 0.001% by weight arginine;

about 0.001% by weight bentofiamine;

about 0.1% by weight of a mixture consisting essentially of butylene glycol, cetyl hydroxyethylcellulose, rutin, palmitoyl tripeptide-1, palmitoyl tetrapeptide-7, *Phaseolus lunatus* seed extract, and water;

about 0.125% by weight of a component selected from the group consisting of *cannabis* oil, cannabidiol, Δ9-tetrahydrocannabinol, cannabinol, cannabigerol, cannabidiolic acid, tetrahydrocannabinolic acid, cannabigerolic acid, and cannabichromene;

about 0.001% by weight *Capsicum frutescens* fruit extract;

about 1% by weight of a mixture consisting essentially of *chondrus* corpus extract and sodium hyaluronate;

about 0.4% by weight *Citrus paradisi* oil;

about 0.1% by weight of a mixture consisting essentially of glycerin, water, butylene glycol, carbomer, polysorbate 20, palmitoyl oligopeptide, and palmitoyl tetrapeptide-7;

about 0.1% by weight glycolic acid;

about 0.2% by weight of a mixture consisting essentially of *Helianthis annuus* seed oil and *Rosmarinus officianalis* leaf extract;

about 0.001% by weight hexapeptide 30;

about 0.001% by weight hexapeptide 8;

about 1% by weight of *Laminaria japonica* extract;

about 0.001% by weight *Melaluca alternifolia* leaf oil;

about 0.1% by weight *Mentha piperita* leaf oil;

about 0.5% by weight of a mixture consisting essentially of menthol and menthyl lactate;

about 0.001% by weight *Oenothera biennis* oil;

about 0.125% by weight *Persea gratissima* oil;

about 0.5% by weight of a mixture consisting essentially of *Physalis angulata* extract and capyrylic/capric triglycerides;

about 0.1% by weight *Pinus pinaster* bark extract;
about 0.001% by weight *Salix alba* bark extract;
about 1% by weight *Simmondsia chinensis* seed oil;
about 0.1% by weight *Tanacetum parthenium;*
about 0.1% by weight tocopherol;
about 1% by weight urea;
about 0.3% by weight of a mixture consisting essentially of water, butylene glycol, dextran, and palmitoyl tripeptide-9;
about 0.25% by weight xanthan gum; and
water.

In yet another embodiment, the balance of the mixture comprises:
about 0.001% by weight amni *visnaga* oil;
about 0.001% by weight of a mixture consisting essentially of *Petasites japonicus* root extract and water;
about 0.001% by weight arginine;
about 0.001% by weight bentofiamine;
about 0.1% by weight of a mixture consisting essentially of butylene glycol, cetyl hydroxyethylcellulose, rutin, palmitoyl tripeptide-1, palmitoyl tetrapeptide-7, *Phaseolus lunatus* seed extract, and water;
about 0.125% by weight of a component selected from the group consisting of *cannabis* oil, cannabidiol, Δ9-tetrahydrocannabinol, cannabinol, cannabigerol, cannabidiolic acid, tetrahydrocannabinolic acid, cannabigerolic acid, and cannabichromene;
about 0.001% by weight *Capsicum frutescens* fruit extract;
about 1% by weight of a mixture consisting essentially of *chondrus* corpus extract and sodium hyaluronate;
about 0.1% by weight *Cimicifuga racemosa* root extract;
about 0.4% by weight *Citrus paradisi* oil;
about 0.1% by weight *Corynanthe yohimbe* extract;
about 0.1% by weight *Euphausia superba* oil;
about 0.1% by weight of a mixture consisting essentially of glycerin, water, butylene glycol, carbomer, polysorbate 20, palmitoyl oligopeptide, and palmitoyl tetrapeptide-7;
about 0.1% by weight glycolic acid;
about 0.1% by weight *Glycyrrhiza glabra* root extract;
about 0.2% by weight of a mixture consisting essentially of *Helianthis annuus* seed oil and *Rosmarinus officianalis* leaf extract;
about 0.001% by weight hexapeptide 30;
about 0.001% by weight hexapeptide 8;
about 1% by weight of *Laminaria japonica* extract;
about 0.1% by weight *Mentha piperita* leaf oil;
about 0.001% by weight *Oenothera biennis* oil;
about 0.125% by weight *Persea gratissima* oil;
about 0.5% by weight of a mixture consisting essentially of *Physalis angulata* extract and capyrylic/capric triglycerides;
about 0.1% by weight *Pinus pinaster* bark extract;
about 0.001% by weight *Salix alba* bark extract;
about 1% by weight *Simmondsia chinensis* seed oil;
about 0.1% by weight *Tanacetum parthenium;*
about 0.1% by weight tocopherol;
about 1% by weight urea;
about 0.3% by weight of a mixture consisting essentially of water, butylene glycol, dextran, and palmitoyl tripeptide-9;
about 0.25% by weight xanthan gum; and
water.

In an embodiment, the composition forms nanolipids. In another embodiment, the nanolipids are 150 nm to 250 nm in size. In an embodiment, the composition forms liposomes. In another embodiment, the liposomes are 150 nm to 800 nm in size.

In an aspect, also provided herein are methods for treating premenstrual syndrome (PMS) in a subject in need thereof, comprising administering to the subject a therapeutically effective amount of the compositions disclosed herein. In an embodiment, the subject has a reduction in one or more symptoms of PMS. In another embodiment, the subject has a reduction in fatigue, change in appetite, irritability, difficulty in concentration, depression, changes in sleep, agitation, anxiety, tension, restlessness, moodiness, headaches, joint pain, cramps, bloating, edema, acne, constipation, nausea, inflammation, and/or breast tenderness.

In another aspect, provided herein are methods for treating neuropathy in a subject in need thereof, comprising administering to the subject a therapeutically effective amount of the compositions disclosed herein. In an embodiment, the neuropathy is nerve pain. In another embodiment, the subject has a reduction in one or more symptoms of neuropathy. In yet another embodiment, the subject has a reduction in pain, tingling, numbness, burning, and/or loss of sensation.

In yet another aspect, provided herein are methods for treating arthritis in a subject in need thereof, comprising administering to the subject a therapeutically effective amount of the compositions disclosed herein. In an embodiment, the arthritis is osteoarthritis, rheumatoid arthritis, psoriatic arthritis, or gout. In another embodiment, the subject has a reduction in one or more symptoms of arthritis. In yet another embodiment, the subject has a reduction in pain, swelling, stiffness, and/or an improvement in range of motion.

In still another aspect, provided herein are methods for treating pain in a subject in need thereof, comprising administering to the subject a therapeutically effective amount of the compositions disclosed herein. In an embodiment, the composition blocks afferent neuro synaptic pain signals.

In another aspect, provided herein are methods for improving skin quality in a subject in need thereof, comprising administering to the subject a therapeutically effective amount of the compositions disclosed herein. In an embodiment, the subject has an improvement in one or more aspects of skin quality. In another embodiment, the subject has a reduction in wrinkles, younger looking skin, improved cellular turnover, improved skin radiance, improvement in acne, brightened skin, improved skin hydration, and/or improved skin physiology.

In yet another aspect, provided herein are methods for treating skin discomfort in a subject in need thereof, comprising administering to the subject a therapeutically effective amount of the compositions disclosed herein. In an embodiment, the subject has a reduction in one or more symptoms of skin discomfort. In another embodiment, the subject has a reduction in itching and/or topical discomfort. In yet another embodiment, the itching and/or topical discomfort are from tattooing, laser treatment, or mild abrasions.

In still another aspect, provided herein are methods method for treating sprains, strains, muscle distress, and ligament distress in a subject in need thereof, comprising administering to the subject a therapeutically effective amount of the compositions disclosed herein.

In another aspect, provided herein are methods for treating anxiety in a subject in need thereof, comprising administering to the subject a therapeutically effective amount of the compositions disclosed herein.

In yet another aspect, provided herein are methods for inducing wound repair in a subject in need thereof, comprising administering to the subject a therapeutically effective amount of the compositions disclosed herein.

In still another aspect, provided herein are methods for treating headache in a subject in need thereof, comprising administering to the subject a therapeutically effective amount of the compositions disclosed herein.

In another aspect, provided herein are methods for treating hangover in a subject in need thereof, comprising administering to the subject a therapeutically effective amount of the compositions disclosed herein.

In yet another aspect, provided herein are methods for treating sinus pain in a subject in need thereof, comprising administering to the subject a therapeutically effective amount of the compositions disclosed herein.

In still another aspect, provided herein are methods for treating athlete's foot fungus in a subject in need thereof, comprising administering to the subject a therapeutically effective amount of the compositions disclosed herein.

In another aspect, provided herein are methods for treating sunburn in a subject in need thereof, comprising administering to the subject a therapeutically effective amount of the compositions disclosed herein.

In yet another aspect, provided herein are methods for treating insect bites in a subject in need thereof, comprising administering to the subject a therapeutically effective amount of the compositions disclosed herein.

In still another aspect, provided herein are methods for lightening the skin, comprising administering to the subject a therapeutically effective amount of the compositions disclosed herein.

In an embodiment, subject is human. In another embodiment, the composition is applied in as a cream. In another embodiment, the composition is applied topically.

DETAILED DESCRIPTION

The disclosure provides topical compositions that provide CBD and/or THC in a liposome based delivery system for the treatment of pain and related disorders. In some embodiments, related disorders include pre-menstrual syndrome, arthritis, migraines, neuropathy, plantar fascitis, chronic neck and joint pain and back pain.

Definitions

Listed below are definitions of various terms used herein. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art to which this disclosure belongs. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e., to at least one) of the grammatical object of the article. By way of example, "an element" means one element or more than one element. Furthermore, use of the term "including" as well as other forms, such as "include," "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±5%, from the specified value, as such variations are appropriate to perform the disclosed methods.

As used in the specification and in the claims, the term "comprising" may include the embodiments "consisting of" and "consisting essentially of." The terms "comprise(s)," "include(s)," "having," "has," "may," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated compounds, which allows the presence of only the named compounds, along with any pharmaceutically acceptable carriers, and excludes other compounds.

All ranges disclosed herein are inclusive of the recited endpoint and independently combinable (for example, the range of "from 50 mg to 500 mg" is inclusive of the endpoints, 50 mg and 500 mg, and all the intermediate values). The endpoints of the ranges and any values disclosed herein are not limited to the precise range or value; they are sufficiently imprecise to include values approximating these ranges and/or values.

As used herein, the term "treatment" or "treating," is defined as the application or administration of a therapeutic agent, i.e., a compound provided herein (alone or in combination with another pharmaceutical agent), to a human subject, or application or administration of a therapeutic agent to an isolated tissue or cell line from a human subject (e.g., for diagnosis or ex vivo applications), with the purpose to cure, heal, alleviate, relieve, alter, remedy, ameliorate, improve or affect the symptoms of a disease, disorder, syndrome, or condition. Such treatments can be specifically tailored or modified, based on knowledge obtained from the field of pharmacogenomics.

In certain embodiments, the compositions described herein reduce pain in a subject. Pain can be measured using any metric known in the art.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "use" includes any one or more of the following embodiments of the disclosure, respectively: the use in the treatment of pain the use for the manufacture of pharmaceutical compositions for use in the treatment of these diseases, e.g., in the manufacture of a medicament; methods of use of disclosed compositions in the treatment of these diseases; pharmaceutical preparations having the disclosed compositions for the treatment of these diseases; and disclosed compositions for use in the treatment of these diseases; as appropriate and expedient, if not stated otherwise.

As used herein, the terms "patient" and "subject" are used interchangeably and are intended to include an individual suffering from or afflicted with a disease, disorder, or condition. In some embodiments, the individual is a mammal, including, but not limited to, bovine, equine, feline, rabbit, canine, rodent, or primate. In some embodiments, the mammal is a primate. In some embodiments, the primate is a human. In some embodiments, the individual is human, including adults, children, and infants. In some embodiments, the individual is a non-mammal.

The term "individual" does not denote a particular age or sex.

When used with respect to methods of treatment/prevention and the use of the compounds and pharmaceutical compositions thereof described herein, an individual "in need thereof" may be an individual who has been diagnosed with or previously treated for the condition to be treated. With respect to prevention, the individual in need thereof may also be an individual who is at risk for a condition (e.g., a family history of the condition, life-style factors indicative of risk for the condition, etc.). Typically, when a step of administering a compound is disclosed herein, the disclosure further contemplates a step of identifying an individual or subject in need of the particular treatment to be administered or having the particular condition to be treated.

As used herein, the term "pharmaceutically acceptable" refers to a material, such as a carrier or diluent, which does not abrogate the biological activity or properties of the compound, and is relatively non-toxic, i.e., the material can be administered to an individual without causing undesirable biological effects or interacting in a deleterious manner with any of the components of the composition in which it is contained.

As used herein, the term "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "composition" or "pharmaceutical composition" refers to a mixture of at least one compound useful within the disclosure with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

As used herein, the term "pharmaceutically acceptable carrier" or "carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the disclosure within or to the human subject such that it can perform its intended function. Typically, such constructs are carried or transported from one organ, or portion of the body, to another organ, or portion of the body. Each carrier must be "acceptable" in the sense of being compatible with the other ingredients of the formulation, including the compound useful within the disclosure, and not injurious to the human subject. Some examples of materials that can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the disclosure, and are physiologically acceptable to the human subject. Supplementary active compounds can also be incorporated into the compositions. The "pharmaceutically acceptable carrier" or "carrier" can further include a pharmaceutically acceptable salt of the compound useful within the disclosure. Other additional ingredients that can be included in the pharmaceutical compositions used in the practice of the disclosure are known in the art and described, for example in Remington's Pharmaceutical Sciences (Genaro, Ed., Mack Publishing Co., 1985, Easton, Pa.), which is incorporated herein by reference.

The term "stabilizer," as used herein, refers to polymers capable of chemically inhibiting or preventing degradation. Stabilizers are added to formulations of compounds to improve chemical and physical stability of the compound.

As used herein, the term "adjuvant" may include, for example, preserving, wetting, suspending, sweetening, flavoring, perfuming, emulsifying, and dispensing agents. Prevention of the action of microorganisms is generally provided by various antibacterial and antifungal agents, such as, parabens, chlorobutanol, phenol, sorbic acid, and the like. Isotonic agents, such as sugars, sodium chloride, and the like, may also be included. Prolonged absorption of an injectable pharmaceutical form can be brought about by the use of agents delaying absorption, for example, aluminum monostearate and gelatin. The auxiliary agents also can include wetting agents, emulsifying agents, pH buffering agents, and antioxidants, such as, for example, citric acid, sorbitan monolaurate, triethanolamine oleate, butylated hydroxytoluene, and the like.

As used herein, the terms "effective amount," "pharmaceutically effective amount," and "therapeutically effective amount" refer to a nontoxic but sufficient amount of an agent to provide the desired biological result. That result may be reduction or alleviation of the signs, symptoms, or causes of a disease, or any other desired alteration of a biological system. An appropriate therapeutic amount in any individual case may be determined by one of ordinary skill in the art using routine experimentation.

As used herein, the term "weight percent" is meant to refer to the quantity by weight of a compound and/or component in a composition as the quantity by weight of a constituent component of the composition as a percentage of the weight of the total composition. The weight percent can also be calculated by multiplying the mass fraction by 100. The "mass fraction" is the ratio of one substance of a mass $m_1$ to the mass of the total composition $m_T$ such that weight percent=$(m_1/m_T)*100$.

"Aqueous buffer" refers to a water solution which resists change in hydronium ion and the hydroxide ion concentration (and consequent pH) upon addition of small amounts of acid or base, or upon dilution. Buffer solutions consist of a weak acid and its conjugate base (more common) or a weak base and its conjugate acid (less common). The buffer can be prepared by methods well known in the art with the appropriate buffering agents to give the desired pH value. Examples of the suitable buffering agents include hydrochloric acid, lactic acid, acetic acid, citric acid, malic acid, maleic acid, pyruvic acid, succinic acid, tris-hydroxymethylaminomethane, sodium hydroxide, sodium bicarbonate, phosphoric acid, sodium phosphate, and other biologically acceptable buffering agents. Aqueous buffers are readily available commercially and they can be used in preparation of the compositions of this disclosure without further treatment.

Unless otherwise indicated, the term "*Cannabis*" used herein refers to at least one of *Cannabis sativa* and *Cannabis indica*. Some of the materials which are produced by the *Cannabis* species have been shown to have pharmacologic activity.

Tetrahydrocannabinol, which is abbreviated herein as "THC" unless otherwise indicated, is the principal psychoactive constituent (or cannabinoid) of the *cannabis* plant. THC is also known as Δ9-tetrahydrocannabinol (Δ9-THC). THC was first isolated in 1964, and, in its pure form, it is a glassy solid when cold and becomes viscous and sticky if warmed. Pharmaceutical formulations that comprise THC, known by its INN dronabinol, are available by prescription in the U.S. and Canada under the brand name MARINOL. THC is an aromatic terpenoid, and it has a very low solubility in water but good solubility in most organic solvents, specifically lipids and alcohols. THC also exhibits high UV-B (280-315 nm) absorbance.

Cannabidiol (CBD) is one of at least 85 cannabinoids found in *cannabis*. It is a major constituent of the plant, second to THC, and represents up to 40% in its extracts. CBD has a wide scope of medical applications, including to epilepsy, multiple sclerosis spasms, anxiety disorders, schizophrenia, nausea, convulsion and inflammation, as well as inhibiting cancer cell growth. CBD may decrease the rate of THC clearance from the body, perhaps by interfering with the metabolism of THC in the liver. CBD has displayed sedative effects in animal tests, while other studies have found that CBD may increases alertness. CBD has been shown to reduce growth of aggressive human breast cancer cells in vitro, and to reduce their invasiveness.

CBD is an anti-oxidant, has anti-inflammatory activity and analgesic properties in animal studies. It has been shown to inhibit the growth of bacteria, and is thought to exhibit psychoactive properties that are distinct from THC that include anticonvulsant and anti-epileptic properties.

Other compounds found in *cannabis* with potential health benefits include β-sitosterol, tocopherols, and terpenes.

Hemp oil or hempseed oil is obtained by pressing hemp seeds. While most hemp oil is produced from strains of *Cannabis sativia* that produce low levels of THC, some formulations include hemp oil from strains of *Cannabis indica*.

Refined hempseed oil is clear and colorless, with little flavor and lacks natural vitamins and antioxidants. Refined hempseed oil is primarily used in body care products. Industrial hempseed oil is used in lubricants, paints, inks, fuel, and plastics. Hempseed oil has found some limited use in the production of soaps, shampoos and detergents. The oil is of high nutritional value because of its 3:1 ratio of omega-6 to omega-3 essential fatty acids, which matches the balance required by the human body.

Hempseed oil is generally manufactured from varieties of *Cannabis sativa* that do not contain significant amounts of THC, the psychoactive element present in the *cannabis* plant. There is no THC within the hempseed, although trace amounts of THC may be found in hempseed oil when plant matter adheres to the seed surface during manufacturing.

About 30-35% of the weight of hempseed is an edible oil that contains about 80% as essential fatty acids (EFAs); i.e., linoleic acid, omega-6 (LA, 55%), α-linolenic acid, omega-3 (ALA, 22%), in addition to μ-linolenic acid, omega-6 (GLA, 1-4%) and stearidonic acid, omega-3 (SDA, 0-2%).

As used herein, the term "*cannabis* oil" refers to a composition of cannabinoids and terpenes that are isolated from a *cannabis* plant. The term "*cannabis* oil," can include "hemp extract," "hemp oil," "marijuana oil" and "CBD oil". The *cannabis* oil can be obtained by any method known in the art. For example, the *cannabis* oil can be obtained by supercritical (or subcritical) $CO_2$ extraction, which uses carbon dioxide under high pressure and low temperatures to isolate, preserve and maintain the purity of hemp extract. In an embodiment, the *cannabis* oil is obtained from a supercritical $CO_2$ extraction. For example, supercritical $CO_2$ extraction may be performed as described in U.S. Pat. No. 8,895,078, which is incorporated herein by reference in its entirety. Alternatively, a solvent such as petroleum ether, ethanol, methanol, butanol, acetone, dry ice, or olive oil can be used, at room temperature (ambient temperature) with stirring, by passive extraction, heated to a temperature above room temperature, or under reflux, as known in the art to provide the *cannabis* oil. In another embodiment, *cannabis* oil from a butanol extraction is employed as starting material for methods disclosed herein.

As used herein, the term "psychotropic effect" refers to a modification of brain function that results in an alteration of perception, mood, consciousness, or behavior.

Unless otherwise indicated, the term "cream" as used herein relates to an emulsion of oil and water in approximately equal proportions, which penetrates stratum corneum outer layer of skin well. Creams are usually topical preparations for application to the skin. Creams for application to mucus membranes such as those of the rectum or vagina are also used. Creams may be considered pharmaceutical products, as even cosmetic creams are based on techniques developed by pharmacy and unmedicated creams are highly used in a variety of skin conditions (dermatoses). The use of the finger-tip unit concept may be helpful in guiding how much topical cream is required to cover different areas. Creams are usually semi-solid emulsions that are mixtures of oil and water. They are divided into two types: oil-in-water (O/W) creams, which are composed of small droplets of oil dispersed in a continuous phase; and water-in-oil (W/O) creams, which are composed of small droplets of water dispersed in a continuous oily phase. Oil-in-water creams are more comfortable and cosmetically acceptable as they are less greasy and more easily washed off using water. Water-in-oil creams are more difficult to handle but many drugs which are incorporated into creams are hydrophobic and will be released more readily from a water-in-oil cream than an oil-in-water cream. Water-in-oil creams are also more moisturizing as they provide an oily barrier which reduces water loss from the stratum corneum, the outermost layer of the skin.

Creams can provide a barrier to protect the skin. This may be a physical barrier or a chemical barrier as with UV-absorbing compounds. To aid in the retention of moisture (especially water-in-oil creams), creams are usually used for a variety of purposes including Swertiacleansing, emollient effects, and as a vehicle for drug substances such as local anesthetics, anti-inflammatories (NSAIDs or corticosteroids), hormones, antibiotics, antifungals or counter-irritants, and *cannabis* derived botanical drug product.

Liniments usually refer to topical formulations for application to the skin. Preparations of this type are also called balm. Liniments are of a similar viscosity to lotions (being significantly less viscous than an ointment or cream) but unlike a lotion a liniment is applied with friction; that is, a liniment is always rubbed into the skin. Liniments are typically sold to relieve pain and stiffness, such as from sore muscles or from arthritis. These liniments typically are formulated from alcohol, acetone, or similar quickly evaporating solvents and usually comprise counterirritant aromatic chemical compounds such as methyl salicilate, benzoin resin, or capsaicin.

Unless otherwise indicated, the term "ointment" relates to compositions where oil and water are present in a ratio of from 7:1 to 2:1, preferably, from 5:1 to 3:1, most preferably about 4 parts to one. Ointments provide barrier against moisture loss. Usually, ointments are formulations using oils, waxes, water, alcohols, petroleum products, water, and other agents to prepare formulations with various viscosities and solvent properties. Commonly used formulations include oleaginous base (White Ointment), absorption base, W/O emulsion base (Cold Cream type base), O/W emulsion base (Hydrophilic Ointment), water soluble base, in addition to others. These preparations are used to dissolve or suspend substances or products with medicinal or cosmetic value. These formulations are suited for incorporation *Cannabis* derived botanical drug product alone or with the addition of other substances.

Unless otherwise indicated, the term "gel" relates to compositions that liquefy upon contact with the skin.

Unless otherwise indicated, the term "paste" relates to compositions where at least the three following agents—oil, water, and powder—are combined; an ointment in which a powder is suspended.

Unless otherwise indicated, the term "lotion" relates to a low- to medium-viscosity topical preparation intended for application to unbroken skin in contrast, creams and gels have higher viscosity. Lotions are applied to external skin with bare hands, a clean cloth, cotton wool or gauze. Many lotions, especially hand lotions and body lotions are formulated not as a medicine delivery system, but simply to smooth, re-hydrate, and soften the skin. These are particularly popular with the aging and aged demographic groups, and in the case of face usage, can also be classified as a cosmetic in many cases, and may contain fragrances.

Most lotions are oil-in-water emulsions using a substance such as cetyl alcohol to keep the emulsion together, but water-in-oil lotions are also formulated. The key components of a skin care lotion, cream or gel emulsion (that is mixtures of oil and water) are the aqueous and oil phases, an emulsifier to prevent separation of these two phases, and, if used, the drug substance or substances. Other ingredients are commonly added to lotions, such as fragrances, glycerol, petroleum jelly, dyes, preservatives, proteins and stabilizing agents. Lotions can be used for the delivery to the skin of medications such as: antibiotics; antiseptics; antifungals; corticosteroids; anti-acne agents; and soothing, smoothing, moisturizing or protective agents.

As used herein, the term "nanolipid" refers to a nanoparticle comprising a solid lipid core matrix capable of solublizing lipophilic molecules, stabilized by a surfactant. The terms "nanolipid" and "solid lipid nanoparticle" have the same meaning, and are used interchangeably herein. Solid lipid nanoparticles may also be referred to simply as "nanoparticles." Nanoparticles include any particle having a diameter of less than 1000 nanometers (nm). In some embodiments, a nanoparticle has a diameter of less than 300 nm, as defined by the National Science Foundation. In some embodiments, a nanoparticle has a diameter of less than 100 nm as defined by the National Institutes of Health. In some embodiments, nanoparticles are micelles in that they comprise an enclosed compartment, separated from the bulk solution by a micellar membrane. A "micellar membrane" comprises amphiphilic entities which have aggregated to surround and enclose a space or compartment (e.g., to define a lumen).

As used herein, the term "pain" refers to a discomfort caused by intense or damaging stimuli including illness, injury, or mental anguish. The term "physical pain" refers to pain felt in the body. While physical pain can accompany emotional pain, the two types of pain are distinct. In certain embodiments, physical pain includes a differentiated pain that is localized in the body and is often associated with noxious physical stimuli. Non-limiting examples of physical pain include neuropathic pain, nociceptive pain, and nociceptive pain with an allodynic component, migraine, inflammation, osteoarthritis, rheumatoid arthritis, psoriatic arthritis, neck pain, joint pain, pain associated with plantar fasciitis, trigeminal neuralgia, vulvodynia, irritable bowel syndrome, post herpetic neuralgia and diabetic neuropathy. Other examples of physical pain involve headache, migraine headache, back pain, and lower back pain.

As used herein, the term "neuropathy" refers to a disease, disorder, or condition associated with damage and/or inflammation in nerves. Neuropathies are a subset of neurological diseases. The damage may be a symptom of another disease (e.g., diabetes, impaired glucose tolerance, Lyme disease), may be caused by injury or other external factors (e.g., infection, medication, radiation, chemotherapy), or the damage may be the pathology of the disease itself, such as in the case of hereditary neuropathies or idiopathic neuropathies. Neuropathies can affect both the central and peripheral nervous system, and may affect a single nerve, multiple nerves, or may be a polyneuropathy. Neuropathies can be chronic or acute and can affect any type of nerve or multiple types (e.g., motor, sensory, autonomic). Polyneuropathies are characterized by damage to many nerve cells often in various parts of the body. Polyneuropathies may be classified based on the part of the nerve cell most affected by the condition, including the axon, myelin sheath, or cell body.

As used herein, the term "arthritis" refers to an inflammatory disorder that includes osteoarthritis and rheumatoid arthritis. The most common form of arthritis, osteoarthritis (degenerative joint disease) is a result of trauma to the joint, infection of the joint, or age. Other arthritis forms are rheumatoid arthritis and psoriatic arthritis, autoimmune diseases in which the body attacks itself. Septic arthritis is caused by joint infection. Gouty arthritis is caused by deposition of uric acid crystals in the joint, causing inflammation.

As used herein, the term "hangover" indicates unpleasant physical and mental symptoms after drinking alcohol, and its objective symptoms include headache, nausea, vomiting, sleepiness, lowering of capacity for locomotion, hematological change and change in hormone. The cause of hangover is still unclear, but generally known to be highly associated with acetaldehyde which is a metabolic product of alcohol metabolism. That is, it is known that hangover generally occurs when the concentration of acetaldehyde remaining in the body is high.

As used herein, the term "athlete's foot fungus" refers to a skin disease, usually occurring between the toes, which is believed currently caused by a fungus. The fungus most commonly attacks the feet because shoes create a warm, dark, and humid environment which encourages fungus growth. The warmth and dampness of areas around swimming pools, showers, and locker rooms, are also breeding grounds for fungi. Because the infection was common among athletes who used these facilities frequently, the term "athlete's foot" became popular.

As used herein, the term "sunburn" refers to a radiation burn of the skin after exposure to the radiation. For example, UV radiation from the sun or tanning lamps. Common symptoms include reddening of the skin, pain to the touch, fatigue, inflammation, and dizziness. The radiation may also cause DNA damage, which may, in turn, trigger several defense mechanisms of the body including melanin production, DNA repair and peeling of the skin.

As used herein, "insect" or "insects" are used generically to refer not only to the biological species insecta, but also to related species that are commonly referred to, albeit improperly, as "insects" or "bugs." Thus, for example, "insect" or "insects" are used herein to refer to insecta, arachnids, mites, chiggers, and the like. Similarly, as used herein, "bite" is used generically to refer to an insect bite per se, such as a mosquito bite or wasp, bee or hornet sting, as well as to infestations such as burrowing, or the like, as in the case of ticks.

As used herein, the term "skin-lightening" or "skin depigmenting" means decreasing melanin in skin, including overall lightening of skin tone and lightening of hyperpigmented regions, including age spots, melasma (chloasma), freckles, post-inflammatory hyperpigmentation or sun-induced pigmented blemishes, and the like.

As used herein, the term "topical composition" refers to a composition suitable for administration to an external body surface, such as the skin.

As used herein, the term "sinus pain" refers to any pain associated with the sinus cavities, including pain from sinus headaches, sinus pressure, irritation, inflammation (sinusitis), infection, anatomical conditions, allegry, and impaired flow of mucous secretion.

As used herein, the term "afferent neuro synaptic pain signals" refers to communication transmitted between sensory neurons in response to a stimulus that causes pain.

Pharmaceutical Compositions

In an aspect, provided herein are topical compositions comprising:
propanediol;
dimethicone;
glycerin;
caprylic/capric triglycerides;
*Olea europaea* fruit oil;
biosaccharide gum-1;
dimethyl isosorbide;
ethoxydiglycol;
polysorbate 20;

a mixture consisting essentially of sodium acrylate/sodium acryloyl dimethyl taurate copolymer, cetyl alcohol, glycol stearate, and caprylic/capric triglycerides;
a mixture consisting essentially of isopropyl pamitate, lecithin, water, and *Swertia chirata* extract;
a mixture consisting essentially of propanediol and lecithin;
a mixture consisting essentially of capryl glycol and ethylhexylglycerin;
a mixture consisting essentially of water, glycerin, PEG-8, PEG-8/SMDI copolymer, palmitoyl myristyl stearate, and polyacrylate; and
the balance of the composition comprises one or more components selected from the group consisting of cannabidiol, Δ9-tetrahydrocannabinol, cannabinol, cannabigerol, cannabidiolic acid, tetrahydrocannabinolic acid, cannabigerolic acid, cannabichromene, water, amni *visnaga* oil, *Petasites japonicus* root extract, arginine, bentofiamine, butylene glycol, cetyl hydroxyethylcellulose, rutin, palmitoyl tripeptide-1, palmitoyl tetrapeptide-7, *Phaseolus lunatus* seed extract, *cannabis* oil, *Capsicum frutescens* fruit extract, *chondrus* corpus extract, sodium hyaluronate, *Citrus paradisi* oil, *Corynanthe yohimbe* extract, butylene glycol, glycerin, carbomer, polysorbate 20, palmitoyl oligopeptide, glycolic acid, *Glycyrrhiza glabra* root extract, elianthis *annuus* seed oil, *Rosmarinus officianalis* leaf extract, hexapeptide 30, hexapeptide 8, *Laminaria japonica* extract, *Melaluca alternifolia* leaf oil, *Mentha piperita* leaf oil, menthol, menthyl lactate, *Oenothera biennis* oil, *Persea gratissima* oil, *Physalis angulata* extract, capryrlic/capric triglycerides, *Pinus pinaster* bark extract, *Salix alba* bark extract, *Simmondsia chinensis* seed oil, *Tanacetum parthenium*, tocopherol, urea, *Valerian officinalis* extract, dextran, palmitoyl tripeptide-8, xanthan gum, *Euphausia superba* oil, and Cimisifuga *racemosa* extract.

In an embodiment, the composition comprises about 1% by weight propanediol. In another embodiment, the composition comprises about 2% by weight propanediol. In yet another embodiment, the composition comprises about 3% by weight propanediol. In still another embodiment, the composition comprises about 4% by weight propanediol. In another embodiment, the composition comprises about 5% by weight propanediol. In yet another embodiment, the composition comprises about 6% by weight propanediol. In still another embodiment, the composition comprises about 7% by weight propanediol. In another embodiment, the composition comprises about 8% by weight propanediol. In yet another embodiment, the composition comprises about 9% by weight propanediol. In still another embodiment, the composition comprises about 10% by weight propanediol.

In an embodiment, the composition comprises about 1% by weight dimethicone. In another embodiment, the composition comprises about 2% by weight dimethicone. In yet another embodiment, the composition comprises about 3% by weight dimethicone. In still another embodiment, the composition comprises about 4% by weight dimethicone. In another embodiment, the composition comprises about 5% by weight dimethicone. In yet another embodiment, the composition comprises about 6% by weight dimethicone. In still another embodiment, the composition comprises about 7% by weight dimethicone. In another embodiment, the composition comprises about 8% by weight dimethicone. In yet another embodiment, the composition comprises about 9% by weight dimethicone. In still another embodiment, the composition comprises about 10% by weight dimethicone.

In an embodiment, the composition comprises about 1% by weight glycerin. In another embodiment, the composition comprises about 2% by weight glycerin. In yet another embodiment, the composition comprises about 3% by weight glycerin. In still another embodiment, the composition comprises about 4% by weight glycerin. In another embodiment, the composition comprises about 5% by weight glycerin. In yet another embodiment, the composition comprises about 6% by weight glycerin. In still another embodiment, the composition comprises about 7% by weight glycerin. In another embodiment, the composition comprises about 8% by weight glycerin. In yet another embodiment, the composition comprises about 9% by weight glycerin. In still another embodiment, the composition comprises about 10% by weight glycerin.

In an embodiment, the composition comprises about 1% by weight caprylic/capric triglycerides. In another embodiment, the composition comprises about 2% by weight caprylic/capric triglycerides. In yet another embodiment, the composition comprises about 3% by weight caprylic/capric triglycerides. In still another embodiment, the composition comprises about 4% by weight caprylic/capric triglycerides. In another embodiment, the composition comprises about 5% by weight caprylic/capric triglycerides. In yet another embodiment, the composition comprises about 6% by weight caprylic/capric triglycerides. In still another embodiment, the composition comprises about 7% by weight caprylic/capric triglycerides. In another embodiment, the composition comprises about 8% by weight caprylic/capric triglycerides. In yet another embodiment, the composition comprises about 9% by weight caprylic/capric triglycerides. In still another embodiment, the composition comprises about 10% by weight caprylic/capric triglycerides.

In an embodiment, the composition comprises about 1% by weight *Olea europaea* fruit oil. In another embodiment, the composition comprises about 2% by weight *Olea europaea* fruit oil. In yet another embodiment, the composition comprises about 3% by weight *Olea europaea* fruit oil. In still another embodiment, the composition comprises about 4% by weight *Olea europaea* fruit oil. In another embodiment, the composition comprises about 5% by weight *Olea europaea* fruit oil. In yet another embodiment, the composition comprises about 6% by weight *Olea europaea* fruit oil. In still another embodiment, the composition comprises about 7% by weight *Olea europaea* fruit oil. In another embodiment, the composition comprises about 8% by weight *Olea europaea* fruit oil. In yet another embodiment, the composition comprises about 9% by weight *Olea europaea* fruit oil. In still another embodiment, the composition comprises about 10% by weight *Olea europaea* fruit oil.

In an embodiment, the composition comprises about 1% by weight biosaccharide gum-1. In another embodiment, the composition comprises about 2% by weight biosaccharide gum-1. In yet another embodiment, the composition comprises about 3% by weight biosaccharide gum-1. In still another embodiment, the composition comprises about 4% by weight biosaccharide gum-1. In another embodiment, the composition comprises about 5% by weight biosaccharide gum-1. In yet another embodiment, the composition comprises about 6% by weight biosaccharide gum-1. In still another embodiment, the composition comprises about 7% by weight biosaccharide gum-1. In another embodiment, the composition comprises about 8% by weight biosaccharide gum-1. In yet another embodiment, the composition comprises about 9% by weight glycerin. In still another embodiment, the composition comprises about 10% by weight biosaccharide gum-1.

In an embodiment, the composition comprises about 1% by weight dimethyl isosorbide. In another embodiment, the composition comprises about 2% by weight dimethyl isosorbide. In yet another embodiment, the composition comprises about 3% by weight dimethyl isosorbide. In still another embodiment, the composition comprises about 4% by weight dimethyl isosorbide. In another embodiment, the composition comprises about 5% by weight dimethyl isosorbide. In yet another embodiment, the composition comprises about 6% by weight dimethyl isosorbide. In still another embodiment, the composition comprises about 7% by weight dimethyl isosorbide. In another embodiment, the composition comprises about 8% by weight dimethyl isosorbide. In yet another embodiment, the composition comprises about 9% by weight dimethyl isosorbide. In still another embodiment, the composition comprises about 10% by weight dimethyl isosorbide.

In an embodiment, the composition comprises about 1% by weight ethoxydiglycol. In another embodiment, the composition comprises about 2% by weight ethoxydiglycol. In yet another embodiment, the composition comprises about 3% by weight ethoxydiglycol. In still another embodiment, the composition comprises about 4% by weight ethoxydiglycol. In another embodiment, the composition comprises about 5% by weight ethoxydiglycol. In yet another embodiment, the composition comprises about 6% by weight ethoxydiglycol. In still another embodiment, the composition comprises about 7% by weight ethoxydiglycol. In another embodiment, the composition comprises about 8% by weight ethoxydiglycol. In yet another embodiment, the composition comprises about 9% by weight ethoxydiglycol. In still another embodiment, the composition comprises about 10% by weight ethoxydiglycol.

In an embodiment, the composition comprises about 1% by weight polysorbate 20. In another embodiment, the composition comprises about 2% by weight polysorbate 20. In yet another embodiment, the composition comprises about 3% by weight polysorbate 20. In still another embodiment, the composition comprises about 4% by weight polysorbate 20. In another embodiment, the composition comprises about 5% by weight polysorbate 20. In yet another embodiment, the composition comprises about 6% by weight polysorbate 20. In still another embodiment, the composition comprises about 7% by weight polysorbate 20. In another embodiment, the composition comprises about 8% by weight polysorbate 20. In yet another embodiment, the composition comprises about 9% by weight polysorbate 20. In still another embodiment, the composition comprises about 10% by weight polysorbate 20.

In an embodiment, the composition comprises about 1% by weight of a mixture consisting essentially of sodium acrylate/sodium acryloyl dimethyl taurate copolymer, cetyl alcohol, glycol stearate, and caprylic/capric triglycerides. In another embodiment, the composition comprises about 2% by weight of a mixture consisting essentially of sodium acrylate/sodium acryloyl dimethyl taurate copolymer, cetyl alcohol, glycol stearate, and caprylic/capric triglycerides. In yet another embodiment, the composition comprises about 3% by weight of a mixture consisting essentially of sodium acrylate/sodium acryloyl dimethyl taurate copolymer, cetyl alcohol, glycol stearate, and caprylic/capric triglycerides. In still another embodiment, the composition comprises about 4% by weight of a mixture consisting essentially of sodium acrylate/sodium acryloyl dimethyl taurate copolymer, cetyl alcohol, glycol stearate, and caprylic/capric triglycerides. In another embodiment, the composition comprises about 5% by weight of a mixture consisting essentially of sodium acrylate/sodium acryloyl dimethyl taurate copolymer, cetyl alcohol, glycol stearate, and caprylic/capric triglycerides. In yet another embodiment, the composition comprises about 6% by weight of a mixture consisting essentially of sodium acrylate/sodium acryloyl dimethyl taurate copolymer, cetyl alcohol, glycol stearate, and caprylic/capric triglycerides. In still another embodiment, the composition comprises about 7% by weight of a mixture consisting essentially of sodium acrylate/sodium acryloyl dimethyl taurate copolymer, cetyl alcohol, glycol stearate, and caprylic/capric triglycerides. In another embodiment, the composition comprises about 8% by weight of a mixture consisting essentially of sodium acrylate/sodium acryloyl dimethyl taurate copolymer, cetyl alcohol, glycol stearate, and caprylic/capric triglycerides. In yet another embodiment, the composition comprises about 9% by weight of a mixture consisting essentially of sodium acrylate/sodium acryloyl dimethyl taurate copolymer, cetyl alcohol, glycol stearate, and caprylic/capric triglycerides. In still another embodiment, the composition comprises about 10% by weight of a mixture consisting essentially of sodium acrylate/sodium acryloyl dimethyl taurate copolymer, cetyl alcohol, glycol stearate, and caprylic/capric triglycerides.

In an embodiment, the composition comprises about 1% by weight of a mixture consisting essentially of isopropyl pamitate, lecithin, water, and *Swertia chirata* extract. In another embodiment, the composition comprises about 2% by weight of a mixture consisting essentially of isopropyl pamitate, lecithin, water, and *Swertia chirata* extract. In yet another embodiment, the composition comprises about 3% by weight of a mixture consisting essentially of isopropyl pamitate, lecithin, water, and *Swertia chirata* extract. In still another embodiment, the composition comprises about 4% by weight of a mixture consisting essentially of isopropyl pamitate, lecithin, water, and *Swertia chirata* extract. In another embodiment, the composition comprises about 5% by weight of a mixture consisting essentially of isopropyl pamitate, lecithin, water, and *Swertia chirata* extract. In yet another embodiment, the composition comprises about 6% by weight of a mixture consisting essentially of isopropyl pamitate, lecithin, water, and *Swertia chirata* extract. In still another embodiment, the composition comprises about 7% by weight of a mixture consisting essentially of isopropyl pamitate, lecithin, water, and *Swertia chirata* extract. In another embodiment, the composition comprises about 8% by weight of a mixture consisting essentially of isopropyl pamitate, lecithin, water, and *Swertia chirata* extract. In yet another embodiment, the composition comprises about 9% by weight of a mixture consisting essentially of isopropyl pamitate, lecithin, water, and *Swertia chirata* extract. In still another embodiment, the composition comprises about 10% by weight of a mixture consisting essentially of isopropyl pamitate, lecithin, water, and *Swertia chirata* extract.

In an embodiment, the composition comprises about 1% by weight of a mixture consisting essentially of propanediol and lecithin. In another embodiment, the composition comprises about 2% by weight of a mixture consisting essentially of propanediol and lecithin. In yet another embodiment, the composition comprises about 3% by weight of a mixture consisting essentially of propanediol and lecithin. In still another embodiment, the composition comprises about 4% by weight of a mixture consisting essentially of propanediol and lecithin. In another embodiment, the composition comprises about 5% by weight of a mixture consisting essentially of propanediol and lecithin. In yet another embodiment, the composition comprises about 6% by weight of a mixture consisting essentially of propanediol and lecithin. In still another embodiment, the composition comprises about 7% by weight of a mixture consisting essentially of propanediol and lecithin. In another embodiment, the composition comprises about 8% by weight of a mixture consisting essentially of propanediol and lecithin. In yet another embodiment, the composition comprises about 9% by weight of a mixture consisting essentially of propanediol and lecithin. In still another embodiment, the composition comprises about 10% by weight of a mixture consisting essentially of propanediol and lecithin.

In an embodiment, the composition comprises about 1% by weight of a mixture consisting essentially of capryl glycol and ethylhexylglycerin. In another embodiment, the composition comprises about 1.1% by weight of a mixture consisting essentially of capryl glycol and ethylhexylglycerin. In yet another embodiment, the composition comprises about 1.2% by weight of a mixture consisting essentially of capryl glycol and ethylhexylglycerin. In still another embodiment, the composition comprises about 1.3% by weight of a mixture consisting essentially of capryl glycol and ethylhexylglycerin. In another embodiment, the composition comprises about 1.4% by weight of a mixture consisting essentially of capryl glycol and ethylhexylglycerin. In yet another embodiment, the composition comprises about 1.5% by weight of a mixture consisting essentially of capryl glycol and ethylhexylglycerin. In still another embodiment, the composition comprises about 1.6% by weight of a mixture consisting essentially of capryl glycol and ethylhexylglycerin. In another embodiment, the composition comprises about 1.7% by weight of a mixture consisting essentially of capryl glycol and ethylhexylglycerin. In yet another embodiment, the composition comprises about 1.8% by weight of a mixture consisting essentially of capryl glycol and ethylhexylglycerin. In still another embodiment, the composition comprises about 1.9% by weight of a mixture consisting essentially of capryl glycol and ethylhexylglycerin.

In another embodiment, the composition comprises about 2% by weight of a mixture consisting essentially of capryl glycol and ethylhexylglycerin. In yet another embodiment, the composition comprises about 3% by weight of a mixture consisting essentially of capryl glycol and ethylhexylglycerin. In still another embodiment, the composition comprises about 4% by weight of a mixture consisting essentially of capryl glycol and ethylhexylglycerin. In another embodiment, the composition comprises about 5% by weight of a mixture consisting essentially of capryl glycol and ethylhexylglycerin. In yet another embodiment, the composition comprises about 6% by weight of a mixture consisting essentially of capryl glycol and ethylhexylglycerin. In still another embodiment, the composition comprises about 7% by weight of a mixture consisting essentially of capryl glycol and ethylhexylglycerin. In another embodiment, the composition comprises about 8% by weight of a mixture consisting essentially of capryl glycol and ethylhexylglycerin. In yet another embodiment, the composition comprises about 9% by weight of a mixture consisting essentially of capryl glycol and ethylhexylglycerin. In still another embodiment, the composition comprises about 10% by weight of a mixture consisting essentially of capryl glycol and ethylhexylglycerin.

In an embodiment, the composition comprises about 1% by weight of a mixture consisting essentially of water, glycerin, PEG-8, PEG-8/SMDI copolymer, palmitoyl myristyl stearate, and polyacrylate. In another embodiment, the composition comprises about 2% by weight of a mixture consisting essentially of water, glycerin, PEG-8, PEG-8/SMDI copolymer, palmitoyl myristyl stearate, and polyacrylate. In yet another embodiment, the composition comprises about 3% by weight of a mixture consisting essentially of water, glycerin, PEG-8, PEG-8/SMDI copolymer, palmitoyl myristyl stearate, and polyacrylate. In still another embodiment, the composition comprises about 4% by weight of a mixture consisting essentially of water, glycerin, PEG-8, PEG-8/SMDI copolymer, palmitoyl myristyl stearate, and polyacrylate. In another embodiment, the composition comprises about 5% by weight of a mixture consisting essentially of water, glycerin, PEG-8, PEG-8/SMDI copolymer, palmitoyl myristyl stearate, and polyacrylate. In yet another embodiment, the composition comprises about 6% by weight of a mixture consisting essentially of water, glycerin, PEG-8, PEG-8/SMDI copolymer, palmitoyl myristyl stearate, and polyacrylate. In still another embodiment, the composition comprises about 7% by weight of a mixture consisting essentially of water, glycerin, PEG-8, PEG-8/SMDI copolymer, palmitoyl myristyl stearate, and polyacrylate. In another embodiment, the composition comprises about 8% by weight of a mixture consisting essentially of water, glycerin, PEG-8, PEG-8/SMDI copolymer, palmitoyl myristyl stearate, and polyacrylate. In yet another embodiment, the composition comprises about 9% by weight of a mixture consisting essentially of water, glycerin, PEG-8, PEG-8/SMDI copolymer, palmitoyl myristyl stearate, and polyacrylate. In still another embodiment, the composition comprises about 10% by weight of a mixture consisting essentially of water, glycerin, PEG-8, PEG-8/SMDI copolymer, palmitoyl myristyl stearate, and polyacrylate.

In an embodiment, the composition comprises:
about 4% by weight propanediol;
about 5% by weight dimethicone;
about 4% by weight glycerin;
about 2% by weight caprylic/capric triglycerides;
about 2% by weight *Olea europaea* fruit oil;
about 3% by weight biosaccharide gum-1;
about 2% by weight dimethyl isosorbide;
about 2% by weight ethoxydiglycol;
about 2% by weight polysorbate 20;
about 5% by weight of a mixture consisting essentially of sodium acrylate/sodium acryloyl dimethyl taurate copolymer, cetyl alcohol, glycol stearate, and caprylic/capric triglycerides;
about 2% by weight of a mixture consisting essentially of isopropyl pamitate, lecithin, water, and *Swertia chirata* extract;
about 5% by weight of a mixture consisting essentially of propanediol and lecithin;
about 1.2% by weight of a mixture consisting essentially of capryl glycol and ethylhexylglycerin;
about 2% by weight of a mixture consisting essentially of water, glycerin, PEG-8, PEG-8/SMDI copolymer, palmitoyl myristyl stearate, and polyacrylate; and
the balance of the composition comprises one or more components selected from the group consisting of cannabidiol, Δ9-tetrahydrocannabinol, cannabinol, cannabigerol, cannabidiolic acid, tetrahydrocannabinolic acid, cannabigerolic acid, cannabichromene, water, amni *visnaga* oil, *Petasites japonicus* root extract, arginine, bentofiamine, butylene glycol, cetyl hydroxyethylcellulose, rutin, palmitoyl tripeptide-1, palmitoyl tetrapeptide-7, *Phaseolus lunatus* seed extract, *cannabis* oil, *Capsicum frutescens* fruit extract, *chondrus* corpus extract, sodium hyaluronate, *Citrus paradisi* oil, *Corynanthe yohimbe* extract, butylene glycol, glycerin, carbomer, polysorbate 20, palmitoyl oligopeptide, glycolic acid, *Glycyrrhiza glabra* root extract, *Helianthis annuus* seed oil, *Rosmarinus officianalis* leaf extract, hexapeptide 30, hexapeptide 8, *Laminaria japonica* extract, *Melaluca alternifolia* leaf oil, *Mentha piperita* leaf oil, menthol, menthyl lactate, *Oenothera biennis* oil, *Persea gratissima* oil, *Physalis angulata* extract, capyrylic/capric triglycerides, *Pinus pinaster* bark extract, *Salix alba* bark extract, *Simmondsia chinensis* seed oil, *Tanacetum parthenium*, tocopherol, urea, *Valerian officinalis* extract, dextran, palmitoyl tripeptide-8, xanthan gum, *Euphausia superba* oil, and Cimisifuga *racemosa* extract.

In an embodiment, the balance of the mixture comprises about 0.001% by weight amni *visnaga* oil. In another embodiment, the balance of the mixture comprises about 0.002% by weight amni *visnaga* oil. In yet another embodiment, the balance of the mixture comprises about 0.003% by weight amni *visnaga* oil. In still another embodiment, the balance of the mixture comprises about 0.004% by weight amni *visnaga* oil. In another embodiment, the balance of the mixture comprises about 0.005% by weight amni *visnaga* oil. In yet another embodiment, the balance of the mixture comprises about 0.006% by weight amni *visnaga* oil. In still another embodiment, the balance of the mixture comprises about 0.007% by weight amni *visnaga* oil. In another embodiment, the balance of the mixture comprises about 0.008% by weight amni *visnaga* oil. In yet another embodiment, the balance of the mixture comprises about 0.009% by weight amni *visnaga* oil.

In an embodiment, the balance of the mixture comprises about 0.001% by weight of a mixture consisting essentially of *Petasites japonicus* root extract and water. In another embodiment, the balance of the mixture comprises about 0.002% by weight of a mixture consisting essentially of *Petasites japonicus* root extract and water. In yet another embodiment, the balance of the mixture comprises about 0.003% by weight of a mixture consisting essentially of *Petasites japonicus* root extract and water. In still another embodiment, the balance of the mixture comprises about 0.004% by weight of a mixture consisting essentially of *petasites japonicus* root extract and water. In another embodiment, the balance of the mixture comprises about 0.005% by weight of a mixture consisting essentially of *Petasites japonicus* root extract and water. In yet another embodiment, the balance of the mixture comprises about 0.006% by weight of a mixture consisting essentially of *Petasites japonicus* root extract and water. In still another embodiment, the balance of the mixture comprises about 0.007% by weight of a mixture consisting essentially of *Petasites japonicus* root extract and water. In another embodiment, the balance of the mixture comprises about 0.008% by weight of a mixture consisting essentially of *Petasites japonicus* root extract and water. In yet another embodiment, the balance of the mixture comprises about 0.009% by weight of a mixture consisting essentially of *petasites japonicus* root extract and water.

In an embodiment, the balance of the mixture comprises about 0.001% by weight arginine. In another embodiment, the balance of the mixture comprises about 0.002% by weight arginine. In yet another embodiment, the balance of the mixture comprises about 0.003% by weight arginine. In still another embodiment, the balance of the mixture comprises about 0.004% by weight arginine. In another embodiment, the balance of the mixture comprises about 0.005% by weight arginine. In yet another embodiment, the balance of the mixture comprises about 0.006% by weight arginine. In still another embodiment, the balance of the mixture comprises about 0.007% by weight arginine. In another embodiment, the balance of the mixture comprises about 0.008% by weight arginine. In yet another embodiment, the balance of the mixture comprises about 0.009% by weight arginine.

In an embodiment, the balance of the mixture comprises about 0.001% by weight bentofiamine. In another embodiment, the balance of the mixture comprises about 0.002% by weight bentofiamine. In yet another embodiment, the balance of the mixture comprises about 0.003% by weight bentofiamine. In still another embodiment, the balance of the mixture comprises about 0.004% by weight bentofiamine. In another embodiment, the balance of the mixture comprises about 0.005% by weight bentofiamine. In yet another embodiment, the balance of the mixture comprises about 0.006% by weight bentofiamine. In still another embodiment, the balance of the mixture comprises about 0.007% by weight bentofiamine. In another embodiment, the balance of the mixture comprises about 0.008% by weight bentofiamine. In yet another embodiment, the balance of the mixture comprises about 0.009% by weight bentofiamine.

In an embodiment, the balance of the mixture comprises about 0.001% by weight of a mixture consisting essentially of butylene glycol, cetyl hydroxyethylcellulose, rutin, palmitoyl tripeptide-1, palmitoyl tetrapeptide-7, *Phaseolus lunatus* seed extract, and water. In another embodiment, the balance of the mixture comprises about 0.002% by weight of a mixture consisting essentially of butylene glycol, cetyl hydroxyethylcellulose, rutin, palmitoyl tripeptide-1, palmitoyl tetrapeptide-7, *Phaseolus lunatus* seed extract, and water. In yet another embodiment, the balance of the mixture comprises about 0.003% by weight of a mixture consisting essentially of butylene glycol, cetyl hydroxyethylcellulose, rutin, palmitoyl tripeptide-1, palmitoyl tetrapeptide-7, *Phaseolus lunatus* seed extract, and water. In still another embodiment, the balance of the mixture comprises about 0.004% by weight of a mixture consisting essentially of butylene glycol, cetyl hydroxyethylcellulose, rutin, palmitoyl tripeptide-1, palmitoyl tetrapeptide-7, *Phaseolus lunatus* seed extract, and water. In another embodiment, the balance of the mixture comprises about 0.005% by weight of a mixture consisting essentially of butylene glycol, cetyl hydroxyethylcellulose, rutin, palmitoyl tripeptide-1, palmitoyl tetrapeptide-7, *Phaseolus lunatus* seed extract, and water. In yet another embodiment, the balance of the mixture comprises about 0.006% by weight of a mixture consisting essentially of butylene glycol, cetyl hydroxyethylcellulose, rutin, palmitoyl tripeptide-1, palmitoyl tetrapeptide-7, *Phaseolus lunatus* seed extract, and water. In still another embodiment, the balance of the mixture comprises about 0.007% by weight of a mixture consisting essentially of butylene glycol, cetyl hydroxyethylcellulose, rutin, palmitoyl tripeptide-1, palmitoyl tetrapeptide-7, *Phaseolus lunatus* seed extract, and water. In another embodiment, the balance of the mixture comprises about 0.008% by weight of a mixture consisting essentially of butylene glycol, cetyl hydroxyethylcellulose, rutin, palmitoyl tripeptide-1, palmitoyl tetrapeptide-7, *Phaseolus lunatus* seed extract, and water. In yet another embodiment, the balance of the mixture comprises about 0.009% by weight of a mixture consisting essentially of butylene glycol, cetyl hydroxyethylcellulose, rutin, palmitoyl tripeptide-1, palmitoyl tetrapeptide-7, *Phaseolus lunatus* seed extract, and water.

In an embodiment, the balance of the mixture comprises from about 0.001% to about 10% by weight of a component selected from the group consisting of *cannabis* oil, cannabidiol, Δ9-tetrahydrocannabinol, cannabinol, cannabigerol, cannabidiolic acid, tetrahydrocannabinolic acid, cannabigerolic acid, and cannabichromene. In another embodiment, the balance of the mixture comprises about 0.001% by weight of a component selected from the group consisting of *cannabis* oil, cannabidiol, Δ9-tetrahydrocannabinol, cannabinol, cannabigerol, cannabidiolic acid, tetrahydrocannabinolic acid, cannabigerolic acid, and cannabichromene. In yet another embodiment, the balance of the mixture comprises about 0.002% by weight of a component selected from the group consisting of *cannabis* oil, cannabidiol, Δ9-tetrahydrocannabinol, cannabinol, cannabigerol, cannabidiolic acid, tetrahydrocannabinolic acid, cannabigerolic acid, and cannabichromene. In still another embodiment, the balance of the mixture comprises about 0.003% by weight of a component selected from the group consisting of *cannabis* oil, cannabidiol, Δ9-tetrahydrocannabinol, cannabinol, cannabigerol, cannabidiolic acid, tetrahydrocannabinolic acid, cannabigerolic acid, and cannabichromene.

In another embodiment, the balance of the mixture comprises about 0.004% by weight of a component selected from the group consisting of *cannabis* oil, cannabidiol, Δ9-tetrahydrocannabinol, cannabinol, cannabigerol, cannabidiolic acid, tetrahydrocannabinolic acid, cannabigerolic acid, and cannabichromene. In yet another embodiment, the balance of the mixture comprises about 0.005% by weight of a component selected from the group consisting of *cannabis* oil, cannabidiol, Δ9-tetrahydrocannabinol, cannabinol, cannabigerol, cannabidiolic acid, tetrahydrocannabinolic acid, cannabigerolic acid, and cannabichromene. In still another embodiment, the balance of the mixture comprises about 0.006% by weight of a component selected from the group consisting of *cannabis* oil, cannabidiol, Δ9-tetrahydrocannabinol, cannabinol, cannabigerol, cannabidiolic acid, tetrahydrocannabinolic acid, cannabigerolic acid, and cannabichromene.

In another embodiment, the balance of the mixture comprises about 0.007% by weight of a component selected from the group consisting of *cannabis* oil, cannabidiol, Δ9-tetrahydrocannabinol, cannabinol, cannabigerol, cannabidiolic acid, tetrahydrocannabinolic acid, cannabigerolic acid, and cannabichromene. In yet another embodiment, the balance of the mixture comprises about 0.008% by weight of a component selected from the group consisting of *cannabis* oil, cannabidiol, Δ9-tetrahydrocannabinol, cannabinol, cannabigerol, cannabidiolic acid, tetrahydrocannabinolic acid, cannabigerolic acid, and cannabichromene. In still another embodiment, the balance of the mixture comprises about 0.009% by weight of a component selected from the group consisting of *cannabis* oil, cannabidiol, Δ9-tetrahydrocannabinol, cannabinol, cannabigerol, cannabidiolic acid, tetrahydrocannabinolic acid, cannabigerolic acid, and cannabichromene.

In another embodiment, the balance of the mixture comprises about 0.01% by weight of a component selected from the group consisting of *cannabis* oil, cannabidiol, Δ9-tetrahydrocannabinol, cannabinol, cannabigerol, cannabidiolic acid, tetrahydrocannabinolic acid, cannabigerolic acid, and cannabichromene. In yet another embodiment, the balance of the mixture comprises about 0.02% by weight of a component selected from the group consisting of *cannabis* oil, cannabidiol, Δ9-tetrahydrocannabinol, cannabinol, cannabigerol, cannabidiolic acid, tetrahydrocannabinolic acid, cannabigerolic acid, and cannabichromene. In still another embodiment, the balance of the mixture comprises about 0.03% by weight of a component selected from the group consisting of *cannabis* oil, cannabidiol, Δ9-tetrahydrocannabinol, cannabinol, cannabigerol, cannabidiolic acid, tetrahydrocannabinolic acid, cannabigerolic acid, and cannabichromene.

In another embodiment, the balance of the mixture comprises about 0.04% by weight of a component selected from the group consisting of *cannabis* oil, cannabidiol, Δ9-tetrahydrocannabinol, cannabinol, cannabigerol, cannabidiolic acid, tetrahydrocannabinolic acid, cannabigerolic acid, and cannabichromene. In yet another embodiment, the balance of the mixture comprises about 0.05% by weight of a component selected from the group consisting of *cannabis* oil, cannabidiol, Δ9-tetrahydrocannabinol, cannabinol, cannabigerol, cannabidiolic acid, tetrahydrocannabinolic acid, cannabigerolic acid, and cannabichromene. In still another embodiment, the balance of the mixture comprises about 0.06% by weight of a component selected from the group consisting of *cannabis* oil, cannabidiol, Δ9-tetrahydrocannabinol, cannabinol, cannabigerol, cannabidiolic acid, tetrahydrocannabinolic acid, cannabigerolic acid, and cannabichromene.

In another embodiment, the balance of the mixture comprises about 0.07% by weight of a component selected from the group consisting of *cannabis* oil, cannabidiol, Δ9-tetrahydrocannabinol, cannabinol, cannabigerol, cannabidiolic acid, tetrahydrocannabinolic acid, cannabigerolic acid, and cannabichromene. In yet another embodiment, the balance of the mixture comprises about 0.08% by weight of a component selected from the group consisting of *cannabis* oil, cannabidiol, Δ9-tetrahydrocannabinol, cannabinol, cannabigerol, cannabidiolic acid, tetrahydrocannabinolic acid, cannabigerolic acid, and cannabichromene. In still another embodiment, the balance of the mixture comprises about 0.09% by weight of a component selected from the group consisting of *cannabis* oil, cannabidiol, Δ9-tetrahydrocannabinol, cannabinol, cannabigerol, cannabidiolic acid, tetrahydrocannabinolic acid, cannabigerolic acid, and cannabichromene.

In another embodiment, the balance of the mixture comprises about 0.1% by weight of a component selected from the group consisting of *cannabis* oil, cannabidiol, Δ9-tetrahydrocannabinol, cannabinol, cannabigerol, cannabidiolic acid, tetrahydrocannabinolic acid, cannabigerolic acid, and cannabichromene. In another embodiment, the balance of the mixture comprises about 0.125% by weight of a component selected from the group consisting of *cannabis* oil, cannabidiol, Δ9-tetrahydrocannabinol, cannabinol, cannabigerol, cannabidiolic acid, tetrahydrocannabinolic acid, cannabigerolic acid, and cannabichromene. In yet another embodiment, the balance of the mixture comprises about 0.2% by weight of a component selected from the group consisting of *cannabis* oil, cannabidiol, Δ9-tetrahydrocannabinol, cannabinol, cannabigerol, cannabidiolic acid, tetrahydrocannabinolic acid, cannabigerolic acid, and cannabichromene. In still another embodiment, the balance of the mixture comprises about 0.3% by weight of a component selected from the group consisting of *cannabis* oil, cannabidiol, Δ9-tetrahydrocannabinol, cannabinol, cannabigerol, cannabidiolic acid, tetrahydrocannabinolic acid, cannabigerolic acid, and cannabichromene.

In another embodiment, the balance of the mixture comprises about 0.4% by weight of a component selected from the group consisting of *cannabis* oil, cannabidiol, Δ9-tetrahydrocannabinol, cannabinol, cannabigerol, cannabidiolic acid, tetrahydrocannabinolic acid, cannabigerolic acid, and cannabichromene. In yet another embodiment, the balance of the mixture comprises about 0.5% by weight of a component selected from the group consisting of *cannabis* oil, cannabidiol, Δ9-tetrahydrocannabinol, cannabinol, cannabigerol, cannabidiolic acid, tetrahydrocannabinolic acid, cannabigerolic acid, and cannabichromene. In still another embodiment, the balance of the mixture comprises about 0.6% by weight of a component selected from the group consisting of *cannabis* oil, cannabidiol, Δ9-tetrahydrocannabinol, cannabinol, cannabigerol, cannabidiolic acid, tetrahydrocannabinolic acid, cannabigerolic acid, and cannabichromene. In yet another embodiment, the balance of the mixture comprises about 0.7% by weight of a component selected from the group consisting of *cannabis* oil, cannabidiol, Δ9-tetrahydrocannabinol, cannabinol, cannabigerol, cannabidiolic acid, tetrahydrocannabinolic acid, cannabigerolic acid, and cannabichromene. In yet another embodiment, the balance of the mixture comprises about 0.8% by weight of a component selected from the group consisting of *cannabis* oil, cannabidiol, Δ9-tetrahydrocannabinol, cannabinol, cannabigerol, cannabidiolic acid, tetrahydrocannabinolic acid, cannabigerolic acid, and cannabichromene. In still another embodiment, the balance of the mixture comprises about 0.9% by weight of a component selected from the group consisting of *cannabis* oil, cannabidiol, Δ9-tetrahydrocannabinol, cannabinol, cannabigerol, cannabidiolic acid, tetrahydrocannabinolic acid, cannabigerolic acid, and cannabichromene.

In an embodiment, the *cannabis* oil comprises from about 0.001% to about 100% by weight cannabidiol. In another embodiment, the *cannabis* oil comprises from about 0.001% to about 10% by weight cannabidiol. In another embodiment, the *cannabis* oil comprises about 0% by weight cannabidiol. In another embodiment, the *cannabis* oil comprises about 0.001% by weight cannabidiol. In yet another embodiment, the *cannabis* oil comprises about 0.002% by weight cannabidiol. In still another embodiment, the *cannabis* oil comprises about 0.003% by weight cannabidiol. In another embodiment, the *cannabis* oil comprises about 0.004% by weight cannabidiol. In yet another embodiment, the *cannabis* oil comprises about 0.005% by weight cannabidiol. In still another embodiment, the *cannabis* oil comprises about 0.006% by weight cannabidiol. In another embodiment, the *cannabis* oil comprises about 0.007% by weight cannabidiol. In yet another embodiment, the *cannabis* oil comprises about 0.008% by weight cannabidiol. In still another embodiment, the *cannabis* oil comprises about 0.009% by weight cannabidiol.

In another embodiment, the *cannabis* oil comprises about 0.01% by weight cannabidiol. In yet another embodiment, the *cannabis* oil comprises about 0.02% by weight cannabidiol. In still another embodiment, the *cannabis* oil comprises about 0.03% by weight cannabidiol. In another embodiment, the *cannabis* oil comprises about 0.04% by weight cannabidiol. In yet another embodiment, the *cannabis* oil comprises about 0.05% by weight cannabidiol. In still another embodiment, the *cannabis* oil comprises about 0.06% by weight cannabidiol. In another embodiment, the *cannabis* oil comprises about 0.07% by weight cannabidiol. In yet another embodiment, the *cannabis* oil comprises about 0.08% by weight cannabidiol. In still another embodiment, the *cannabis* oil comprises about 0.09% by weight cannabidiol.

In another embodiment, the *cannabis* oil comprises about 0.1% by weight cannabidiol. In yet another embodiment, the *cannabis* oil comprises about 0.2% by weight cannabidiol. In still another embodiment, the *cannabis* oil comprises about 0.3% by weight cannabidiol. In another embodiment, the *cannabis* oil comprises about 0.4% by weight cannabidiol. In yet another embodiment, the *cannabis* oil comprises about 0.5% by weight cannabidiol. In still another embodiment, the *cannabis* oil comprises about 0.6% by weight cannabidiol. In another embodiment, the *cannabis* oil comprises about 0.7% by weight cannabidiol. In yet another embodiment, the *cannabis* oil comprises about 0.8% by weight cannabidiol. In still another embodiment, the *cannabis* oil comprises about 0.9% by weight cannabidiol.

In another embodiment, the *cannabis* oil comprises about 1% by weight cannabidiol. In yet another embodiment, the *cannabis* oil comprises about 2% by weight cannabidiol. In still another embodiment, the *cannabis* oil comprises about 3% by weight cannabidiol. In another embodiment, the *cannabis* oil comprises about 4% by weight cannabidiol. In yet another embodiment, the *cannabis* oil comprises about 5% by weight cannabidiol. In still another embodiment, the *cannabis* oil comprises about 6% by weight cannabidiol. In another embodiment, the *cannabis* oil comprises about 7% by weight cannabidiol. In yet another embodiment, the *cannabis* oil comprises about 8% by weight cannabidiol. In still another embodiment, the *cannabis* oil comprises about 9% by weight cannabidiol. In another embodiment, the *cannabis* oil comprises about 10% by weight cannabidiol.

In another embodiment, the *cannabis* oil comprises about 11% by weight cannabidiol. In yet another embodiment, the *cannabis* oil comprises about 12% by weight cannabidiol. In still another embodiment, the *cannabis* oil comprises about 13% by weight cannabidiol. In another embodiment, the *cannabis* oil comprises about 14% by weight cannabidiol. In yet another embodiment, the *cannabis* oil comprises about 15% by weight cannabidiol. In still another embodiment, the *cannabis* oil comprises about 16% by weight cannabidiol. In another embodiment, the *cannabis* oil comprises about 17% by weight cannabidiol. In yet another embodiment, the *cannabis* oil comprises about 18% by weight cannabidiol. In still another embodiment, the *cannabis* oil comprises about 19% by weight cannabidiol. In another embodiment, the *cannabis* oil comprises about 20% by weight cannabidiol.

In another embodiment, the *cannabis* oil comprises about 21% by weight cannabidiol. In yet another embodiment, the *cannabis* oil comprises about 22% by weight cannabidiol. In still another embodiment, the *cannabis* oil comprises about 23% by weight cannabidiol. In another embodiment, the *cannabis* oil comprises about 24% by weight cannabidiol. In yet another embodiment, the *cannabis* oil comprises about 25% by weight cannabidiol. In still another embodiment, the *cannabis* oil comprises about 26% by weight cannabidiol. In another embodiment, the *cannabis* oil comprises about 27% by weight cannabidiol. In yet another embodiment, the *cannabis* oil comprises about 28% by weight cannabidiol. In still another embodiment, the *cannabis* oil comprises about 29% by weight cannabidiol. In another embodiment, the *cannabis* oil comprises about 30% by weight cannabidiol.

In another embodiment, the *cannabis* oil comprises about 31% by weight cannabidiol. In yet another embodiment, the *cannabis* oil comprises about 32% by weight cannabidiol. In still another embodiment, the *cannabis* oil comprises about 33% by weight cannabidiol. In another embodiment, the *cannabis* oil comprises about 34% by weight cannabidiol. In yet another embodiment, the *cannabis* oil comprises about 35% by weight cannabidiol. In still another embodiment, the *cannabis* oil comprises about 36% by weight cannabidiol. In another embodiment, the *cannabis* oil comprises about 37% by weight cannabidiol. In yet another embodiment, the *cannabis* oil comprises about 38% by weight cannabidiol. In still another embodiment, the *cannabis* oil comprises about 39% by weight cannabidiol. In another embodiment, the *cannabis* oil comprises about 40% by weight cannabidiol.

In another embodiment, the *cannabis* oil comprises about 41% by weight cannabidiol. In yet another embodiment, the *cannabis* oil comprises about 42% by weight cannabidiol. In still another embodiment, the *cannabis* oil comprises about 43% by weight cannabidiol. In another embodiment, the *cannabis* oil comprises about 44% by weight cannabidiol. In yet another embodiment, the *cannabis* oil comprises about 45% by weight cannabidiol. In still another embodiment, the *cannabis* oil comprises about 46% by weight cannabidiol. In another embodiment, the *cannabis* oil comprises about 47% by weight cannabidiol. In yet another embodiment, the *cannabis* oil comprises about 48% by weight cannabidiol. In still another embodiment, the *cannabis* oil comprises about 49% by weight cannabidiol. In another embodiment, the *cannabis* oil comprises about 50% by weight cannabidiol.

In another embodiment, the *cannabis* oil comprises about 51% by weight cannabidiol. In yet another embodiment, the *cannabis* oil comprises about 52% by weight cannabidiol. In still another embodiment, the *cannabis* oil comprises about 53% by weight cannabidiol. In another embodiment, the *cannabis* oil comprises about 54% by weight cannabidiol. In yet another embodiment, the *cannabis* oil comprises about 55% by weight cannabidiol. In still another embodiment, the *cannabis* oil comprises about 56% by weight cannabidiol. In another embodiment, the *cannabis* oil comprises about 57% by weight cannabidiol. In yet another embodiment, the *cannabis* oil comprises about 58% by weight cannabidiol. In still another embodiment, the *cannabis* oil comprises about 59% by weight cannabidiol. In another embodiment, the *cannabis* oil comprises about 60% by weight cannabidiol.

In another embodiment, the *cannabis* oil comprises about 61% by weight cannabidiol. In yet another embodiment, the *cannabis* oil comprises about 62% by weight cannabidiol. In still another embodiment, the *cannabis* oil comprises about 63% by weight cannabidiol. In another embodiment, the *cannabis* oil comprises about 64% by weight cannabidiol. In yet another embodiment, the *cannabis* oil comprises about 65% by weight cannabidiol. In still another embodiment, the *cannabis* oil comprises about 66% by weight cannabidiol. In another embodiment, the *cannabis* oil comprises about 67% by weight cannabidiol. In yet another embodiment, the *cannabis* oil comprises about 68% by weight cannabidiol. In still another embodiment, the *cannabis* oil comprises about 69% by weight cannabidiol. In another embodiment, the *cannabis* oil comprises about 70% by weight cannabidiol.

In another embodiment, the *cannabis* oil comprises about 71% by weight cannabidiol. In yet another embodiment, the *cannabis* oil comprises about 72% by weight cannabidiol. In still another embodiment, the *cannabis* oil comprises about 73% by weight cannabidiol. In another embodiment, the *cannabis* oil comprises about 74% by weight cannabidiol. In yet another embodiment, the *cannabis* oil comprises about 75% by weight cannabidiol. In still another embodiment, the *cannabis* oil comprises about 76% by weight cannabidiol. In another embodiment, the *cannabis* oil comprises about 77% by weight cannabidiol. In yet another embodiment, the *cannabis* oil comprises about 78% by weight cannabidiol. In still another embodiment, the *cannabis* oil comprises about 79% by weight cannabidiol. In another embodiment, the *cannabis* oil comprises about 80% by weight cannabidiol.

In another embodiment, the *cannabis* oil comprises about 81% by weight cannabidiol. In yet another embodiment, the *cannabis* oil comprises about 82% by weight cannabidiol. In still another embodiment, the *cannabis* oil comprises about 83% by weight cannabidiol. In another embodiment, the *cannabis* oil comprises about 84% by weight cannabidiol. In yet another embodiment, the *cannabis* oil comprises about 85% by weight cannabidiol. In still another embodiment, the *cannabis* oil comprises about 86% by weight cannabidiol. In another embodiment, the *cannabis* oil comprises about 87% by weight cannabidiol. In yet another embodiment, the *cannabis* oil comprises about 88% by weight cannabidiol. In still another embodiment, the *cannabis* oil comprises about 89% by weight cannabidiol. In another embodiment, the *cannabis* oil comprises about 90% by weight cannabidiol.

In another embodiment, the *cannabis* oil comprises about 91% by weight cannabidiol. In yet another embodiment, the *cannabis* oil comprises about 92% by weight cannabidiol. In still another embodiment, the *cannabis* oil comprises about 93% by weight cannabidiol. In another embodiment, the *cannabis* oil comprises about 94% by weight cannabidiol. In yet another embodiment, the *cannabis* oil comprises about 95% by weight cannabidiol. In still another embodiment, the *cannabis* oil comprises about 96% by weight cannabidiol. In another embodiment, the *cannabis* oil comprises about 97% by weight cannabidiol. In yet another embodiment, the *cannabis* oil comprises about 98% by weight cannabidiol. In still another embodiment, the *cannabis* oil comprises about 99% by weight cannabidiol. In another embodiment, the *cannabis* oil comprises about 100% by weight cannabidiol.

In another embodiment, the *cannabis* oil comprises less than about 0.1% by weight cannabidiol. In yet another embodiment, the *cannabis* oil comprises less than about 0.2% by weight cannabidiol. In still another embodiment, the *cannabis* oil comprises less than about 0.3% by weight cannabidiol. In another embodiment, the *cannabis* oil comprises less than about 0.4% by weight cannabidiol. In yet another embodiment, the *cannabis* oil comprises less than about 0.5% by weight cannabidiol. In still another embodiment, the *cannabis* oil comprises less than about 0.6% by weight cannabidiol. In another embodiment, the *cannabis* oil comprises less than about 0.7% by weight cannabidiol. In yet another embodiment, the *cannabis* oil comprises less than about 0.8% by weight cannabidiol. In still another embodiment, the *cannabis* oil comprises less than about 0.9% by weight cannabidiol.

In another embodiment, the *cannabis* oil comprises less than about 1% by weight cannabidiol. In yet another embodiment, the *cannabis* oil comprises less than about 2% by weight cannabidiol. In still another embodiment, the *cannabis* oil comprises less than about 3% by weight cannabidiol. In another embodiment, the *cannabis* oil comprises less than about 4% by weight cannabidiol. In yet another embodiment, the *cannabis* oil comprises less than about 5% by weight cannabidiol. In still another embodiment, the *cannabis* oil comprises less than about 6% by weight cannabidiol. In another embodiment, the *cannabis* oil comprises less than about 7% by weight cannabidiol. In yet another embodiment, the *cannabis* oil comprises less than about 8% by weight cannabidiol. In still another embodiment, the *cannabis* oil comprises less than about 9% by weight cannabidiol. In another embodiment, the *cannabis* oil comprises less than about 10% by weight cannabidiol.

In another embodiment, the *cannabis* oil comprises less than about 11% by weight cannabidiol. In yet another embodiment, the *cannabis* oil comprises less than about 12% by weight cannabidiol. In still another embodiment, the *cannabis* oil comprises less than about 13% by weight cannabidiol. In another embodiment, the *cannabis* oil comprises less than about 14% by weight cannabidiol. In yet another embodiment, the *cannabis* oil comprises less than about 15% by weight cannabidiol. In still another embodiment, the *cannabis* oil comprises less than about 16% by weight cannabidiol. In another embodiment, the *cannabis* oil comprises less than about 17% by weight cannabidiol. In yet another embodiment, the *cannabis* oil comprises less than about 18% by weight cannabidiol. In still another embodiment, the *cannabis* oil comprises less than about 19% by weight cannabidiol. In another embodiment, the *cannabis* oil comprises less than about 20% by weight cannabidiol.

In another embodiment, the *cannabis* oil comprises less than about 21% by weight cannabidiol. In yet another embodiment, the *cannabis* oil comprises less than about 22% by weight cannabidiol. In still another embodiment, the *cannabis* oil comprises less than about 23% by weight cannabidiol. In another embodiment, the *cannabis* oil comprises less than about 24% by weight cannabidiol. In yet another embodiment, the *cannabis* oil comprises less than about 25% by weight cannabidiol. In still another embodiment, the *cannabis* oil comprises less than about 26% by weight cannabidiol. In another embodiment, the *cannabis* oil comprises less than about 27% by weight cannabidiol. In yet another embodiment, the *cannabis* oil comprises less than about 28% by weight cannabidiol. In still another embodiment, the *cannabis* oil comprises less than about 29% by weight cannabidiol. In another embodiment, the *cannabis* oil comprises less than about 30% by weight cannabidiol.

In another embodiment, the *cannabis* oil comprises less than about 31% by weight cannabidiol. In yet another embodiment, the *cannabis* oil comprises less than about 32% by weight cannabidiol. In still another embodiment, the *cannabis* oil comprises less than about 33% by weight cannabidiol. In another embodiment, the *cannabis* oil comprises less than about 34% by weight cannabidiol. In yet another embodiment, the *cannabis* oil comprises less than about 35% by weight cannabidiol. In still another embodiment, the *cannabis* oil comprises less than about 36% by weight cannabidiol. In another embodiment, the *cannabis* oil comprises less than about 37% by weight cannabidiol. In yet another embodiment, the *cannabis* oil comprises less than about 38% by weight cannabidiol. In still another embodiment, the *cannabis* oil comprises less than about 39% by weight cannabidiol. In another embodiment, the *cannabis* oil comprises less than about 40% by weight cannabidiol.

In another embodiment, the *cannabis* oil comprises less than about 41% by weight cannabidiol. In yet another embodiment, the *cannabis* oil comprises less than about 42% by weight cannabidiol. In still another embodiment, the *cannabis* oil comprises less than about 43% by weight cannabidiol. In another embodiment, the *cannabis* oil comprises less than about 44% by weight cannabidiol. In yet another embodiment, the *cannabis* oil comprises less than about 45% by weight cannabidiol. In still another embodiment, the *cannabis* oil comprises less than about 46% by weight cannabidiol. In another embodiment, the *cannabis* oil comprises less than about 47% by weight cannabidiol. In yet another embodiment, the *cannabis* oil comprises less than about 48% by weight cannabidiol. In still another embodiment, the *cannabis* oil comprises less than about 49% by weight cannabidiol. In another embodiment, the *cannabis* oil comprises less than about 50% by weight cannabidiol.

In another embodiment, the *cannabis* oil comprises less than about 51% by weight cannabidiol. In yet another embodiment, the *cannabis* oil comprises less than about 52% by weight cannabidiol. In still another embodiment, the *cannabis* oil comprises less than about 53% by weight cannabidiol. In another embodiment, the *cannabis* oil comprises less than about 54% by weight cannabidiol. In yet another embodiment, the *cannabis* oil comprises less than about 55% by weight cannabidiol. In still another embodiment, the *cannabis* oil comprises less than about 56% by weight cannabidiol. In another embodiment, the *cannabis* oil comprises less than about 57% by weight cannabidiol. In yet another embodiment, the *cannabis* oil comprises less than about 58% by weight cannabidiol. In still another embodiment, the *cannabis* oil comprises less than about 59% by weight cannabidiol. In another embodiment, the *cannabis* oil comprises less than about 60% by weight cannabidiol.

In another embodiment, the *cannabis* oil comprises less than about 61% by weight cannabidiol. In yet another embodiment, the *cannabis* oil comprises less than about 62% by weight cannabidiol. In still another embodiment, the *cannabis* oil comprises less than about 63% by weight cannabidiol. In another embodiment, the *cannabis* oil comprises less than about 64% by weight cannabidiol. In yet another embodiment, the *cannabis* oil comprises less than about 65% by weight cannabidiol. In still another embodiment, the *cannabis* oil comprises less than about 66% by weight cannabidiol. In another embodiment, the *cannabis* oil comprises less than about 67% by weight cannabidiol. In yet another embodiment, the *cannabis* oil comprises less than about 68% by weight cannabidiol. In still another embodiment, the *cannabis* oil comprises less than about 69% by weight cannabidiol. In another embodiment, the *cannabis* oil comprises less than about 70% by weight cannabidiol.

In another embodiment, the *cannabis* oil comprises less than about 71% by weight cannabidiol. In yet another embodiment, the *cannabis* oil comprises less than about 72% by weight cannabidiol. In still another embodiment, the *cannabis* oil comprises less than about 73% by weight cannabidiol. In another embodiment, the *cannabis* oil comprises less than about 74% by weight cannabidiol. In yet another embodiment, the *cannabis* oil comprises less than about 75% by weight cannabidiol. In still another embodiment, the *cannabis* oil comprises less than about 76% by weight cannabidiol. In another embodiment, the *cannabis* oil comprises less than about 77% by weight cannabidiol. In yet another embodiment, the *cannabis* oil comprises less than about 78% by weight cannabidiol. In still another embodiment, the *cannabis* oil comprises less than about 79% by weight cannabidiol. In another embodiment, the *cannabis* oil comprises less than about 80% by weight cannabidiol.

In another embodiment, the *cannabis* oil comprises less than about 81% by weight cannabidiol. In yet another embodiment, the *cannabis* oil comprises less than about 82% by weight cannabidiol. In still another embodiment, the *cannabis* oil comprises less than about 83% by weight cannabidiol. In another embodiment, the *cannabis* oil comprises less than about 84% by weight cannabidiol. In yet another embodiment, the *cannabis* oil comprises less than about 85% by weight cannabidiol. In still another embodiment, the *cannabis* oil comprises less than about 86% by weight cannabidiol. In another embodiment, the *cannabis* oil comprises less than about 87% by weight cannabidiol. In yet another embodiment, the *cannabis* oil comprises less than about 88% by weight cannabidiol. In still another embodiment, the *cannabis* oil comprises less than about 89% by weight cannabidiol. In another embodiment, the *cannabis* oil comprises less than about 90% by weight cannabidiol.

In another embodiment, the *cannabis* oil comprises less than about 91% by weight cannabidiol. In yet another embodiment, the *cannabis* oil comprises less than about 92% by weight cannabidiol. In still another embodiment, the *cannabis* oil comprises less than about 93% by weight cannabidiol. In another embodiment, the *cannabis* oil comprises less than about 94% by weight cannabidiol. In yet another embodiment, the *cannabis* oil comprises less than about 95% by weight cannabidiol. In still another embodiment, the *cannabis* oil comprises less than about 96% by weight cannabidiol. In another embodiment, the *cannabis* oil comprises less than about 97% by weight cannabidiol. In yet another embodiment, the *cannabis* oil comprises less than about 98% by weight cannabidiol. In still another embodiment, the *cannabis* oil comprises less than about 99% by weight cannabidiol. In another embodiment, the *cannabis* oil comprises less than about 100% by weight cannabidiol.

In an embodiment, the *cannabis* oil comprises from about 0.001% to about 100% by weight Δ9-tetrahydrocannabinol. In another embodiment, the *cannabis* oil comprises from about 0.001% to about 25% by weight Δ9-tetrahydrocannabinol. In another embodiment, the *cannabis* oil comprises about 0% by weight Δ9-tetrahydrocannabinol. In another embodiment, the *cannabis* oil comprises about 0.001% by weight Δ9-tetrahydrocannabinol. In yet another embodiment, the *cannabis* oil comprises about 0.002% by weight Δ9-tetrahydrocannabinol. In still another embodiment, the *cannabis* oil comprises about 0.003% by weight Δ9-tetrahydrocannabinol. In another embodiment, the *cannabis* oil comprises about 0.004% by weight Δ9-tetrahydrocannabinol. In yet another embodiment, the *cannabis* oil comprises about 0.005% by weight Δ9-tetrahydrocannabinol. In still another embodiment, the *cannabis* oil comprises about 0.006% by weight Δ9-tetrahydrocannabinol. In another embodiment, the *cannabis* oil comprises about 0.007% by weight Δ9-tetrahydrocannabinol. In yet another embodiment, the *cannabis* oil comprises about 0.008% by weight Δ9-tetrahydrocannabinol. In still another embodiment, the *cannabis* oil comprises about 0.009% by weight Δ9-tetrahydrocannabinol.

In another embodiment, the *cannabis* oil comprises about 0.01% by weight Δ9-tetrahydrocannabinol. In yet another embodiment, the *cannabis* oil comprises about 0.02% by weight Δ9-tetrahydrocannabinol. In still another embodiment, the *cannabis* oil comprises about 0.03% by weight Δ9-tetrahydrocannabinol. In another embodiment, the *cannabis* oil comprises about 0.04% by weight Δ9-tetrahydrocannabinol. In yet another embodiment, the *cannabis* oil comprises about 0.05% by weight Δ9-tetrahydrocannabinol. In still another embodiment, the *cannabis* oil comprises about 0.06% by weight Δ9-tetrahydrocannabinol. In another embodiment, the *cannabis* oil comprises about 0.07% by weight Δ9-tetrahydrocannabinol. In yet another embodiment, the *cannabis* oil comprises about 0.08% by weight Δ9-tetrahydrocannabinol. In still another embodiment, the *cannabis* oil comprises about 0.09% by weight Δ9-tetrahydrocannabinol.

In another embodiment, the *cannabis* oil comprises about 0.1% by weight Δ9-tetrahydrocannabinol. In yet another embodiment, the *cannabis* oil comprises about 0.2% by weight Δ9-tetrahydrocannabinol. In still another embodiment, the *cannabis* oil comprises about 0.3% by weight Δ9-tetrahydrocannabinol. In another embodiment, the *cannabis* oil comprises about 0.4% by weight Δ9-tetrahydrocannabinol. In yet another embodiment, the *cannabis* oil comprises about 0.5% by weight Δ9-tetrahydrocannabinol. In still another embodiment, the *cannabis* oil comprises about 0.6% by weight Δ9-tetrahydrocannabinol. In another embodiment, the *cannabis* oil comprises about 0.7% by weight Δ9-tetrahydrocannabinol. In yet another embodiment, the *cannabis* oil comprises about 0.8% by weight Δ9-tetrahydrocannabinol. In still another embodiment, the *cannabis* oil comprises about 0.9% by weight Δ9-tetrahydrocannabinol.

In another embodiment, the *cannabis* oil comprises about 1% by weight Δ9-tetrahydrocannabinol. In yet another embodiment, the *cannabis* oil comprises about 2% by weight Δ9-tetrahydrocannabinol. In still another embodiment, the *cannabis* oil comprises about 3% by weight Δ9-tetrahydrocannabinol. In another embodiment, the *can-* nabis oil comprises about 4% by weight Δ9-tetrahydrocannabinol. In yet another embodiment, the *cannabis* oil comprises about 5% by weight Δ9-tetrahydrocannabinol. In still another embodiment, the *cannabis* oil comprises about 6% by weight Δ9-tetrahydrocannabinol. In another embodiment, the *cannabis* oil comprises about 7% by weight Δ9-tetrahydrocannabinol. In yet another embodiment, the *cannabis* oil comprises about 8% by weight Δ9-tetrahydrocannabinol. In still another embodiment, the *cannabis* oil comprises about 9% by weight Δ9-tetrahydrocannabinol. In another embodiment, the *cannabis* oil comprises about 10% by weight Δ9-tetrahydrocannabinol.

In another embodiment, the *cannabis* oil comprises about 11% by weight Δ9-tetrahydrocannabinol. In yet another embodiment, the *cannabis* oil comprises about 12% by weight Δ9-tetrahydrocannabinol. In still another embodiment, the *cannabis* oil comprises about 13% by weight Δ9-tetrahydrocannabinol. In another embodiment, the *cannabis* oil comprises about 14% by weight Δ9-tetrahydrocannabinol. In yet another embodiment, the *cannabis* oil comprises about 15% by weight Δ9-tetrahydrocannabinol. In still another embodiment, the *cannabis* oil comprises about 16% by weight Δ9-tetrahydrocannabinol. In another embodiment, the *cannabis* oil comprises about 17% by weight Δ9-tetrahydrocannabinol. In yet another embodiment, the *cannabis* oil comprises about 18% by weight Δ9-tetrahydrocannabinol. In still another embodiment, the *cannabis* oil comprises about 19% by weight Δ9-tetrahydrocannabinol. In another embodiment, the *cannabis* oil comprises about 20% by weight Δ9-tetrahydrocannabinol.

In another embodiment, the *cannabis* oil comprises about 21% by weight Δ9-tetrahydrocannabinol. In yet another embodiment, the *cannabis* oil comprises about 22% by weight Δ9-tetrahydrocannabinol. In still another embodiment, the *cannabis* oil comprises about 23% by weight Δ9-tetrahydrocannabinol. In another embodiment, the *cannabis* oil comprises about 24% by weight Δ9-tetrahydrocannabinol. In yet another embodiment, the *cannabis* oil comprises about 25% by weight Δ9-tetrahydrocannabinol. In still another embodiment, the *cannabis* oil comprises about 26% by weight Δ9-tetrahydrocannabinol. In another embodiment, the *cannabis* oil comprises about 27% by weight Δ9-tetrahydrocannabinol. In yet another embodiment, the *cannabis* oil comprises about 28% by weight Δ9-tetrahydrocannabinol. In still another embodiment, the *cannabis* oil comprises about 29% by weight Δ9-tetrahydrocannabinol. In another embodiment, the *cannabis* oil comprises about 30% by weight Δ9-tetrahydrocannabinol.

In another embodiment, the *cannabis* oil comprises about 31% by weight Δ9-tetrahydrocannabinol. In yet another embodiment, the *cannabis* oil comprises about 32% by weight Δ9-tetrahydrocannabinol. In still another embodiment, the *cannabis* oil comprises about 33% by weight Δ9-tetrahydrocannabinol. In another embodiment, the *cannabis* oil comprises about 34% by weight Δ9-tetrahydrocannabinol. In yet another embodiment, the *cannabis* oil comprises about 35% by weight Δ9-tetrahydrocannabinol. In still another embodiment, the *cannabis* oil comprises about 36% by weight Δ9-tetrahydrocannabinol. In another embodiment, the *cannabis* oil comprises about 37% by weight Δ9-tetrahydrocannabinol. In yet another embodiment, the *cannabis* oil comprises about 38% by weight Δ9-tetrahydrocannabinol. In still another embodiment, the *cannabis* oil comprises about 39% by weight Δ9-tetrahydrocannabinol. In another embodiment, the *cannabis* oil comprises about 40% by weight Δ9-tetrahydrocannabinol.

In another embodiment, the *cannabis* oil comprises about 41% by weight Δ9-tetrahydrocannabinol. In yet another embodiment, the *cannabis* oil comprises about 42% by weight Δ9-tetrahydrocannabinol. In still another embodiment, the *cannabis* oil comprises about 43% by weight Δ9-tetrahydrocannabinol. In another embodiment, the *cannabis* oil comprises about 44% by weight Δ9-tetrahydrocannabinol. In yet another embodiment, the *cannabis* oil comprises about 45% by weight Δ9-tetrahydrocannabinol. In still another embodiment, the *cannabis* oil comprises about 46% by weight Δ9-tetrahydrocannabinol. In another embodiment, the *cannabis* oil comprises about 47% by weight Δ9-tetrahydrocannabinol. In yet another embodiment, the *cannabis* oil comprises about 48% by weight Δ9-tetrahydrocannabinol. In still another embodiment, the *cannabis* oil comprises about 49% by weight Δ9-tetrahydrocannabinol. In another embodiment, the *cannabis* oil comprises about 50% by weight Δ9-tetrahydrocannabinol.

In another embodiment, the *cannabis* oil comprises about 51% by weight Δ9-tetrahydrocannabinol. In yet another embodiment, the *cannabis* oil comprises about 52% by weight Δ9-tetrahydrocannabinol. In still another embodiment, the *cannabis* oil comprises about 53% by weight Δ9-tetrahydrocannabinol. In another embodiment, the *cannabis* oil comprises about 54% by weight Δ9-tetrahydrocannabinol. In yet another embodiment, the *cannabis* oil comprises about 55% by weight Δ9-tetrahydrocannabinol. In still another embodiment, the *cannabis* oil comprises about 56% by weight Δ9-tetrahydrocannabinol. In another embodiment, the *cannabis* oil comprises about 57% by weight Δ9-tetrahydrocannabinol. In yet another embodiment, the *cannabis* oil comprises about 58% by weight Δ9-tetrahydrocannabinol. In still another embodiment, the *cannabis* oil comprises about 59% by weight Δ9-tetrahydrocannabinol. In another embodiment, the *cannabis* oil comprises about 60% by weight Δ9-tetrahydrocannabinol.

In another embodiment, the *cannabis* oil comprises about 61% by weight Δ9-tetrahydrocannabinol. In yet another embodiment, the *cannabis* oil comprises about 62% by weight Δ9-tetrahydrocannabinol. In still another embodiment, the *cannabis* oil comprises about 63% by weight Δ9-tetrahydrocannabinol. In another embodiment, the *cannabis* oil comprises about 64% by weight Δ9-tetrahydrocannabinol. In yet another embodiment, the *cannabis* oil comprises about 65% by weight Δ9-tetrahydrocannabinol. In still another embodiment, the *cannabis* oil comprises about 66% by weight Δ9-tetrahydrocannabinol. In another embodiment, the *cannabis* oil comprises about 67% by weight Δ9-tetrahydrocannabinol. In yet another embodiment, the *cannabis* oil comprises about 68% by weight Δ9-tetrahydrocannabinol. In still another embodiment, the *cannabis* oil comprises about 69% by weight Δ9-tetrahydrocannabinol. In another embodiment, the *cannabis* oil comprises about 70% by weight Δ9-tetrahydrocannabinol.

In another embodiment, the *cannabis* oil comprises about 71% by weight Δ9-tetrahydrocannabinol. In yet another embodiment, the *cannabis* oil comprises about 72% by weight Δ9-tetrahydrocannabinol. In still another embodiment, the *cannabis* oil comprises about 73% by weight Δ9-tetrahydrocannabinol. In another embodiment, the *cannabis* oil comprises about 74% by weight Δ9-tetrahydrocannabinol. In yet another embodiment, the *cannabis* oil comprises about 75% by weight Δ9-tetrahydrocannabinol. In still another embodiment, the *cannabis* oil comprises about 76% by weight Δ9-tetrahydrocannabinol. In another embodiment, the *cannabis* oil comprises about 77% by weight Δ9-tetrahydrocannabinol. In yet another embodiment, the *cannabis* oil comprises about 78% by weight Δ9-tetrahydrocannabinol. In still another embodiment, the *cannabis* oil comprises about 79% by weight Δ9-tetrahydrocannabinol. In another embodiment, the *cannabis* oil comprises about 80% by weight Δ9-tetrahydrocannabinol.

In another embodiment, the *cannabis* oil comprises about 81% by weight Δ9-tetrahydrocannabinol. In yet another embodiment, the *cannabis* oil comprises about 82% by weight Δ9-tetrahydrocannabinol. In still another embodiment, the *cannabis* oil comprises about 83% by weight Δ9-tetrahydrocannabinol. In another embodiment, the *cannabis* oil comprises about 84% by weight Δ9-tetrahydrocannabinol. In yet another embodiment, the *cannabis* oil comprises about 85% by weight Δ9-tetrahydrocannabinol. In still another embodiment, the *cannabis* oil comprises about 86% by weight Δ9-tetrahydrocannabinol. In another embodiment, the *cannabis* oil comprises about 87% by weight Δ9-tetrahydrocannabinol. In yet another embodiment, the *cannabis* oil comprises about 88% by weight Δ9-tetrahydrocannabinol. In still another embodiment, the *cannabis* oil comprises about 89% by weight Δ9-tetrahydrocannabinol. In another embodiment, the *cannabis* oil comprises about 90% by weight Δ9-tetrahydrocannabinol.

In another embodiment, the *cannabis* oil comprises about 91% by weight Δ9-tetrahydrocannabinol. In yet another embodiment, the *cannabis* oil comprises about 92% by weight Δ9-tetrahydrocannabinol. In still another embodiment, the *cannabis* oil comprises about 93% by weight Δ9-tetrahydrocannabinol. In another embodiment, the *cannabis* oil comprises about 94% by weight Δ9-tetrahydrocannabinol. In yet another embodiment, the *cannabis* oil comprises about 95% by weight Δ9-tetrahydrocannabinol. In still another embodiment, the *cannabis* oil comprises about 96% by weight Δ9-tetrahydrocannabinol. In another embodiment, the *cannabis* oil comprises about 97% by weight Δ9-tetrahydrocannabinol. In yet another embodiment, the *cannabis* oil comprises about 98% by weight Δ9-tetrahydrocannabinol. In still another embodiment, the *cannabis* oil comprises about 99% by weight Δ9-tetrahydrocannabinol. In another embodiment, the *cannabis* oil comprises about 100% by weight Δ9-tetrahydrocannabinol.

In another embodiment, the *cannabis* oil comprises less than about 0.1% by weight Δ9-tetrahydrocannabinol. In yet another embodiment, the *cannabis* oil comprises less than about 0.2% by weight Δ9-tetrahydrocannabinol. In still another embodiment, the *cannabis* oil comprises less than about 0.3% by weight Δ9-tetrahydrocannabinol. In another embodiment, the *cannabis* oil comprises less than about 0.4% by weight Δ9-tetrahydrocannabinol. In yet another embodiment, the *cannabis* oil comprises less than about 0.5% by weight Δ9-tetrahydrocannabinol. In still another embodiment, the *cannabis* oil comprises less than about 0.6% by weight Δ9-tetrahydrocannabinol. In another embodiment, the *cannabis* oil comprises less than about 0.7% by weight Δ9-tetrahydrocannabinol. In yet another embodiment, the *cannabis* oil comprises less than about 0.8% by weight Δ9-tetrahydrocannabinol. In still another embodiment, the *cannabis* oil comprises less than about 0.9% by weight Δ9-tetrahydrocannabinol.

In another embodiment, the *cannabis* oil comprises less than about 1% by weight Δ9-tetrahydrocannabinol. In yet another embodiment, the *cannabis* oil comprises less than about 2% by weight Δ9-tetrahydrocannabinol. In still another embodiment, the *cannabis* oil comprises less than about 3% by weight Δ9-tetrahydrocannabinol. In another embodiment, the *cannabis* oil comprises less than about 4% by weight Δ9-tetrahydrocannabinol. In yet another embodiment, the *cannabis* oil comprises less than about 5% by weight Δ9-tetrahydrocannabinol. In still another embodiment, the *cannabis* oil comprises less than about 6% by weight Δ9-tetrahydrocannabinol. In another embodiment, the *cannabis* oil comprises less than about 7% by weight Δ9-tetrahydrocannabinol. In yet another embodiment, the *cannabis* oil comprises less than about 8% by weight Δ9-tetrahydrocannabinol. In still another embodiment, the *cannabis* oil comprises less than about 9% by weight Δ9-tetrahydrocannabinol. In another embodiment, the *cannabis* oil comprises less than about 10% by weight Δ9-tetrahydrocannabinol.

In another embodiment, the *cannabis* oil comprises less than about 11% by weight Δ9-tetrahydrocannabinol. In yet another embodiment, the *cannabis* oil comprises less than about 12% by weight Δ9-tetrahydrocannabinol. In still another embodiment, the *cannabis* oil comprises less than about 13% by weight Δ9-tetrahydrocannabinol. In another embodiment, the *cannabis* oil comprises less than about 14% by weight Δ9-tetrahydrocannabinol. In yet another embodiment, the *cannabis* oil comprises less than about 15% by weight Δ9-tetrahydrocannabinol. In still another embodiment, the *cannabis* oil comprises less than about 16% by weight Δ9-tetrahydrocannabinol. In another embodiment, the *cannabis* oil comprises less than about 17% by weight Δ9-tetrahydrocannabinol. In yet another embodiment, the *cannabis* oil comprises less than about 18% by weight Δ9-tetrahydrocannabinol. In still another embodiment, the *cannabis* oil comprises less than about 19% by weight Δ9-tetrahydrocannabinol. In another embodiment, the *cannabis* oil comprises less than about 20% by weight Δ9-tetrahydrocannabinol.

In another embodiment, the *cannabis* oil comprises less than about 21% by weight Δ9-tetrahydrocannabinol. In yet another embodiment, the *cannabis* oil comprises less than about 22% by weight Δ9-tetrahydrocannabinol. In still another embodiment, the *cannabis* oil comprises less than about 23% by weight Δ9-tetrahydrocannabinol. In another embodiment, the *cannabis* oil comprises less than about 24% by weight Δ9-tetrahydrocannabinol. In yet another embodiment, the *cannabis* oil comprises less than about 25% by weight Δ9-tetrahydrocannabinol. In still another embodiment, the *cannabis* oil comprises less than about 26% by weight Δ9-tetrahydrocannabinol. In another embodiment, the *cannabis* oil comprises less than about 27% by weight Δ9-tetrahydrocannabinol. In yet another embodiment, the *cannabis* oil comprises less than about 28% by weight Δ9-tetrahydrocannabinol. In still another embodiment, the *cannabis* oil comprises less than about 29% by weight Δ9-tetrahydrocannabinol. In another embodiment, the *cannabis* oil comprises less than about 30% by weight Δ9-tetrahydrocannabinol.

In another embodiment, the *cannabis* oil comprises less than about 31% by weight Δ9-tetrahydrocannabinol. In yet another embodiment, the *cannabis* oil comprises less than about 32% by weight Δ9-tetrahydrocannabinol. In still another embodiment, the *cannabis* oil comprises less than about 33% by weight Δ9-tetrahydrocannabinol. In another embodiment, the *cannabis* oil comprises less than about 34% by weight Δ9-tetrahydrocannabinol. In yet another embodiment, the *cannabis* oil comprises less than about 35% by weight Δ9-tetrahydrocannabinol. In still another embodiment, the *cannabis* oil comprises less than about 36% by weight Δ9-tetrahydrocannabinol. In another embodiment, the *cannabis* oil comprises less than about 37% by weight Δ9-tetrahydrocannabinol. In yet another embodiment, the *cannabis* oil comprises less than about 38% by weight Δ9-tetrahydrocannabinol. In still another embodiment, the *cannabis* oil comprises less than about 39% by weight Δ9-tetrahydrocannabinol. In another embodiment, the *cannabis* oil comprises less than about 40% by weight Δ9-tetrahydrocannabinol.

In another embodiment, the *cannabis* oil comprises less than about 41% by weight Δ9-tetrahydrocannabinol. In yet another embodiment, the *cannabis* oil comprises less than about 42% by weight Δ9-tetrahydrocannabinol. In still another embodiment, the *cannabis* oil comprises less than about 43% by weight Δ9-tetrahydrocannabinol. In another embodiment, the *cannabis* oil comprises less than about 44% by weight Δ9-tetrahydrocannabinol. In yet another embodiment, the *cannabis* oil comprises less than about 45% by weight Δ9-tetrahydrocannabinol. In still another embodiment, the *cannabis* oil comprises less than about 46% by weight Δ9-tetrahydrocannabinol. In another embodiment, the *cannabis* oil comprises less than about 47% by weight Δ9-tetrahydrocannabinol. In yet another embodiment, the *cannabis* oil comprises less than about 48% by weight Δ9-tetrahydrocannabinol. In still another embodiment, the *cannabis* oil comprises less than about 49% by weight Δ9-tetrahydrocannabinol. In another embodiment, the *cannabis* oil comprises less than about 50% by weight Δ9-tetrahydrocannabinol.

In another embodiment, the *cannabis* oil comprises less than about 51% by weight Δ9-tetrahydrocannabinol. In yet another embodiment, the *cannabis* oil comprises less than about 52% by weight Δ9-tetrahydrocannabinol. In still another embodiment, the *cannabis* oil comprises less than about 53% by weight Δ9-tetrahydrocannabinol. In another embodiment, the *cannabis* oil comprises less than about 54% by weight Δ9-tetrahydrocannabinol. In yet another embodiment, the *cannabis* oil comprises less than about 55% by weight Δ9-tetrahydrocannabinol. In still another embodiment, the *cannabis* oil comprises less than about 56% by weight Δ9-tetrahydrocannabinol. In another embodiment, the *cannabis* oil comprises less than about 57% by weight Δ9-tetrahydrocannabinol. In yet another embodiment, the *cannabis* oil comprises less than about 58% by weight Δ9-tetrahydrocannabinol. In still another embodiment, the *cannabis* oil comprises less than about 59% by weight Δ9-tetrahydrocannabinol. In another embodiment, the *cannabis* oil comprises less than about 60% by weight Δ9-tetrahydrocannabinol.

In another embodiment, the *cannabis* oil comprises less than about 61% by weight Δ9-tetrahydrocannabinol. In yet another embodiment, the *cannabis* oil comprises less than about 62% by weight Δ9-tetrahydrocannabinol. In still another embodiment, the *cannabis* oil comprises less than about 63% by weight Δ9-tetrahydrocannabinol. In another embodiment, the *cannabis* oil comprises less than about 64% by weight Δ9-tetrahydrocannabinol. In yet another embodiment, the *cannabis* oil comprises less than about 65% by weight Δ9-tetrahydrocannabinol. In still another embodiment, the *cannabis* oil comprises less than about 66% by weight Δ9-tetrahydrocannabinol. In another embodiment, the *cannabis* oil comprises less than about 67% by weight Δ9-tetrahydrocannabinol. In yet another embodiment, the *cannabis* oil comprises less than about 68% by weight Δ9-tetrahydrocannabinol. In still another embodiment, the *cannabis* oil comprises less than about 69% by weight Δ9-tetrahydrocannabinol. In another embodiment, the *cannabis* oil comprises less than about 70% by weight Δ9-tetrahydrocannabinol.

In another embodiment, the *cannabis* oil comprises less than about 71% by weight Δ9-tetrahydrocannabinol. In yet another embodiment, the *cannabis* oil comprises less than about 72% by weight Δ9-tetrahydrocannabinol. In still another embodiment, the *cannabis* oil comprises less than about 73% by weight Δ9-tetrahydrocannabinol. In another embodiment, the *cannabis* oil comprises less than about 74% by weight Δ9-tetrahydrocannabinol. In yet another embodiment, the *cannabis* oil comprises less than about 75% by weight Δ9-tetrahydrocannabinol. In still another embodiment, the *cannabis* oil comprises less than about 76% by weight Δ9-tetrahydrocannabinol. In another embodiment, the *cannabis* oil comprises less than about 77% by weight Δ9-tetrahydrocannabinol. In yet another embodiment, the *cannabis* oil comprises less than about 78% by weight Δ9-tetrahydrocannabinol. In still another embodiment, the *cannabis* oil comprises less than about 79% by weight Δ9-tetrahydrocannabinol. In another embodiment, the *cannabis* oil comprises less than about 80% by weight Δ9-tetrahydrocannabinol.

In another embodiment, the *cannabis* oil comprises less than about 81% by weight Δ9-tetrahydrocannabinol. In yet another embodiment, the *cannabis* oil comprises less than about 82% by weight Δ9-tetrahydrocannabinol. In still another embodiment, the *cannabis* oil comprises less than about 83% by weight Δ9-tetrahydrocannabinol. In another embodiment, the *cannabis* oil comprises less than about 84% by weight Δ9-tetrahydrocannabinol. In yet another embodiment, the *cannabis* oil comprises less than about 85% by weight Δ9-tetrahydrocannabinol. In still another embodiment, the *cannabis* oil comprises less than about 86% by weight Δ9-tetrahydrocannabinol. In another embodiment, the *cannabis* oil comprises less than about 87% by weight Δ9-tetrahydrocannabinol. In yet another embodiment, the *cannabis* oil comprises less than about 88% by weight Δ9-tetrahydrocannabinol. In still another embodiment, the *cannabis* oil comprises less than about 89% by weight Δ9-tetrahydrocannabinol. In another embodiment, the *cannabis* oil comprises less than about 90% by weight Δ9-tetrahydrocannabinol.

In another embodiment, the *cannabis* oil comprises less than about 91% by weight Δ9-tetrahydrocannabinol. In yet another embodiment, the *cannabis* oil comprises less than about 92% by weight Δ9-tetrahydrocannabinol. In still another embodiment, the *cannabis* oil comprises less than about 93% by weight Δ9-tetrahydrocannabinol. In another embodiment, the *cannabis* oil comprises less than about 94% by weight Δ9-tetrahydrocannabinol. In yet another embodiment, the *cannabis* oil comprises less than about 95% by weight Δ9-tetrahydrocannabinol. In still another embodiment, the *cannabis* oil comprises less than about 96% by weight Δ9-tetrahydrocannabinol. In another embodiment, the *cannabis* oil comprises less than about 97% by weight Δ9-tetrahydrocannabinol. In yet another embodiment, the *cannabis* oil comprises less than about 98% by weight Δ9-tetrahydrocannabinol. In still another embodiment, the *cannabis* oil comprises less than about 99% by weight Δ9-tetrahydrocannabinol. In another embodiment, the *cannabis* oil comprises less than about 100% by weight Δ9-tetrahydrocannabinol.

In an embodiment, the concentration of Δ9-tetrahydrocannabinol is insufficient to produce a psychotropic effect. In an embodiment, the concentration of Δ9-tetrahydrocannabinol is less than about 2 mg/mL. In another embodiment, the concentration of Δ9-tetrahydrocannabinol is less than about 1.5 mg/mL. In yet another embodiment, the concentration of Δ9-tetrahydrocannabinol is less than about 1 mg/mL. In still another embodiment, the concentration of Δ9-tetrahydrocannabinol is less than about 0.9 mg/mL. In yet another embodiment, the concentration of Δ9-tetrahydrocannabinol is less than about 0.8 mg/mL. In an embodiment, the concentration of Δ9-tetrahydrocannabinol is less than about 0.7 mg/mL. In another embodiment, the concentration of Δ9-tetrahydrocannabinol is less than about 0.6 mg/mL. In yet another embodiment, the concentration of Δ9-tetrahydrocannabinol is less than about 0.5 mg/mL. In still another embodiment, the concentration of Δ9-tetrahydrocannabinol is less than about 0.4 mg/mL. In an embodiment, the concentration of Δ9-tetrahydrocannabinol is less than about 0.3 mg/mL. In another embodiment, the concentration of Δ9-tetrahydrocannabinol is less than about 0.2 mg/mL. In yet another embodiment, the concentration of Δ9-tetrahydrocannabinol is less than about 0.1 mg/mL. In another embodiment, the concentration of Δ9-tetrahydrocannabinol is about 0 mg/mL.

In an embodiment, the ratio of Δ9-tetrahydrocannabinol to cannabidiol in the *cannabis* about oil is about 99:1 by weight. In another embodiment, the ratio of Δ9-tetrahydrocannabinol to cannabidiol in the *cannabis* about oil is about 95:5 by weight. In yet another embodiment, the ratio of Δ9-tetrahydrocannabinol to cannabidiol in the *cannabis* about oil is about 90:10 by weight. In still another embodiment, the ratio of Δ9-tetrahydrocannabinol to cannabidiol in the *cannabis* about oil is about 85:15 by weight. In another embodiment, the ratio of Δ9-tetrahydrocannabinol to cannabidiol in the *cannabis* about oil is about 80:20 by weight. In yet another embodiment, the ratio of Δ9-tetrahydrocannabinol to cannabidiol in the *cannabis* about oil is about 75:25 by weight. In still another embodiment, the ratio of Δ9-tetrahydrocannabinol to cannabidiol in the *cannabis* about oil is about 70:30 by weight.

In another embodiment, the ratio of Δ9-tetrahydrocannabinol to cannabidiol in the *cannabis* about oil is about 65:35 by weight. In yet another embodiment, the ratio of Δ9-tetrahydrocannabinol to cannabidiol in the *cannabis* about oil is about 60:40 by weight. In still another embodiment, the ratio of Δ9-tetrahydrocannabinol to cannabidiol in the *cannabis* about oil is about 55:45 by weight. In another embodiment, the ratio of Δ9-tetrahydrocannabinol to cannabidiol in the *cannabis* about oil is about 50:50 by weight. In yet another embodiment, the ratio of Δ9-tetrahydrocannabinol to cannabidiol in the *cannabis* about oil is about 45:55 by weight. In still another embodiment, the ratio of Δ9-tetrahydrocannabinol to cannabidiol in the *cannabis* about oil is about 40:60 by weight.

In another embodiment, the ratio of Δ9-tetrahydrocannabinol to cannabidiol in the *cannabis* about oil is about 35:65 by weight. In yet another embodiment, the ratio of Δ9-tetrahydrocannabinol to cannabidiol in the *cannabis* about oil is about 30:70 by weight. In still another embodiment, the ratio of Δ9-tetrahydrocannabinol to cannabidiol in the *cannabis* about oil is about 25:75 by weight. In another embodiment, the ratio of Δ9-tetrahydrocannabinol to cannabidiol in the *cannabis* about oil is about 20:80 by weight. In yet another embodiment, the ratio of Δ9-tetrahydrocannabinol to cannabidiol in the *cannabis* about oil is about 15:85 by weight. In still another embodiment, the ratio of Δ9-tetrahydrocannabinol to cannabidiol in the *cannabis* about oil is about 10:90 by weight. In another embodiment, the ratio of Δ9-tetrahydrocannabinol to cannabidiol in the *cannabis* about oil is about 5:95 by weight. In yet another embodiment, the ratio of Δ9-tetrahydrocannabinol to cannabidiol in the *cannabis* about oil is about 1:99 by weight. In an embodiment, the balance of the mixture comprises about 0.001% by weight *Capsicum frutescens* fruit extract. In another embodiment, the balance of the mixture comprises about 0.002% by weight *Capsicum frutescens* fruit extract. In yet another embodiment, the balance of the mixture comprises about 0.003% by weight *Capsicum frutescens* fruit extract. In still another embodiment, the balance of the mixture comprises about 0.004% by weight *Capsicum frutescens* fruit extract. In another embodiment, the balance of the mixture comprises about 0.005% by weight *Capsicum frutescens* fruit extract. In yet another embodiment, the balance of the mixture comprises about 0.006% by weight *Capsicum frutescens* fruit extract. In still another embodiment, the balance of the mixture comprises about 0.007% by weight *Capsicum frutescens* fruit extract. In another embodiment, the balance of the mixture comprises about 0.008% by weight *Capsicum frutescens* fruit extract. In yet another embodiment, the balance of the mixture comprises about 0.009% by weight *Capsicum frutescens* fruit extract.

In an embodiment, the balance of the mixture comprises about 0.5% by weight of a mixture consisting essentially of *chondrus* corpus extract and sodium hyaluronate. In another embodiment, the balance of the mixture comprises about 0.6% by weight of a mixture consisting essentially of *chondrus* corpus extract and sodium hyaluronate. In yet another embodiment, the balance of the mixture comprises about 0.7% by weight of a mixture consisting essentially of *chondrus* corpus extract and sodium hyaluronate. In still another embodiment, the balance of the mixture comprises about 0.8% by weight of a mixture consisting essentially of *chondrus* corpus extract and sodium hyaluronate. In another embodiment, the balance of the mixture comprises about 0.9% by weight of a mixture consisting essentially of *chondrus* corpus extract and sodium hyaluronate. In yet another embodiment, the balance of the mixture comprises about 1% by weight of a mixture consisting essentially of *chondrus* corpus extract and sodium hyaluronate. In still another embodiment, the balance of the mixture comprises about 2% by weight of a mixture consisting essentially of *chondrus* corpus extract and sodium hyaluronate. In another embodiment, the balance of the mixture comprises about 3% by weight of a mixture consisting essentially of *chondrus* corpus extract and sodium hyaluronate. In yet another embodiment, the balance of the mixture comprises about 4% by weight of a mixture consisting essentially of *chondrus* corpus extract and sodium hyaluronate. In still another embodiment, the balance of the mixture comprises about 5% by weight of a mixture consisting essentially of *chondrus* corpus extract and sodium hyaluronate.

In an embodiment, the balance of the mixture comprises about 0.1% by weight *citrus paradisi* oil. In another embodiment, the balance of the mixture comprises about 0.2% by weight *Citrus paradisi* oil. In yet another embodiment, the balance of the mixture comprises about 0.3% by weight *Citrus paradisi* oil. In still another embodiment, the balance of the mixture comprises about 0.4% by weight *Citrus paradisi* oil. In another embodiment, the balance of the mixture comprises about 0.5% by weight *Citrus paradisi* oil. In yet another embodiment, the balance of the mixture comprises about 0.6% by weight *Citrus paradisi* oil. In still another embodiment, the balance of the mixture comprises about 0.7% by weight *Citrus paradisi* oil. In another embodiment, the balance of the mixture comprises about 0.8% by weight *Citrus paradisi* oil. In yet another embodiment, the balance of the mixture comprises about 0.9% by weight *citrus paradisi* oil.

In an embodiment, the balance of the mixture comprises about 0.05% by weight *Corynanthe yohimbe* extract. In another embodiment, the balance of the mixture comprises about 0.06% by weight *Corynanthe yohimbe* extract. In yet another embodiment, the balance of the mixture comprises about 0.07% by weight *Corynanthe yohimbe* extract. In still another embodiment, the balance of the mixture comprises about 0.08% by weight *Corynanthe yohimbe* extract. In another embodiment, the balance of the mixture comprises about 0.09% by weight *Corynanthe yohimbe* extract. In yet another embodiment, the balance of the mixture comprises about 0.1% by weight *Corynanthe yohimbe* extract. In still another embodiment, the balance of the mixture comprises about 0.15% by weight *Corynanthe yohimbe* extract. In another embodiment, the balance of the mixture comprises about 0.2% by weight *Corynanthe yohimbe* extract. In yet another embodiment, the balance of the mixture comprises about 0.25% by weight *Corynanthe yohimbe* extract.

In an embodiment, the balance of the mixture comprises about 0.05% by weight of a mixture consisting essentially of glycerin, water, butylene glycol, carbomer, polysorbate 20, palmitoyl oligopeptide, and palmitoyl tetrapeptide-7. In another embodiment, the balance of the mixture comprises about 0.06% by weight of a mixture consisting essentially of glycerin, water, butylene glycol, carbomer, polysorbate 20, palmitoyl oligopeptide, and palmitoyl tetrapeptide-7. In yet another embodiment, the balance of the mixture comprises about 0.07% by weight of a mixture consisting essentially of glycerin, water, butylene glycol, carbomer, polysorbate 20, palmitoyl oligopeptide, and palmitoyl tetrapeptide-7. In still another embodiment, the balance of the mixture comprises about 0.08% by weight of a mixture consisting essentially of glycerin, water, butylene glycol, carbomer, polysorbate 20, palmitoyl oligopeptide, and palmitoyl tetrapeptide-7. In another embodiment, the balance of the mixture comprises about 0.09% by weight of a mixture consisting essentially of glycerin, water, butylene glycol, carbomer, polysorbate 20, palmitoyl oligopeptide, and palmitoyl tetrapeptide-7. In yet another embodiment, the balance of the mixture comprises about 0.1% by weight of a mixture consisting essentially of glycerin, water, butylene glycol, carbomer, polysorbate 20, palmitoyl oligopeptide, and palmitoyl tetrapeptide-7. In still another embodiment, the balance of the mixture comprises about 0.15% by weight of a mixture consisting essentially of glycerin, water, butylene glycol, carbomer, polysorbate 20, palmitoyl oligopeptide, and palmitoyl tetrapeptide-7. In another embodiment, the balance of the mixture comprises about 0.2% by weight of a mixture consisting essentially of glycerin, water, butylene glycol, carbomer, polysorbate 20, palmitoyl oligopeptide, and palmitoyl tetrapeptide-7. In yet another embodiment, the balance of the mixture comprises about 0.25% by weight of a mixture consisting essentially of glycerin, water, butylene glycol, carbomer, polysorbate 20, palmitoyl oligopeptide, and palmitoyl tetrapeptide-7.

In an embodiment, the balance of the mixture comprises about 0.05% by weight glycolic acid. In another embodiment, the balance of the mixture comprises about 0.06% by weight glycolic acid. In yet another embodiment, the balance of the mixture comprises about 0.07% by weight glycolic acid. In still another embodiment, the balance of the mixture comprises about 0.08% by weight glycolic acid. In another embodiment, the balance of the mixture comprises about 0.09% by weight glycolic acid. In yet another embodiment, the balance of the mixture comprises about 0.1% by weight glycolic acid. In still another embodiment, the balance of the mixture comprises about 0.15% by weight glycolic acid. In another embodiment, the balance of the mixture comprises about 0.2% by weight glycolic acid. In yet another embodiment, the balance of the mixture comprises about 0.25% by weight glycolic acid.

In an embodiment, the balance of the mixture comprises about 0.05% by weight *Glycyrrhiza glabra* root extract. In another embodiment, the balance of the mixture comprises about 0.06% by weight *Glycyrrhiza glabra* root extract. In yet another embodiment, the balance of the mixture comprises about 0.07% by weight *Glycyrrhiza glabra* root extract. In still another embodiment, the balance of the mixture comprises about 0.08% by weight *Glycyrrhiza glabra* root extract. In another embodiment, the balance of the mixture comprises about 0.09% by weight *Glycyrrhiza glabra* root extract. In yet another embodiment, the balance of the mixture comprises about 0.1% by weight *Glycyrrhiza glabra* root extract. In still another embodiment, the balance of the mixture comprises about 0.15% by weight *Glycyrrhiza glabra* root extract. In another embodiment, the balance of the mixture comprises about 0.2% by weight *Glycyrrhiza glabra* root extract. In yet another embodiment, the balance of the mixture comprises about 0.25% by weight *Glycyrrhiza glabra* root extract.

In an embodiment, the balance of the mixture comprises about 0.05% by weight of a mixture consisting essentially of *Helianthis annuus* seed oil and *Rosmarinus officianalis* leaf extract. In another embodiment, the balance of the mixture comprises about 0.1% by weight of a mixture consisting essentially of *Helianthis annuus* seed oil and *Rosmarinus officianalis* leaf extract. In yet another embodiment, the balance of the mixture comprises about 0.15% by weight of a mixture consisting essentially of *Helianthis annuus* seed oil and *Rosmarinus officianalis* leaf extract. In still another embodiment, the balance of the mixture comprises about 0.2% by weight of a mixture consisting essentially of *Helianthis annuus* seed oil and *Rosmarinus officianalis* leaf extract. In another embodiment, the balance of the mixture comprises about 0.25% by weight of a mixture consisting essentially of *Helianthis annuus* seed oil and *Rosmarinus officianalis* leaf extract. In yet another embodiment, the balance of the mixture comprises about 0.3% by weight of a mixture consisting essentially of *Helianthis annuus* seed oil and *Rosmarinus officianalis* leaf extract. In still another embodiment, the balance of the mixture comprises about 0.35% by weight of a mixture consisting essentially of *Helianthis annuus* seed oil and *Rosmarinus officianalis* leaf extract. In another embodiment, the balance of the mixture comprises about 0.4% by weight of a mixture consisting essentially of *Helianthis annuus* seed oil and *Rosmarinus officianalis* leaf extract. In yet another embodiment, the balance of the mixture comprises about 0.45% by weight of a mixture consisting essentially of *Helianthis annuus* seed oil and *Rosmarinus officianalis* leaf extract.

In an embodiment, the balance of the mixture comprises about 0.001% by weight hexapeptide 30. In another embodiment, the balance of the mixture comprises about 0.002% by weight hexapeptide 30. In yet another embodiment, the balance of the mixture comprises about 0.003% by weight hexapeptide 30. In still another embodiment, the balance of the mixture comprises about 0.004% by weight hexapeptide 30. In another embodiment, the balance of the mixture comprises about 0.005% by weight hexapeptide 30. In yet another embodiment, the balance of the mixture comprises about 0.006% by weight hexapeptide 30. In still another embodiment, the balance of the mixture comprises about 0.007% by weight hexapeptide 30. In another embodiment, the balance of the mixture comprises about 0.008% by weight hexapeptide 30. In yet another embodiment, the balance of the mixture comprises about 0.009% by weight hexapeptide 30.

In an embodiment, the balance of the mixture comprises about 0.001% by weight hexapeptide 8. In another embodiment, the balance of the mixture comprises about 0.002% by weight hexapeptide 8. In yet another embodiment, the balance of the mixture comprises about 0.003% by weight hexapeptide 8. In still another embodiment, the balance of the mixture comprises about 0.004% by weight hexapeptide 8. In another embodiment, the balance of the mixture comprises about 0.005% by weight hexapeptide 8. In yet another embodiment, the balance of the mixture comprises about 0.006% by weight hexapeptide 8. In still another embodiment, the balance of the mixture comprises about 0.007% by weight hexapeptide 8. In another embodiment, the balance of the mixture comprises about 0.008% by weight hexapeptide 8. In yet another embodiment, the balance of the mixture comprises about 0.009% by weight hexapeptide 8.

In an embodiment, the balance of the mixture comprises about 0.5% by weight *Laminaria japonica* extract. In another embodiment, the balance of the mixture comprises about 0.6% by weight *Laminaria japonica* extract. In yet another embodiment, the balance of the mixture comprises about 0.7% by weight *Laminaria japonica* extract. In still another embodiment, the balance of the mixture comprises about 0.8% by weight *Laminaria japonica* extract. In another embodiment, the balance of the mixture comprises about 0.9% by weight *Laminaria japonica* extract. In yet another embodiment, the balance of the mixture comprises about 1% by weight *Laminaria japonica* extract. In still another embodiment, the balance of the mixture comprises about 1.5% by weight *Laminaria japonica* extract. In another embodiment, the balance of the mixture comprises about 2% by weight *Laminaria japonica* extract. In yet another embodiment, the balance of the mixture comprises about 2.5% by weight *Laminaria japonica* extract.

In an embodiment, the balance of the mixture comprises about 0.001% by weight *Melaluca alternifolia* leaf oil. In another embodiment, the balance of the mixture comprises about 0.002% by weight *Melaluca alternifolia* leaf oil. In yet another embodiment, the balance of the mixture comprises about 0.003% by weight *Melaluca alternifolia* leaf oil. In still another embodiment, the balance of the mixture comprises about 0.004% by weight *Melaluca alternifolia* leaf oil. In another embodiment, the balance of the mixture comprises about 0.005% by weight *Melaluca alternifolia* leaf oil. In yet another embodiment, the balance of the mixture comprises about 0.006% by weight *Melaluca alternifolia* leaf oil. In still another embodiment, the balance of the mixture comprises about 0.007% by weight *Melaluca alternifolia* leaf oil. In another embodiment, the balance of the mixture comprises about 0.008% by weight *Melaluca alternifolia* leaf oil. In yet another embodiment, the balance of the mixture comprises about 0.009% by weight *Melaluca alternifolia* leaf oil.

In an embodiment, the balance of the mixture comprises about 0.05% by weight *Mentha piperita* leaf oil. In another embodiment, the balance of the mixture comprises about 0.06% by weight *Mentha piperita* leaf oil. In yet another embodiment, the balance of the mixture comprises about 0.07% by weight *Mentha piperita* leaf oil. In still another embodiment, the balance of the mixture comprises about 0.08% by weight *Mentha piperita* leaf oil. In another embodiment, the balance of the mixture comprises about 0.09% by weight *Mentha piperita* leaf oil. In yet another embodiment, the balance of the mixture comprises about 0.1% by weight *Mentha piperita* leaf oil. In still another embodiment, the balance of the mixture comprises about 0.15% by weight *Mentha piperita* leaf oil. In another embodiment, the balance of the mixture comprises about 0.2% by weight *Mentha piperita* leaf oil. In yet another embodiment, the balance of the mixture comprises about 0.25% by weight *Mentha piperita* leaf oil.

In an embodiment, the balance of the mixture comprises about 0.1% by weight of a mixture consisting essentially of menthol and menthyl lactate. In another embodiment, the balance of the mixture comprises about 0.2% by weight of a mixture consisting essentially of menthol and menthyl lactate. In yet another embodiment, the balance of the mixture comprises about 0.3% by weight of a mixture consisting essentially of menthol and menthyl lactate. In still another embodiment, the balance of the mixture comprises about 0.4% by weight of a mixture consisting essentially of menthol and menthyl lactate. In another embodiment, the balance of the mixture comprises about 0.5% by weight of a mixture consisting essentially of menthol and menthyl lactate. In yet another embodiment, the balance of the mixture comprises about 0.6% by weight of a mixture consisting essentially of menthol and menthyl lactate. In still another embodiment, the balance of the mixture comprises about 0.7% by weight of a mixture consisting essentially of menthol and menthyl lactate. In another embodiment, the balance of the mixture comprises about 0.8% by weight of a mixture consisting essentially of menthol and menthyl lactate. In yet another embodiment, the balance of the mixture comprises about 0.9% by weight of a mixture consisting essentially of menthol and menthyl lactate.

In an embodiment, the balance of the mixture comprises about 0.001% by weight *Oenothera biennis* oil. In another embodiment, the balance of the mixture comprises about 0.002% by weight *Oenothera biennis* oil. In yet another embodiment, the balance of the mixture comprises about 0.003% by weight *Oenothera biennis* oil. In still another embodiment, the balance of the mixture comprises about 0.004% by weight *Oenothera biennis* oil. In another embodiment, the balance of the mixture comprises about 0.005% by weight *Oenothera biennis* oil. In yet another embodiment, the balance of the mixture comprises about 0.006% by weight *Oenothera biennis* oil. In still another embodiment, the balance of the mixture comprises about 0.007% by weight *Oenothera biennis* oil. In another embodiment, the balance of the mixture comprises about 0.008% by weight *Oenothera biennis* oil. In yet another embodiment, the balance of the mixture comprises about 0.009% by weight *Oenothera biennis* oil.

In an embodiment, the balance of the mixture comprises about 0.05% by weight *Persea gratissima* oil. In another embodiment, the balance of the mixture comprises about 0.06% by weight *Persea gratissima* oil. In yet another embodiment, the balance of the mixture comprises about 0.07% by weight *Persea gratissima* oil. In still another embodiment, the balance of the mixture comprises about 0.08% by weight *Persea gratissima* oil. In another embodiment, the balance of the mixture comprises about 0.09% by weight *Persea gratissima* oil. In yet another embodiment, the balance of the mixture comprises about 0.1% by weight *Persea gratissima* oil.

In still another embodiment, the balance of the mixture comprises about 0.125% by weight *Persea gratissima* oil. In another embodiment, the balance of the mixture comprises about 0.15% by weight *Persea gratissima* oil. In yet another embodiment, the balance of the mixture comprises about 0.2% by weight *Persea gratissima* oil. In still another embodiment, the balance of the mixture comprises about 0.25% by weight *Persea gratissima* oil.

In an embodiment, the balance of the mixture comprises about 0.1% by weight of a mixture consisting essentially of *Physalis angulata* extract and capyrylic/capric triglycerides. In another embodiment, the balance of the mixture comprises about 0.2% by weight of a mixture consisting essentially of *Physalis angulata* extract and capyrylic/capric triglycerides. In yet another embodiment, the balance of the mixture comprises about 0.3% by weight of a mixture consisting essentially of *Physalis angulata* extract and capyrylic/capric triglycerides. In still another embodiment, the balance of the mixture comprises about 0.4% by weight of a mixture consisting essentially of *Physalis angulata* extract and capyrylic/capric triglycerides. In another embodiment, the balance of the mixture comprises about 0.5% by weight of a mixture consisting essentially of *Physalis angulata* extract and capyrylic/capric triglycerides. In yet another embodiment, the balance of the mixture comprises about 0.6% by weight of a mixture consisting essentially of *Physalis angulata* extract and capyrylic/capric triglycerides. In still another embodiment, the balance of the mixture comprises about 0.7% by weight of a mixture consisting essentially of *Physalis angulata* extract and capyrylic/capric triglycerides. In another embodiment, the balance of the mixture comprises about 0.8% by weight of a mixture consisting essentially of *Physalis angulata* extract and capyrylic/capric triglycerides. In yet another embodiment, the balance of the mixture comprises about 0.9% by weight of a mixture consisting essentially of *Physalis angulata* extract and capyrylic/capric triglycerides.

In an embodiment, the balance of the mixture comprises about 0.05% by weight *Pinus pinaster* bark extract. In another embodiment, the balance of the mixture comprises about 0.06% by weight *Pinus pinaster* bark extract. In yet another embodiment, the balance of the mixture comprises about 0.07% by weight *Pinus pinaster* bark extract. In still another embodiment, the balance of the mixture comprises about 0.08% by weight *Pinus pinaster* bark extract. In another embodiment, the balance of the mixture comprises about 0.09% by weight *Pinus pinaster* bark extract. In yet another embodiment, the balance of the mixture comprises about 0.1% by weight *Pinus pinaster* bark extract. In still another embodiment, the balance of the mixture comprises about 0.15% by weight *Pinus pinaster* bark extract. In another embodiment, the balance of the mixture comprises about 0.2% by weight *Pinus pinaster* bark extract. In yet another embodiment, the balance of the mixture comprises about 0.25% by weight *Pinus pinaster* bark extract.

In an embodiment, the balance of the mixture comprises about 0.001% by weight *Salix alba* bark extract. In another embodiment, the balance of the mixture comprises about 0.002% by weight *Salix alba* bark extract. In yet another embodiment, the balance of the mixture comprises about 0.003% by weight *Salix alba* bark extract. In still another embodiment, the balance of the mixture comprises about 0.004% by weight *Salix alba* bark extract. In another embodiment, the balance of the mixture comprises about 0.005% by weight *Salix alba* bark extract. In yet another embodiment, the balance of the mixture comprises about 0.006% by weight *Salix alba* bark extract. In still another embodiment, the balance of the mixture comprises about 0.007% by weight *Salix alba* bark extract. In another embodiment, the balance of the mixture comprises about 0.008% by weight *Salix alba* bark extract. In yet another embodiment, the balance of the mixture comprises about 0.009% by weight *Salix alba* bark extract.

In an embodiment, the balance of the mixture comprises about 0.5% by weight *Simmondsia chinensis* seed oil. In another embodiment, the balance of the mixture comprises about 0.6% by weight *Simmondsia chinensis* seed oil. In yet another embodiment, the balance of the mixture comprises about 0.7% by weight *Simmondsia chinensis* seed oil. In still another embodiment, the balance of the mixture comprises about 0.8% by weight *Simmondsia chinensis* seed oil. In another embodiment, the balance of the mixture comprises about 0.9% by weight *Simmondsia chinensis* seed oil. In yet another embodiment, the balance of the mixture comprises about 1% by weight *Simmondsia chinensis* seed oil. In still another embodiment, the balance of the mixture comprises about 1.5% by weight *Simmondsia chinensis* seed oil. In another embodiment, the balance of the mixture comprises about 2% by weight *Simmondsia chinensis* seed oil. In yet another embodiment, the balance of the mixture comprises about 2.5% by weight *Simmondsia chinensis* seed oil.

In an embodiment, the balance of the mixture comprises about 0.05% by weight *Tanacetum parthenium*. In another embodiment, the balance of the mixture comprises about 0.06% by weight *Tanacetum parthenium*. In yet another embodiment, the balance of the mixture comprises about 0.07% by weight *Tanacetum parthenium*. In still another embodiment, the balance of the mixture comprises about 0.08% by weight *Tanacetum parthenium*. In another embodiment, the balance of the mixture comprises about 0.09% by weight *Tanacetum parthenium*. In yet another embodiment, the balance of the mixture comprises about 0.1% by weight *Tanacetum parthenium*. In still another embodiment, the balance of the mixture comprises about 0.15% by weight *Tanacetum parthenium*. In another embodiment, the balance of the mixture comprises about 0.2% by weight *Tanacetum parthenium*. In yet another embodiment, the balance of the mixture comprises about 0.25% by weight *Tanacetum parthenium*.

In an embodiment, the balance of the mixture comprises about 0.05% by weight tocopherol. In another embodiment, the balance of the mixture comprises about 0.06% by weight tocopherol. In yet another embodiment, the balance of the mixture comprises about 0.07% by weight tocopherol. In still another embodiment, the balance of the mixture comprises about 0.08% by weight tocopherol. In another embodiment, the balance of the mixture comprises about 0.09% by weight tocopherol. In yet another embodiment, the balance of the mixture comprises about 0.1% by weight tocopherol. In still another embodiment, the balance of the mixture comprises about 0.15% by weight tocopherol. In another embodiment, the balance of the mixture comprises about 0.2% by weight tocopherol. In yet another embodiment, the balance of the mixture comprises about 0.25% by weight tocopherol.

In an embodiment, the balance of the mixture comprises about 0.5% by weight urea. In another embodiment, the balance of the mixture comprises about 0.6% by weight urea. In yet another embodiment, the balance of the mixture comprises about 0.7% by weight urea. In still another embodiment, the balance of the mixture comprises about 0.8% by weight urea. In another embodiment, the balance of the mixture comprises about 0.9% by weight urea. In yet another embodiment, the balance of the mixture comprises about 1% by weight urea. In still another embodiment, the balance of the mixture comprises about 1.5% by weight urea. In another embodiment, the balance of the mixture comprises about 2% by weight urea. In yet another embodiment, the balance of the mixture comprises about 2.5% by weight urea.

In an embodiment, the balance of the mixture comprises about 0.05% by weight *valerian officinalis* extract. In another embodiment, the balance of the mixture comprises about 0.06% by weight *Valerian officinalis* extract. In yet another embodiment, the balance of the mixture comprises about 0.07% by weight *Valerian officinalis* extract. In still another embodiment, the balance of the mixture comprises about 0.08% by weight *Valerian officinalis* extract. In another embodiment, the balance of the mixture comprises about 0.09% by weight *Valerian officinalis* extract. In yet another embodiment, the balance of the mixture comprises about 0.1% by weight *Valerian officinalis* extract. In still another embodiment, the balance of the mixture comprises about 0.15% by weight *Valerian officinalis* extract. In another embodiment, the balance of the mixture comprises about 0.2% by weight *Valerian officinalis* extract. In yet another embodiment, the balance of the mixture comprises about 0.25% by weight *Valerian officinalis* extract.

In an embodiment, the balance of the mixture comprises about 0.1% by weight of a mixture consisting essentially of water, butylene glycol, dextran, and palmitoyl tripeptide-9. In another embodiment, the balance of the mixture comprises about 0.2% by weight of a mixture consisting essentially of water, butylene glycol, dextran, and palmitoyl tripeptide-9. In yet another embodiment, the balance of the mixture comprises about 0.3% by weight of a mixture consisting essentially of water, butylene glycol, dextran, and palmitoyl tripeptide-9. In still another embodiment, the balance of the mixture comprises about 0.4% by weight of a mixture consisting essentially of water, butylene glycol, dextran, and palmitoyl tripeptide-9. In another embodiment, the balance of the mixture comprises about 0.5% by weight of a mixture consisting essentially of water, butylene glycol, dextran, and palmitoyl tripeptide-9. In yet another embodiment, the balance of the mixture comprises about 0.6% by weight of a mixture consisting essentially of water, butylene glycol, dextran, and palmitoyl tripeptide-9. In still another embodiment, the balance of the mixture comprises about 0.7% by weight of a mixture consisting essentially of water, butylene glycol, dextran, and palmitoyl tripeptide-9. In another embodiment, the balance of the mixture comprises about 0.8% by weight of a mixture consisting essentially of water, butylene glycol, dextran, and palmitoyl tripeptide-9. In yet another embodiment, the balance of the mixture comprises about 0.9% by weight of a mixture consisting essentially of water, butylene glycol, dextran, and palmitoyl tripeptide-9.

In an embodiment, the balance of the mixture comprises about 0.05% by weight xanthan gum. In another embodiment, the balance of the mixture comprises about 0.1% by weight xanthan gum. In yet another embodiment, the balance of the mixture comprises about 0.15% by weight xanthan gum. In still another embodiment, the balance of the mixture comprises about 0.2% by weight xanthan gum. In another embodiment, the balance of the mixture comprises about 0.25% by weight xanthan gum. In yet another embodiment, the balance of the mixture comprises about 0.3% by weight xanthan gum. In still another embodiment, the balance of the mixture comprises about 0.35% by weight xanthan gum. In another embodiment, the balance of the mixture comprises about 0.4% by weight xanthan gum. In yet another embodiment, the balance of the mixture comprises about 0.45% by weight xanthan gum.

In an embodiment, the balance of the mixture comprises about 0.05% by weight *Euphausia superba* oil. In another embodiment, the balance of the mixture comprises about 0.06% by weight *Euphausia superba* oil. In yet another embodiment, the balance of the mixture comprises about 0.07% by weight *Euphausia superba* oil. In still another embodiment, the balance of the mixture comprises about 0.08% by weight *Euphausia superba* oil. In another embodiment, the balance of the mixture comprises about 0.09% by weight *Euphausia superba* oil. In yet another embodiment, the balance of the mixture comprises about 0.1% by weight *Euphausia superba* oil. In still another embodiment, the balance of the mixture comprises about 0.15% by weight *Euphausia superba* oil. In another embodiment, the balance of the mixture comprises about 0.2% by weight *Euphausia superba* oil. In yet another embodiment, the balance of the mixture comprises about 0.25% by weight *Euphausia superba* oil.

In an embodiment, the balance of the mixture comprises about 0.05% by weight *Cimicifuga racemosa* root extract. In another embodiment, the balance of the mixture comprises about 0.06% by weight *Cimicifuga racemosa* root extract. In yet another embodiment, the balance of the mixture comprises about 0.07% by weight *Cimicifuga racemosa* root extract. In still another embodiment, the balance of the mixture comprises about 0.08% by weight *Cimicifuga racemosa* root extract. In another embodiment, the balance of the mixture comprises about 0.09% by weight *Cimicifuga racemosa* root extract. In yet another embodiment, the balance of the mixture comprises about 0.1% by weight *Cimicifuga racemosa* root extract. In still another embodiment, the balance of the mixture comprises about 0.15% by weight *Cimicifuga racemosa* root extract. In another embodiment, the balance of the mixture comprises about 0.2% by weight *Cimicifuga racemosa* root extract. In yet another embodiment, the balance of the mixture comprises about 0.25% by weight *Cimicifuga racemosa* root extract.

In an embodiment, the balance of the mixture comprises at least one component selected from the group consisting of:

about 0.001% by weight amni *visnaga* oil;

about 0.001% by weight of a mixture consisting essentially of *Petasites japonicus* root extract and water;

about 0.001% by weight arginine;

about 0.001% by weight bentofiamine;

about 0.1% by weight of a mixture consisting essentially of butylene glycol, cetyl hydroxyethylcellulose, rutin, palmitoyl tripeptide-1, palmitoyl tetrapeptide-7, *Phaseolus lunatus* seed extract, and water;

about 0.125% by weight of a component selected from the group consisting of *cannabis* oil, cannabidiol, Δ9-tetrahydrocannabinol, cannabinol, cannabigerol, cannabidiolic acid, tetrahydrocannabinolic acid, cannabigerolic acid, and cannabichromene;

about 0.001% by weight *Capsicum frutescens* fruit extract;

about 1% by weight of a mixture consisting essentially of *chondrus corpus* extract and sodium hyaluronate;

about 0.5% by weight *Citrus paradisi* oil;

about 0.1% by weight *Corynanthe yohimbe* extract;

about 0.1% by weight of a mixture consisting essentially of glycerin, water, butylene glycol, carbomer, polysorbate 20, palmitoyl oligopeptide, and palmitoyl tetrapeptide-7;

about 0.1% by weight glycolic acid;

about 0.1% by weight *Glycyrrhiza glabra* root extract;

about 0.2% by weight of a mixture consisting essentially of *Helianthis annuus* seed oil and *Rosmarinus officianalis* leaf extract;

about 0.001% by weight hexapeptide 30;

about 0.001% by weight hexapeptide 8;

about 1% by weight of *Laminaria japonica* extract;

about 0.001% by weight *Melaluca alternifolia* leaf oil;

about 0.1% by weight *Mentha piperita* leaf oil;

about 0.5% by weight of a mixture consisting essentially of menthol and menthyl lactate;
about 0.001% by weight *Oenothera biennis* oil;
about 0.125% by weight *Persea gratissima* oil;
about 0.5% by weight of a mixture consisting essentially of *Physalis angulata* extract and capyrylic/capric triglycerides;
about 0.1% by weight *Pinus pinaster* bark extract;
about 0.001% by weight *Salix alba* bark extract;
about 1% by weight *Simmondsia chinensis* seed oil;
about 0.1% by weight *Tanacetum parthenium*;
about 0.1% by weight tocopherol;
about 1% by weight urea;
about 0.1% by weight *Valerian officinalis* extract;
about 0.3% by weight of a mixture consisting essentially of water, butylene glycol, dextran, and palmitoyl tripeptide-9;
about 0.25% by weight xanthan gum; and
water.

In an embodiment, the balance of the mixture comprises:
about 0.001% by weight amni *visnaga* oil;
about 0.001% by weight of a mixture consisting essentially of *Petasites japonicus* root extract and water;
about 0.001% by weight arginine;
about 0.001% by weight bentofiamine;
about 0.1% by weight of a mixture consisting essentially of butylene glycol, cetyl hydroxyethylcellulose, rutin, palmitoyl tripeptide-1, palmitoyl tetrapeptide-7, *Phaseolus lunatus* seed extract, and water;
about 0.125% by weight of a component selected from the group consisting of *cannabis* oil, cannabidiol, Δ9-tetrahydrocannabinol, cannabinol, cannabigerol, cannabidiolic acid, tetrahydrocannabinolic acid, cannabigerolic acid, and cannabichromene;
about 0.001% by weight *Capsicum frutescens* fruit extract;
about 1% by weight of a mixture consisting essentially of *chondrus* corpus extract and sodium hyaluronate;
about 0.5% by weight *Citrus paradisi* oil;
about 0.1% by weight *Corynanthe yohimbe* extract;
about 0.1% by weight of a mixture consisting essentially of glycerin, water, butylene glycol, carbomer, polysorbate 20, palmitoyl oligopeptide, and palmitoyl tetrapeptide-7;
about 0.1% by weight glycolic acid;
about 0.1% by weight *Glycyrrhiza glabra* root extract;
about 0.2% by weight of a mixture consisting essentially of *Helianthis annuus* seed oil and *Rosmarinus officianalis* leaf extract;
about 0.001% by weight hexapeptide 30;
about 0.001% by weight hexapeptide 8;
about 1% by weight of *Laminaria japonica* extract;
about 0.001% by weight *Melaluca alternifolia* leaf oil;
about 0.1% by weight *Mentha piperita* leaf oil;
about 0.5% by weight of a mixture consisting essentially of menthol and menthyl lactate;
about 0.001% by weight *Oenothera biennis* oil;
about 0.125% by weight *Persea gratissima* oil;
about 0.5% by weight of a mixture consisting essentially of *Physalis angulata* extract and capyrylic/capric triglycerides;
about 0.1% by weight *Pinus pinaster* bark extract;
about 0.001% by weight *Salix alba* bark extract;
about 1% by weight *Simmondsia chinensis* seed oil;
about 0.1% by weight *Tanacetum parthenium*;
about 0.1% by weight tocopherol;
about 1% by weight urea;
about 0.1% by weight *Valerian officinalis* extract;
about 0.3% by weight of a mixture consisting essentially of water, butylene glycol, dextran, and palmitoyl tripeptide-9;
about 0.25% by weight xanthan gum; and
water.

In an embodiment, the balance of the mixture comprises at least one component selected from the group consisting of:
about 0.001% by weight amni *visnaga* oil;
about 0.001% by weight of a mixture consisting essentially of *Petasites japonicus* root extract and water;
about 0.001% by weight arginine;
about 0.001% by weight bentofiamine;
about 0.1% by weight of a mixture consisting essentially of butylene glycol, cetyl hydroxyethylcellulose, rutin, palmitoyl tripeptide-1, palmitoyl tetrapeptide-7, *Phaseolus lunatus* seed extract, and water;
about 0.125% by weight of a component selected from the group consisting of *cannabis* oil, cannabidiol, Δ9-tetrahydrocannabinol, cannabinol, cannabigerol, cannabidiolic acid, tetrahydrocannabinolic acid, cannabigerolic acid, and cannabichromene;
about 0.001% by weight *Capsicum frutescens* fruit extract;
about 1% by weight of a mixture consisting essentially of *chondrus* corpus extract and sodium hyaluronate;
about 0.4% by weight *Citrus paradisi* oil;
about 0.1% by weight of a mixture consisting essentially of glycerin, water, butylene glycol, carbomer, polysorbate 20, palmitoyl oligopeptide, and palmitoyl tetrapeptide-7;
about 0.1% by weight glycolic acid;
about 0.1% by weight *Glycyrrhiza glabra* root extract;
about 0.2% by weight of a mixture consisting essentially of *Helianthis annuus* seed oil and *Rosmarinus officianalis* leaf extract;
about 0.001% by weight hexapeptide 30;
about 0.001% by weight hexapeptide 8;
about 1% by weight of *Laminaria japonica* extract;
about 0.001% by weight *Melaluca alternifolia* leaf oil;
about 0.1% by weight *Mentha piperita* leaf oil;
about 0.5% by weight of a mixture consisting essentially of menthol and menthyl lactate;
about 0.001% by weight *Oenothera biennis* oil;
about 0.125% by weight *Persea gratissima* oil;
about 0.5% by weight of a mixture consisting essentially of *Physalis angulata* extract and capyrylic/capric triglycerides;
about 0.1% by weight *Pinus pinaster* bark extract;
about 0.001% by weight *Salix alba* bark extract;
about 1% by weight *Simmondsia chinensis* seed oil;
about 0.1% by weight *Tanacetum parthenium*;
about 0.1% by weight tocopherol;
about 1% by weight urea;
about 0.1% by weight *Valerian officinalis* extract;
about 0.3% by weight of a mixture consisting essentially of water, butylene glycol, dextran, and palmitoyl tripeptide-9;
about 0.25% by weight xanthan gum; and
water.

In an embodiment, the balance of the mixture comprises:
about 0.001% by weight amni *visnaga* oil;
about 0.001% by weight of a mixture consisting essentially of *Petasites japonicus* root extract and water;
about 0.001% by weight arginine;
about 0.001% by weight bentofiamine;
about 0.1% by weight of a mixture consisting essentially of butylene glycol, cetyl hydroxyethylcellulose, rutin, palmitoyl tripeptide-1, palmitoyl tetrapeptide-7, *Phaseolus lunatus* seed extract, and water;

about 0.125% by weight of a component selected from the group consisting of *cannabis* oil, cannabidiol, Δ9-tetrahydrocannabinol, cannabinol, cannabigerol, cannabidiolic acid, tetrahydrocannabinolic acid, cannabigerolic acid, and cannabichromene;

about 0.001% by weight *Capsicum frutescens* fruit extract;

about 1% by weight of a mixture consisting essentially of *chondrus corpus* extract and sodium hyaluronate;

about 0.4% by weight *Citrus paradisi* oil;

about 0.1% by weight of a mixture consisting essentially of glycerin, water, butylene glycol, carbomer, polysorbate 20, palmitoyl oligopeptide, and palmitoyl tetrapeptide-7;

about 0.1% by weight glycolic acid;

about 0.1% by weight *Glycyrrhiza glabra* root extract;

about 0.2% by weight of a mixture consisting essentially of *Helianthis annuus* seed oil and *Rosmarinus officianalis* leaf extract;

about 0.001% by weight hexapeptide 30;

about 0.001% by weight hexapeptide 8;

about 1% by weight of *Laminaria japonica* extract;

about 0.001% by weight *Melaluca alternifolia* leaf oil;

about 0.1% by weight *Mentha piperita* leaf oil;

about 0.5% by weight of a mixture consisting essentially of menthol and menthyl lactate;

about 0.001% by weight *Oenothera biennis* oil;

about 0.125% by weight *Persea gratissima* oil;

about 0.5% by weight of a mixture consisting essentially of *Physalis angulata* extract and capyrylic/capric triglycerides;

about 0.1% by weight *Pinus pinaster* bark extract;

about 0.001% by weight *Salix alba* bark extract;

about 1% by weight *Simmondsia chinensis* seed oil;

about 0.1% by weight *Tanacetum parthenium;* about 0.1% by weight tocopherol;

about 1% by weight urea;

about 0.1% by weight *Valerian officinalis* extract;

about 0.3% by weight of a mixture consisting essentially of water, butylene glycol, dextran, and palmitoyl tripeptide-9;

about 0.25% by weight xanthan gum; and water.

In an embodiment, the balance of the mixture comprises at least one component selected from the group consisting of:

about 0.001% by weight amni *visnaga* oil;

about 0.001% by weight of a mixture consisting essentially of *Petasites japonicus* root extract and water;

about 0.001% by weight arginine;

about 0.001% by weight bentofiamine;

about 0.1% by weight of a mixture consisting essentially of butylene glycol, cetyl hydroxyethylcellulose, rutin, palmitoyl tripeptide-1, palmitoyl tetrapeptide-7, *Phaseolus lunatus* seed extract, and water;

about 0.125% by weight of a component selected from the group consisting of *cannabis* oil, cannabidiol, Δ9-tetrahydrocannabinol, cannabinol, cannabigerol, cannabidiolic acid, tetrahydrocannabinolic acid, cannabigerolic acid, and cannabichromene;

about 0.001% by weight *Capsicum frutescens* fruit extract;

about 1% by weight of a mixture consisting essentially of *chondrus corpus* extract and sodium hyaluronate;

about 0.4% by weight *Citrus paradisi* oil;

about 0.1% by weight of a mixture consisting essentially of glycerin, water, butylene glycol, carbomer, polysorbate 20, palmitoyl oligopeptide, and palmitoyl tetrapeptide-7;

about 0.1% by weight glycolic acid;

about 0.2% by weight of a mixture consisting essentially of *Helianthis annuus* seed oil and *Rosmarinus officianalis* leaf extract;

about 0.001% by weight hexapeptide 30;

about 0.001% by weight hexapeptide 8;

about 1% by weight of *Laminaria japonica* extract;

about 0.001% by weight *Melaluca alternifolia* leaf oil;

about 0.1% by weight *Mentha piperita* leaf oil;

about 0.5% by weight of a mixture consisting essentially of menthol and menthyl lactate;

about 0.001% by weight *Oenothera biennis* oil;

about 0.125% by weight *Persea gratissima* oil;

about 0.5% by weight of a mixture consisting essentially of *Physalis angulata* extract and capyrylic/capric triglycerides;

about 0.1% by weight *Pinus pinaster* bark extract;

about 0.001% by weight *Salix alba* bark extract;

about 1% by weight *Simmondsia chinensis* seed oil;

about 0.1% by weight *Tanacetum parthenium;* about 0.1% by weight tocopherol;

about 1% by weight urea;

about 0.3% by weight of a mixture consisting essentially of water, butylene glycol, dextran, and palmitoyl tripeptide-9;

about 0.25% by weight xanthan gum; and water.

In an embodiment, the balance of the mixture comprises:

about 0.001% by weight amni *visnaga* oil;

about 0.001% by weight of a mixture consisting essentially of *Petasites japonicus* root extract and water;

about 0.001% by weight arginine;

about 0.001% by weight bentofiamine;

about 0.1% by weight of a mixture consisting essentially of butylene glycol, cetyl hydroxyethylcellulose, rutin, palmitoyl tripeptide-1, palmitoyl tetrapeptide-7, *Phaseolus lunatus* seed extract, and water;

about 0.125% by weight of a component selected from the group consisting of *cannabis* oil, cannabidiol, Δ9-tetrahydrocannabinol, cannabinol, cannabigerol, cannabidiolic acid, tetrahydrocannabinolic acid, cannabigerolic acid, and cannabichromene;

about 0.001% by weight *Capsicum frutescens* fruit extract;

about 1% by weight of a mixture consisting essentially of *chondrus corpus* extract and sodium hyaluronate;

about 0.4% by weight *Citrus paradisi* oil;

about 0.1% by weight of a mixture consisting essentially of glycerin, water, butylene glycol, carbomer, polysorbate 20, palmitoyl oligopeptide, and palmitoyl tetrapeptide-7;

about 0.1% by weight glycolic acid;

about 0.2% by weight of a mixture consisting essentially of *Helianthis annuus* seed oil and *Rosmarinus officianalis* leaf extract;

about 0.001% by weight hexapeptide 30;

about 0.001% by weight hexapeptide 8;

about 1% by weight of *Laminaria japonica* extract;

about 0.001% by weight *Melaluca alternifolia* leaf oil;

about 0.1% by weight *Mentha piperita* leaf oil;

about 0.5% by weight of a mixture consisting essentially of menthol and menthyl lactate;

about 0.001% by weight *Oenothera biennis* oil;
about 0.125% by weight *Persea gratissima* oil;
about 0.5% by weight of a mixture consisting essentially of *Physalis angulata* extract and capyrylic/capric triglycerides;
about 0.1% by weight *Pinus pinaster* bark extract;
about 0.001% by weight *Salix alba* bark extract;
about 1% by weight *Simmondsia chinensis* seed oil;
about 0.1% by weight *Tanacetum parthenium;*
about 0.1% by weight tocopherol;
about 1% by weight urea;
about 0.3% by weight of a mixture consisting essentially of water, butylene glycol, dextran, and palmitoyl tripeptide-9;
about 0.25% by weight xanthan gum; and
water.

In an embodiment, the balance of the mixture comprises at least one component selected from the group consisting of:
about 0.001% by weight amni *visnaga* oil;
about 0.001% by weight of a mixture consisting essentially of *Petasites japonicus* root extract and water;
about 0.001% by weight arginine;
about 0.001% by weight bentofiamine;
about 0.1% by weight of a mixture consisting essentially of butylene glycol, cetyl hydroxyethylcellulose, rutin, palmitoyl tripeptide-1, palmitoyl tetrapeptide-7, *Phaseolus lunatus* seed extract, and water;
about 0.125% by weight of a component selected from the group consisting of *cannabis* oil, cannabidiol, Δ9-tetrahydrocannabinol, cannabinol, cannabigerol, cannabidiolic acid, tetrahydrocannabinolic acid, cannabigerolic acid, and cannabichromene;
about 0.001% by weight *Capsicum frutescens* fruit extract;
about 1% by weight of a mixture consisting essentially of *chondrus* corpus extract and sodium hyaluronate;
about 0.1% by weight *Cimicifuga racemosa* root extract;
about 0.4% by weight *Citrus paradisi* oil;
about 0.1% by weight *Corynanthe yohimbe* extract;
about 0.1% by weight *Euphausia superba* oil;
about 0.1% by weight of a mixture consisting essentially of glycerin, water, butylene glycol, carbomer, polysorbate 20, palmitoyl oligopeptide, and palmitoyl tetrapeptide-7;
about 0.1% by weight glycolic acid;
about 0.1% by weight *Glycyrrhiza glabra* root extract;
about 0.2% by weight of a mixture consisting essentially of *Helianthis annuus* seed oil and *Rosmarinus officianalis* leaf extract;
about 0.001% by weight hexapeptide 30;
about 0.001% by weight hexapeptide 8;
about 1% by weight of *Laminaria japonica* extract;
about 0.1% by weight *Mentha piperita* leaf oil;
about 0.001% by weight *Oenothera biennis* oil;
about 0.125% by weight *Persea gratissima* oil;
about 0.5% by weight of a mixture consisting essentially of *Physalis angulata* extract and capyrylic/capric triglycerides;
about 0.1% by weight *Pinus pinaster* bark extract;
about 0.001% by weight *Salix alba* bark extract;
about 1% by weight *Simmondsia chinensis* seed oil;
about 0.1% by weight *Tanacetum parthenium;*
about 0.1% by weight tocopherol;
about 1% by weight urea;
about 0.3% by weight of a mixture consisting essentially of water, butylene glycol, dextran, and palmitoyl tripeptide-9;
about 0.25% by weight xanthan gum; and
water.

In an embodiment, the balance of the mixture comprises:
about 0.001% by weight amni *visnaga* oil;
about 0.001% by weight of a mixture consisting essentially of *Petasites japonicus* root extract and water;
about 0.001% by weight arginine;
about 0.001% by weight bentofiamine;
about 0.1% by weight of a mixture consisting essentially of butylene glycol, cetyl hydroxyethylcellulose, rutin, palmitoyl tripeptide-1, palmitoyl tetrapeptide-7, *Phaseolus lunatus* seed extract, and water;
about 0.125% by weight of a component selected from the group consisting of *cannabis* oil, cannabidiol, Δ9-tetrahydrocannabinol, cannabinol, cannabigerol, cannabidiolic acid, tetrahydrocannabinolic acid, cannabigerolic acid, and cannabichromene;
about 0.001% by weight *Capsicum frutescens* fruit extract;
about 1% by weight of a mixture consisting essentially of *chondrus* corpus extract and sodium hyaluronate;
about 0.1% by weight *Cimicifuga racemosa* root extract;
about 0.4% by weight *Citrus paradisi* oil;
about 0.1% by weight *Corynanthe yohimbe* extract;
about 0.1% by weight *Euphausia superba* oil;
about 0.1% by weight of a mixture consisting essentially of glycerin, water, butylene glycol, carbomer, polysorbate 20, palmitoyl oligopeptide, and palmitoyl tetrapeptide-7;
about 0.1% by weight glycolic acid;
about 0.1% by weight *Glycyrrhiza glabra* root extract;
about 0.2% by weight of a mixture consisting essentially of *Helianthis annuus* seed oil and *Rosmarinus officianalis* leaf extract;
about 0.001% by weight hexapeptide 30;
about 0.001% by weight hexapeptide 8;
about 1% by weight of *Laminaria japonica* extract;
about 0.1% by weight *Mentha piperita* leaf oil;
about 0.001% by weight *Oenothera biennis* oil;
about 0.125% by weight *Persea gratissima* oil;
about 0.5% by weight of a mixture consisting essentially of *Physalis angulata* extract and capyrylic/capric triglycerides;
about 0.1% by weight *Pinus pinaster* bark extract;
about 0.001% by weight *Salix alba* bark extract;
about 1% by weight *Simmondsia chinensis* seed oil;
about 0.1% by weight *Tanacetum parthenium;*
about 0.1% by weight tocopherol;
about 1% by weight urea;
about 0.3% by weight of a mixture consisting essentially of water, butylene glycol, dextran, and palmitoyl tripeptide-9;
about 0.25% by weight xanthan gum; and
water.

In an embodiment, the composition further comprises a cold glutamate emulsifier. In another embodiment, the composition further comprises an antiseptic agent. In yet another embodiment, the antiseptic agent is Malaleuka oil. In still another embodiment, the composition further comprises a mast cell and/or enzyme inhibitor. In another embodiment, the mast cell and/or enzyme inhibitor is *phaseolus* lunatis rutin palmitoyl-oligopeptide palmitoyltetrapeptide. In yet another embodiment, the composition further comprises an anti-inflammatory agent. In still another embodiment, the anti-inflammatory agent is turmeric.

In an embodiment, the composition forms nanoparticles or nanolipids. Nanoparticle compositions are useful in a variety of contexts. Nanoparticle compositions have proven to be particularly useful and/or effective in the context of medical applications, including administering therapeutic agents to human subjects in need thereof. Nanoparticle compositions have proven to be particularly useful and/or effective in the context of topical administration of therapeutic agents (see, e.g., PCT patent application number PCT US06/46236, filed Dec. 1, 2006, published as WO 08/045, 107 on Apr. 17, 2008, and entitled "BOTULINUM NANOEMULSIONS; in PCT patent application number PCT US07/86018, filed Nov. 30, 2007, published as WO 08/070,538 on Jun. 12, 2008, and entitled "AMPHIPHILIC ENTITY NANOPARTICLES"; and/or in PCT patent application number PCT US09/48972, filed Jun. 26, 2009, published as WO 09/158,687 on Dec. 30, 2009, and entitled "DERMAL DELIVERY"; the contents of all of which are incorporated herein by reference).

Nanoparticle compositions have been described which may be useful and/or effective for topical administration for treatment of such disorders, but there is a need for improved nanoparticle compositions for topical administration for more effective treatment of disorders such as those associated with the skin. Moreover, there is a need for nanoparticle compositions that are useful and/or effective for administration via non-topical routes for treatment of a wide spectrum of disorders.

In another embodiment, the nanolipids are 150 nm to 250 nm in size. In yet another embodiment, the nanolipids are 150 nm in size. In still another embodiment, the nanolipids are 160 nm in size. In another embodiment, the nanolipids are 170 nm in size. In yet another embodiment, the nanolipids are 180 nm in size. In still another embodiment, the nanolipids are 190 nm in size. In another embodiment, the nanolipids are 200 nm in size. In yet another embodiment, the nanolipids are 210 nm in size. In still another embodiment, the nanolipids are 210 nm in size. In another embodiment, the nanolipids are 220 nm in size. In yet another embodiment, the nanolipids are 230 nm in size. In still another embodiment, the nanolipids are 240 nm in size. In another embodiment, the nanolipids are 250 nm in size.

In an embodiment, the composition forms liposomes. Liposomes are used in medicine and cosmetics as intracorporeal or extracorporeal transport system for various active or active substances, especially for the dermal and transdermal application of active substances. The liposomes are spherical vesicles formed by lipids, lead whose hydrophilic and hydrophobic properties to form a double layer and thereby enclose a water-containing cavity which can be used for transportation purposes. The construction and the preparation of various types of unilamellar and multilamellar liposomes is known and described in many publications.

Liposomes were initially used as models for studying biological membranes. However, in the last 15 years liposomal delivery systems have been designed as advanced delivery vehicles of drugs and other benefits agents into biological tissues. See, e.g., Gregoriadis, G., ed. 1988. Liposomes as Drug Carriers, New York: John Wiley, pp. 3-18).

Traditionally, the thin-film method was used to manufacture liposomes. In this method, the bilayer-forming elements are mixed with a volatile organic solvent (such as chloroform, ether, ethanol, or a combination of these) in a mixing vessel (such as a round bottom flask). The predominant bilayer-forming element used to form conventional phospholipid vesicles is usually a neutral phospholipid such as phosphatidylcholine. Cholesterol is also often included to provide greater stability of the liposome in biological fluids. A charged species such as phosphatidylserine may also be added to prevent aggregation, and other elements such as natural acidic lipids and antioxidants, may also be included.

The lipid-solvent solution is then placed under specified surrounding conditions (e.g., pressure and temperature) such that the volatile solvent is removed by evaporation (e.g., using a rotary evaporator) resulting in the formation of a dry lipid film. This film is then hydrated with aqueous medium containing dissolved solutes, including buffers, salts, and hydrophilic compounds, that are to be entrapped in the lipid vesicles. The hydration steps used influence the type of liposomes formed (e.g., the number of bilayers formed, vesicle size, and entrapment volume). If desirable, non-encapsulated drug or active can be removed from the mixture by a variety of techniques such as centrifugation, dialysis or diafiltration and recovered.

A liposome is a vesicle having at least one lipid bilayer surrounding an inner liquid phase (e.g., either a lipid bilayer surrounding either a liquid core or a liquid phase dispersed between it and another lipid bilayers). Because of this entrapping ability, liposomes are useful as drug delivery systems. Liposomes may have various structures such as multilamellar (MLVs), unilamellar (LUVs or SUVs), and paucilamellar (PLVs). The resulting structure of the liposome is dependent, in part, on the choice of materials forming the hydrophobic phase and the manufacturing parameters such temperature and incubation times.

An amphiphilic bilayer-forming substance is a lipid that is comprised of both a hydrophilic and lipophilic group and is capable of forming, either alone or in combination with other lipids, the bilayer of a liposome. The lipid can have single or multiple lipophilic side chains being either saturated or unsaturated in nature and branched or linear in structure. The amphiphilic bilayer-forming agent can be phospholipid or a ceramide.

In an embodiment, the liposomes are 150 nm to 800 nm in size. In another embodiment, the liposomes are 150 nm in size. In still another embodiment, the liposomes are 160 nm in size. In another embodiment, the liposomes are 170 nm in size. In yet another embodiment, the liposomes are 180 nm in size. In still another embodiment, the liposomes are 190 nm in size. In another embodiment, the liposomes are 200 nm in size. In yet another embodiment, the liposomes are 210 nm in size. In still another embodiment, the liposomes are 210 nm in size. In another embodiment, the liposomes are 220 nm in size. In yet another embodiment, the liposomes are 230 nm in size. In still another embodiment, the liposomes are 240 nm in size. In another embodiment, the liposomes are 250 nm in size.

In yet another embodiment, the liposomes are 300 nm in size. In still another embodiment, the liposomes are 350 nm in size. In another embodiment, the liposomes are 400 nm in size. In yet another embodiment, the liposomes are 450 nm in size. In still another embodiment, the liposomes are 500 nm in size. In another embodiment, the liposomes are 550 nm in size. In yet another embodiment, the liposomes are 600 nm in size. In still another embodiment, the liposomes are 650 nm in size. In another embodiment, the liposomes are 700 nm in size. In yet another embodiment, the liposomes are 750 nm in size.

The form of the topical formulations of the present disclosure is not particularly limited, provided that it is in a form that promotes its use as a topical formulation. Non-limiting examples of the form include a lotion, a cream, a salve, a liniment, an ointment, a gel, a paste, a tonic, an unguent, a nasal spray, a soap, a shampoo, and a lip balm.

In some embodiments of the present disclosure, the same drug ingredient can be formulated into a lotion, cream and ointment. Creams are the most convenient of the three but are inappropriate for application to regions of hairy skin such as the scalp, while a lotion is less viscous and may be readily applied to these areas (many medicated shampoos are in fact lotions). Non-comedogenic lotions are recommended for use on acne prone skin.

In some embodiments of the present disclosure, formulations containing *Cannabis* derived botanical drug product include preparations where all or part of the oil component is hemp oil. These preparations may also comprise any of the other *Cannabis* derived botanical drug products to provide benefit inherent to these materials, such as antibiotics; antiseptics; antifungals; corticosteroids; anti-acne agents; and soothing, smoothing, moisturizing or protective agents.

In some embodiments, the topical formulations can be in the form of a soap, which are formulations that comprise a salt of a fatty acid. Soaps are mainly used as surfactants for washing, bathing, and cleaning, but they are also used in textile spinning and are important components of lubricants. Soaps for cleansing are usually obtained by treating vegetable or animal oils and fats with a strongly alkaline solution. Fats and oils are composed of triglycerides; three molecules of fatty acids are attached to a single molecule of glycerol. The alkaline solution, which is often called lye (although the term "lye soap" refers almost exclusively to soaps made with sodium hydroxide), is believed to promote a chemical reaction known as saponification. In saponification, the fats are first hydrolyzed into free fatty acids, which then combine with the alkali to form crude soap. Glycerol (glycerin) is usually liberated and is either left in or washed out and recovered as a useful byproduct, depending on the process employed.

In some embodiments, the topical formulations can be in the form of a shampoo, which is a hair care product used for the removal of oils, dirt, skin particles, dandruff, environmental pollutants and other contaminant particles that gradually build up in hair. In an embodiment, making a shampoo comprises combining a surfactant, most often sodium lauryl sulfate and/or sodium laureth sulfate with a co-surfactant, most often cocamidopropyl betaine, in an aqueous phase and mixing the aqueous phase to form a thick, viscous liquid. In another embodiment, methods further comprise adding other ingredients, such as salt (sodium chloride), a preservative, and fragrance, to the aqueous phase.

In an embodiment, making a cream comprises (i) dispersing lake/powder into mineral oil or silicone oil to obtain an oil phase; (ii) dispersing an emulsifier, a thickener; and a stabilizer into water in a separate vessel to obtain an aqueous phase; (iii) blending the oil phase and the aqueous phase to form an emulsion; and (iv) dispersing an active ingredient such as a *Cannabis* derived botanical drug product into at least one of the oil phase, the aqueous phase, and the emulsion. In some embodiments, the method further comprises heating during at least one of (i) dispersing lake/powder into mineral oil or silicone oil to obtain an oil phase and (ii) dispersing an emulsifier, a thickener; and a stabilizer into water in a separate vessel to obtain an aqueous phase. Temperatures of this heating are not particularly limited, so long as the oil phase and the aqueous phase result from the dispersing.

In an embodiment, making the topical formulation in the form of a lotion comprises mixing an oil phase comprising hemp oil with an emulsifier and with an aqueous phase to form a mixture and heating said mixture at a temperature of from 45 and 85° C. to form an aqueous emulsion. Emulsifiers include, but are not limited to, cetyl alcohol, stearic acid, and a mixture thereof. The water phase comprises a stabilizing agent such as VEEGUM® or CARBOPOL®.

In an embodiment, a method of treating a dermatological disease comprises applying a therapeutically effective amount of the topical formulation according to the present disclosure to skin affected with a dermatological disease. Non-limiting examples of targeted dermatological diseases include eczema, psoriasis, sunburn, contact dermatitis, poison ivy and conditions caused by other plant materials containing urushiol or related molecules, type 1 and type 2 herpes, insect bites, anal itching, vaginal itching, acne, warts and other acute and chronic dermatoses afflicting humans, and use as a topical analgesic for muscle and arthritic pain.

Cosmetic formulations including lotions, creams, soaps, shampoos, lip balms are that are designed for moisturizing, anti-aging, anti-wrinkle, acne treatment, rough skin treatment, and dandruff. Cosmetic formulations can be administered by any method known in the art.

In an embodiment, the composition is formulated for administration using a cosmetic sprayer. In another embodiment, the sprayer delivers 0.14 to 13 mL of the composition. In yet another embodiment, the composition is formulated for administration in a sunscreen. In still another embodiment, the sunscreen is SPF 30. In another embodiment, the composition is formulated for administration in a T-shirt. In yet another embodiment, the composition is formulated for administration in an elastic bandage. In still another embodiment, the composition is formulated for administration in a wrist band. In another embodiment, the composition is formulated for administration in a headband. In yet another embodiment, the composition is formulated for administration in a brace. In still another embodiment, the brace is a tennis elbow brace. In another embodiment, the composition is formulated for administration in a glove.

Methods of Treatment

In an aspect, also provided herein are methods for treating premenstrual syndrome (PMS) in a subject in need thereof, comprising administering to the subject a therapeutically effective amount of the compositions disclosed herein.

The term premenstrual syndrome, or PMS, is generally used to describe a group of physical and mental symptoms which occur cyclically beginning about seven to fourteen days prior to menses. Menstruation occurs in women from the age of about twelve to thirteen to, on average, until about forty seven years of age. It occurs at more or less regular intervals except during pregnancy and lactation. The normal menstrual cycle averages about twenty-eight days with some variation based upon the woman's genetic makeup, age, physical and emotional well being, as well as other factors. The duration of menstrual flow is variable but usually is between three and seven days. The symptoms of PMS are often so severe and widespread that the American Psychiatric Association has formally identified the diagnostic criteria for PMS in Diagnostic and Statistical Manual of Mental Disorders.

The specific etiology of PMS remains unknown, although many theories have been proposed. These theories include, but are not limited to: hormonal imbalances, hormonal deficiencies, vitamin deficiencies, disturbances of autonomic nervous system, salt and water imbalances, altered endogenous opiates such as endorphins and psychosomatic dysfunction, just to name a few. PMS is likely multifactorial and probably involves changes in neurohormones and neurotransmitters, which are difficult to observe, document and isolate in vivo. See, M. Ferin, R. Jewelewicz and M. Warren, The Menstrual Cycle: Physiology, Reproductive Disorders and Infertility, pp. 198-204 (1993).

Symptoms of PMS are varied and can range from mild to incapacitating. As many as seventy to ninety percent of all women have recurrent premenstrual syndrome, and as many as twenty to forty percent of these women suffer some degree of temporary physical and/or mental incapacitation. Some examples of mental symptoms a woman suffering from PMS may exhibit include difficulty in concentration, fatigue, change in appetite, irritability and depression. Some examples of physical symptoms a woman suffering from PMS may exhibit are increase or decrease in sleep, joint pain, cramps, bloating, edema, acne, constipation and breast tenderness.

The physical, neurological and psychological symptoms of premenstrual syndrome are a major cause of suffering and discomfort to women, and cause substantial loss of time and efficiency in the workplace and can be a major disruption in a women's personal life.

In an embodiment, the subject has a reduction in one or more symptoms of PMS. In another embodiment, the subject has a reduction in fatigue, change in appetite, irritability, difficulty in concentration, depression, changes in sleep, agitation, anxiety, tension, restlessness, moodiness, headaches, joint pain, cramps, bloating, edema, acne, constipation, nausea, inflammation, and/or breast tenderness.

In another aspect, provided herein are methods for treating neuropathy in a subject in need thereof, comprising administering to the subject a therapeutically effective amount of the compositions disclosed herein.

In an embodiment, the neuoropathy is peripheral neuropathy. In an embodiment, the neuoropathy is proximal neuropathy. In an embodiment, the neuoropathy is cranial neuropathy. In an embodiment, the neuoropathy is optic neuropathy. In an embodiment, the neuoropathy is auditory neuropathy. In an embodiment, the neuoropathy is autonomic neuropathy. In an embodiment, the neuoropathy is focal neuropathy.

Neuropathies can include any disease or condition involving neurons and/or supporting cells, such as for example, glia, muscle cells, fibroblasts, etc., and, in particular, those diseases or conditions involving axonal damage. Axonal damage can be caused by traumatic injury or by non-mechanical injury due to diseases or conditions and the result of such damage can be degeneration or dysfunction of the axon and loss of functional neuronal activity. Disease and conditions producing or associated with such axonal damage are among a large number of neuropathic diseases and conditions. Such neuropathies can include peripheral neuropathies, central neuropathies, and combinations thereof. Furthermore, peripheral neuropathic manifestations can be produced by diseases focused primarily in the central nervous systems and central nervous system manifestations can be produced by essentially peripheral or systemic diseases.

Peripheral neuropathies involve damage to the peripheral nerves and such can be caused by diseases of the nerves or as the result of systemic illnesses. Some such diseases can include diabetes, uremia, infectious diseases such as AIDs or leprosy, nutritional deficiencies, vascular or collagen disorders such as atherosclerosis, and autoimmune diseases such as systemic lupus erythematosus, scleroderma, sarcoidosis, rheumatoid arthritis, and polyarteritis *nodosa*. Peripheral nerve degeneration can also result from traumatic, i.e mechanical damage to nerves as well as chemical or thermal damage to nerves. Such conditions that injure peripheral nerves include compression or entrapment injuries such as glaucoma, carpal tunnel syndrome, direct trauma, penetrating injuries, contusions, fracture or dislocated bones; pressure involving superficial nerves (ulna, radial, or peroneal) which can result from prolonged use of crutches or staying in one position for too long, or from a tumor; intraneural hemorrhage; ischemia; exposure to cold or radiation or certain medicines or toxic substances such as herbicides or pesticides. In particular, the nerve damage can result from chemical injury due to a cytotoxic anticancer agent such as, for example, a *vinca* alkaloid such as vincristine. Typical symptoms of such peripheral neuropathies include weakness, numbness, paresthesia (abnormal sensations such as burning, tickling, pricking or tingling) and pain in the arms, hands, legs and/or feet. The neuropathy can also be associated with mitochondrial dysfunction. Such neuropathies can exhibit decreased energy levels, i.e. decreased levels of NAD and ATP.

The peripheral neuropathy can also be a metabolic and endocrine neuropathy which includes a wide spectrum of peripheral nerve disorders associated with systemic diseases of metabolic origin. These diseases, some of which are mentioned earlier, include diabetes mellitus, hypoglycemia, uremia, hypothyroidism, hepatic failure, polycythemia, amyloidosis, acromegaly, *porphyria*, disorders of lipid/glycolipid metabolism, nutritional/vitamin deficiencies, and mitochondrial disorders, among others. The common hallmark of these diseases is involvement of peripheral nerves by alteration of the structure or function of myelin and axons due to metabolic pathway dysregulation.

Neuropathies also include optic neuropathies such as glaucoma; retinal ganglion degeneration such as those associated with retinitis pigmentosa and outer retinal neuropathies; optic nerve neuritis and/or degeneration including that associated with multiple sclerosis; traumatic injury to the optic nerve which can include, for example, injury during tumor removal; hereditary optic neuropathies such as Kjer's disease and Leber's hereditary optic neuropathy; ischemic optic neuropathies, such as those secondary to giant cell arteritis; metabolic optic neuropathies such as neurodegenerative diseases including Leber's neuropathy mentioned earlier, nutritional deficiencies such as deficiencies in vitamins B12 or folic acid, and toxicities such as due to ethambutol or cyanide; neuropathies caused by adverse drug reactions and neuropathies caused by vitamin deficiency. Ischemic optic neuropathies also include non-arteritic anterior ischemic optic neuropathy.

Neurodegenerative diseases that are associated with neuropathy or axonopathy in the central nervous system include a variety of diseases. Such diseases include those involving progressive dementia such as, for example, Alzheimer's disease, senile dementia, Pick's disease, and Huntington's disease; central nervous system diseases affecting muscle function such as, for example, Parkinson's disease, motor neuron diseases and progressive ataxias such as amyotrophic lateral sclerosis; demyelinating diseases such as, for example multiple sclerosis; viral encephalitides such as, for example, those caused by enteroviruses, arboviruses, and herpes simplex virus; and prion diseases. Mechanical injuries such as glaucoma or traumatic injuries to the head and spine can also cause nerve injury and degeneration in the brain and spinal cord. In addition, ischemia and stroke as well as conditions such as nutritional deficiency and chemical toxicity such as with chemotherapeutic agents can cause central nervous system neuropathies.

In an embodiment, the neuropathy is nerve pain. In another embodiment, the subject has a reduction in one or more symptoms of neuropathy. In yet another embodiment, the subject has a reduction in pain, tingling, numbness, burning, and/or loss of sensation.

In yet another aspect, provided herein are methods for treating arthritis in a subject in need thereof, comprising administering to the subject a therapeutically effective amount of the compositions disclosed herein.

Bone loss, or alteration in bone turnover, can result from, or be associated with, many types of arthritis, including rheumatoid arthritis and osteoarthritis. Rheumatoid arthritis is a chronic, systemic and articular inflammatory disorder characterized by weakening of the joint capsules and ligaments, followed by destruction of cartilage, ligaments, tendon and bone, and a decrease in viscosity and other alterations in the synovial membrane and fluid. Rheumatoid arthritis symptoms include systemic weakness, fatigue, localized pain, and stiffness, weakness, swelling, and deformation of the joints of the body.

The pathogenesis of rheumatoid arthritis, leading to the destruction of the joints, is characterized by two phases: 1) an exudative phase involving the microcirculation of the synovial cells that allow an influx of plasma proteins and cellular elements into the joint and 2) a chronic inflammatory phase occurring in the sub-synovium and sub-chondral bone, characterized by pannus (granulation tissue) formation in the joint space, bone erosion, and cartilage destruction. The pannus may form adhesions and scar tissue which causes the joint deformities characteristic of rheumatoid arthritis.

The etiology of rheumatoid arthritis remains obscure. Infectious agents such as bacteria and viruses have been implicated. A current hypothesis is that the Epstein-Barr (EBV) virus is a causative agent for rheumatoid arthritis.

Current rheumatoid arthritis treatment consists predominantly of symptomatic relief by administration of non-steroidal anti-inflammatory drugs (NSAIDs). NSAID treatment is mainly effective in the early stages of rheumatoid arthritis; it is unlikely it will produce suppression of joint inflammation if the disease is present for more than one year. Gold, methotrexate, immunosuppressants and corticosteroids have been tried with limited success.

Osteoarthritis is an inherently non-inflammatory disorder of the movable joints characterized by deterioration and abrasion of articular cartilage, as well as by formation of new bone at the joint periphery. As osteoarthritis progresses, the surface of the articular cartilage is disrupted and wear-particles gain access to the synovial fluid which in turn stimulates phagocytosis by macrophage cells. Thus, an inflammatory response is eventually induced in osteoarthritis. Common clinical symptoms of osteoarthritis include cartilaginous and bony enlargements of the finger joints and stiffness on awakening and painful movement.

Common symptomatic treatments for osteoarthritis include analgesics, anti-inflammatories, disease-modifying arthritic drugs ("DMARDs"), steroids, and physical therapy.

In an embodiment, the arthritis is osteoarthritis, rheumatoid arthritis, psoriatic arthritis, or gout. In another embodiment, the subject has a reduction in one or more symptoms of arthritis. In yet another embodiment, the subject has a reduction in pain, swelling, stiffness, and/or an improvement in range of motion.

In still another aspect, provided herein are methods for treating pain in a subject in need thereof, comprising administering to the subject a therapeutically effective amount of the compositions disclosed herein. In an embodiment, the composition blocks afferent neuro synaptic pain signals.

In another aspect, provided herein are methods for improving skin quality in a subject in need thereof, comprising administering to the subject a therapeutically effective amount of the compositions disclosed herein. In an embodiment, the subject has an improvement in one or more aspects of skin quality. In another embodiment, the subject has a reduction in wrinkles, younger looking skin, improved cellular turnover, improved skin radiance, improvement in acne, brightened skin, improved skin hydration, and/or improved skin physiology.

In yet another aspect, provided herein are methods for treating skin discomfort in a subject in need thereof, comprising administering to the subject a therapeutically effective amount of the compositions disclosed herein. In an embodiment, the subject has a reduction in one or more symptoms of skin discomfort. In another embodiment, the subject has a reduction in itching and/or topical discomfort. In yet another embodiment, the itching and/or topical discomfort are from tattooing, laser treatment, or mild abrasions.

In still another aspect, provided herein are methods method for treating sprains, strains, muscle distress, and ligament distress in a subject in need thereof, comprising administering to the subject a therapeutically effective amount of the compositions disclosed herein.

In another aspect, provided herein are methods for treating anxiety in a subject in need thereof, comprising administering to the subject a therapeutically effective amount of the compositions disclosed herein.

In yet another aspect, provided herein are methods for inducing wound repair in a subject in need thereof, comprising administering to the subject a therapeutically effective amount of the compositions disclosed herein.

In still another aspect, provided herein are methods for treating headache in a subject in need thereof, comprising administering to the subject a therapeutically effective amount of the compositions disclosed herein.

In another aspect, provided herein are methods for treating hangover in a subject in need thereof, comprising administering to the subject a therapeutically effective amount of the compositions disclosed herein.

In yet another aspect, provided herein are methods for treating sinus pain in a subject in need thereof, comprising administering to the subject a therapeutically effective amount of the compositions disclosed herein.

In still another aspect, provided herein are methods for treating athlete's foot fungus in a subject in need thereof, comprising administering to the subject a therapeutically effective amount of the compositions disclosed herein.

In another aspect, provided herein are methods for treating sunburn in a subject in need thereof, comprising administering to the subject a therapeutically effective amount of the compositions disclosed herein.

In yet another aspect, provided herein are methods for treating insect bites in a subject in need thereof, comprising administering to the subject a therapeutically effective amount of the compositions disclosed herein.

In still another aspect, provided herein are methods for lightening the skin, comprising administering to the subject a therapeutically effective amount of the compositions disclosed herein.

In an embodiment, subject is human. In another embodiment, the composition is applied in as a cream. In yet another embodiment, the cream is a massage cream for relief of deep muscle pain. In still another embodiment, the composition is applied as a spray. In another embodiment, the composition is applied topically. In yet another embodiment, the skin is heated to 14° F. using microcirculation. In still another embodiment, the subject experiences non-standard vasodilation of micro vessels. In another embodiment, the composition works with natural body biochemistry.

EXAMPLES

Example 1: Major Vehicle Phases and General Procedure for Preparation

Phase 1—Aqueous Phase

This is the base aqueous phase that consists of purified water (32-442%) plus an appropriate preservative. The inventive compositions use 1-2% Lincoserve CG-9 (proprietary blend of capryl glycol and ethylhexyl glycerin sold by Lincoln Fine Ingredients of Lincoln, R.I.). It will be understood that any pharmaceutically appropriate preservative such as substituted ureas, EDTA, or phenoxyethanol or mixtures of acceptable preservatives can be used.

Phase 2—Polyhydroxy Solvents

Polyhydroxy solvents such as glycerol are important for emulsion and liposome formation. The present disclosure uses 4-12% of an equi-weight combination of glycerol and propanediol. The ratio between these two solvents can be varied. A quantity (0.1-0.5%) of a polysaccharide gum (such as xanthan gum) can be included to facilitate emulsification and control viscosity. Other appropriate bacterial or plant polysaccharide gums can be used. The gum can be readily transferred to one of the other phases.

Phase 3—Major Hydrophobic Components

This phase comprises about 17-27% of the product and contains the major waxes and oils of the vehicle. It will be understood that a wide range of hydrophobic components can be used to make an acceptable vehicle particularly by adjusting the content and amount of the other phases. The selected components produce a cream with optimal characteristics. A number of botanical extracts having particularly beneficial characteristics are used to this end. Important fats/oils used include jojoba (*Simmondsia chinensis*) seed oil (0.5-2.5%), virgin olive (*Olea europaea*) oil (1-5%), caprylic/capric triglycerides (1-3%) such as the Endimate 33V ingredient blend available from CoastSouthwest of Placentia, Calif., isopropyl palmitate lecithin blend (1-3%) such as SVVT-7-L available from LucasMyer Cosmetics of Champlan, France, glycol stearate, glyceryl stearate, caprylic/capric triglycerides cosmetic blend (3-8%; this cosmetic blend includes sodium acrylate/sodium acryloyl dimethyl taurate copolymer as a dispersant/emulsifier. If this blend is not used as a source of triglycerides, it may be necessary to include this or other emulsifiers in the phase) such as Jeesperse ICE-T-LB-NS available from Jeen International Corporation of Fairfield, N.J., ethoxydiglycol (1-3%) and dimethicone (3-8%). In addition, mixed tocopherols (0.1-0.3%) are included as a preservative/antioxidant. A number of botanical oil/extracts may be added; particularly preferred are rosemary (*Rosmarinus officinalis*) leaf extract (0.1-0.3%) such as Rosamax available from Global Ingredient Solutions of Irvine, Calif. and *Physalis* angulate extract (0.3-0.8%) such as Physave available from Chemyunion of Sorocaba, Brazil. As a viscosity control agent and to enhance skin penetration, the preferred formulation may also include dimethyl isosorbide (2-7%). This component is logically included in Phase 3 although alternatively it can be included in Phase 5, or even one of the other phases without compromising its effectiveness.

Phase 4—Primary Emulsifier

The disclosed formulations use ethoxylated sorbitan monolaurate (polysorbate 20) (1-5%) as a primary emulsifier. It will be understood that other sorbitan fatty acids (such as monostearate, monolaurate or monopalmitate) and sorbitans having various length of polyethoxyethylene chains (polysorbate 20 usually has a chain length of 20) can be used depending on the exact proportions of other components in the composition. Also, other well-known nonionic cosmetic emulsifiers may also be functional in the disclosed formulations; however, natural polysorbate 20 obtainable from Croda, Inc. of Chino Hills, Calif. is preferred in the current formulation.

Phase 5—Hydrophilic Active Ingredients

This phase comprises 6-10% of the final product and includes water soluble active ingredients that enhance the pain-relieving properties of the final mixture. Many of these ingredients are natural botanical extracts or derived from such extracts. This phase also includes emulsifying and dispersing components that could be included in one of the other phases but are included in Phase 5 to improve the mixing character of this phase prior to mixing this phase into the other phases. These components include polyethylene glycol (PEG)-8/PEG-8 SMDI (saturated methylenediphenyldiisocyanate) copolymer with palmitoyl myristyl senate (1-3%) such as Ceramide A2 PH obtainable from Croda, Inc. of Chino Hills, Calif.; Fucogel 1, 5 P (biosaccharide gum) available from Solabia Group USA, Inc. of New York, N.Y.; and butylene glycol and palmitoyl tripeptide-8 (0.1-0.5%) such as Neutrazen obtainable from Lucas Meyers Cosmetics of Champlan, France. Important botanical extracts include *Laminaria japonica* extract (0.5-1.5%) such as FSS Phytocoll Marine PF obtainable from Formulator's Sample Shop of Lincolnton, N.C.; *Pinus pinaster* bark extract (pycnogenol) (0.005-0.015%) obtainable from SK Bioland of Chungnam, South Korea; *Chondrus crispa* extract and sodium hyaluronate (0.5-1.5%) such as Marmoist obtainable from Biocogent LLC of Stony Brook, N.Y.; *Glycyrrhiza glabra* (licorice) root extract (0.005-0.15%); *Salix alba* bark extract obtainable from Formulator's Sample Shop of Lincolnton, N.C.; *Valerian officinalis* extract (0.05%-0.15%); *Tanacetum parthenium* (feverfew) extract (0.05-0.15%); and *Coryanthe yohimbe* extract (0.05-0.15%). It will be appreciated that the various botanical extracts are used in relatively small amounts. Ranges known to be effective are given, but using significantly greater amounts of one or more of the botanical extracts are likely to give equivalent or acceptable results. Those of ordinary skill in the art will understand that the main limitations are altering the physical properties of the final product and needlessly increasing the cost of the product. This array of botanical extracts has proven effective in general pain relief preparations. It has been found that a preparation intended for relief of premenstrual pain is improved by the addition of *Cimicifuga racemosa* (black cohosh) root extract (0.05-0.15%).

Phase 6—Liposome Generating Ingredients (10-20%)

Phase 6 is conveniently compounded as three sub-phases (Phase 6.1, Phase 6.2 and Phase 6.3). There is no requirement to formulate the ingredients in exactly this manner. The liposomes are generated when lecithin (or other appropriate phospholipds) are reacted/dissolved in an appropriate hydrophilic solvent such as glycerin and/or propanediol and this mixture is homogenized with a water phase. The water phase becomes entrapped by the liposomal membranes. Optionally, active botanical extracts such as those from Phase 5 can be incorporated into the aqueous phase so that they also become trapped. In the current disclosure a significant pain relief component is oil from *Cannabis sativa*. This oil can be obtained by extracting *cannabis* flowers—including hemp—in which case it contains anti-inflammatory cannabidiol (CBD) and depending on the source may also include other cannabinoids that effectively relieve pain. If the *cannabis* oil is extracted from *cannabis* seeds, it will have beneficial skin hydrating properties instead.

Phase 6.1 (3-7%) contains a mixture of propanediol and lecithin such as Pro-Lipo-Neo obtainable from Lucas Meyers Cosmetics. Phase 6.2 (0.1-0.5%) contains a mixture of *cannabis* oil and *Persea americana* (avocado) oil such as IntegriLIPID refined avocado oil obtainable from Integrity Ingredients Corp. of Torrance, Calif. The avocado oil is a carrier oil to control viscosity of the phase; it can be omitted, replaced by a different carrier oil and/or the proportions between the *cannabis* oil and carrier oil can be varied. Phase 6.3 (5-15%) is the liposome aqueous phase consisting of purified water or purified water plus active botanical extracts.

Phase 7—Fragrance (0.1-0.6%)

The fragrance phase is optional in that the effectiveness of the product is not appreciably altered by the omission of fragrance. In the current formulation essential oils are used to create fragrance. It will be appreciated that different essential oils or other fragrance agents can be selected without altering the effectiveness of the final product. In addition, the fragrance oils are added here as a separate phase. Essentially identical results are achieved by including the fragrance agents in one or more of the other phases such Phases 2, 3 or 5. Phase 7 consists of *citrus* (grapefruit) oil (0.3-0.5%) and *Mentha piperita* (peppermint) oil (0.005-0.015%). Compounding the Final Product from the Phases.

Two different processes go on during the compounding process. When the main phases (Phases 1, 2, 4 and 5) are mixed in the proper manner the hydrophobic components (mostly in Phase 5) are emulsified and dispersed by the ingredients in Phases 2 and 4 to form an oil in water emulsion known as a lotion or cream depending on the final viscosity. When the Phase 6 sub-phases are properly mixed liposomes are formed that enclose the Phase 6.3 aqueous phase (including any hydrophilic agents (e.g., botanical extracts) added thereto. The *cannabis* oil (Phase 6.2) is variously enclosed within the liposomes and dissolved into the liposomal membranes. The liposomes are mixed into the lotion or cream formed by the other phases so that the liposomes remain suspended in the water phase of the emulsion.

The normal order of mixing the various phases is as follows. It is possible to deviate from this order without compromising the final product. First, the major aqueous phase plus preservative (Phase 1) are placed in a mixing tank and stirred thoroughly to dissolve and mix the preservative throughout the water phase. The components of Phase 2 are placed in a separate vessel and mixed thoroughly until uniform. Phase 2 is then added to the mixing tank containing Phase 1 and mixed thoroughly until uniform. The Phase 3 ingredients are placed in a separate vessel and are pre-mixed and heated to 30-35° C. until the mixture is uniform. The mixture is allowed to cool to 25-30° C. and is then added to the main mixing tank (already containing Phases 1 and 2) and mixed thoroughly to ensure uniformity. Phase 4 is then added to the main mixing tank and mixed thoroughly. At this point the hydrophobic components emulsify to form a lotion of cream. Phase 5 is then mixed in to add the active hydrophilic components.

In a separate mixing vessel, Phase 6.1 components are mixed until uniform. In yet another mixing vessel, the components of Phase 6.2 are mixed until uniform. Phase 6.2 is then added to phase 6.1 and mixed until homogeneous. Finally, Phase 6.3 is slowly added to the combined Phases 6.1 and 6.2 and mixed until homogenous (usually 30 min or more). At this point the liposomes are completely generated so that the combined Phases 6.1, 6.2 and 6.3 are added to the main mixing tank and mixed into the emulsion until uniform. Then, the fragrance (Phase 7) is added to the main mixing tank and thoroughly mixed in. As already pointed out, Phase 7 could already have been incorporated into one of the other phases.

Example 2: Example Pain Relief Cream Formulation

|         | COMPONENT | % W/W |
|---------|-----------|-------|
| PHASE 1 | Water/Aqua | 39.640 |
|         | Caprlyl Glycol (and) Ethylhexylglycerin | 1.200 |
| PHASE 2 | Glycerin | 4.000 |
|         | Xanthan Gum | 0.250 |
|         | Propanediol | 4.000 |
| PHASE 3 | Sodium Acrylate/Sodium Acryloyl Dimethyl Taurate Copolymer, Cetyl Alcohol, Glycol Stearate, Glyceryl Stearate, Caprylic/Capric Triglyceride | 5.000 |
|         | Caprylic/Capric Triglycerides | 2.000 |
|         | Olea Europaea (Olive) Fruit Oil | 2.000 |
|         | Dimethicone | 5.000 |
|         | Tocopherol | 0.100 |
|         | *Helianthus Annuus* Seed Oil (and) *Rosmarinus Officinalis* (Rosemary) Leaf Extract | 0.200 |
|         | Dimethyl Isosorbide | 2.000 |
|         | Ethoxydiglycol | 2.000 |
|         | *Physalis Angulata* Extract (and) Caprylic/Capric Triglyceride | 0.500 |
|         | Isopropyl Palmitate (and) Lecithin (and) Water (and) *Swertia Chirata* Extract | 2.000 |
|         | *Simmondsia Chinensis* (Jojoba) Seed Oil | 1.000 |
|         | Menthyl (and) Menthyl Lactate | 0.500 |
|         | *Oenothera Biennis* (Evening Primrose) Oil | 0.001 |

| COMPONENT | % W/W |
|---|---|
| PHASE 4    Polysorbate 20 (Naturally Derived) | 2.000 |
| PHASE 5    Aqua (and) Glycerin (and) PEG-8 (and) PEG-8/SMDI Copolymer (and) Palmitoyl myristyl serinate (and) Sodium polyacrylate | 2.000 |
| Biosaccharide Gum-1 | 3.000 |
| Glycol Acid | 0.100 |
| Glycerin (and) Water (Aqua) (and) Butylene Glycol (and) Carbomer (and) Polysorbate 20 (and) Palmitoyl Oligopeptide (and) Palmitoyl Tetrapeptide-7 | 0.100 |
| *Laminaria Japonica* Extract | 1.000 |
| *Chondrus Crispus* Extract (and) Sodium Hyaluronate | 1.000 |
| *Pinus Pinaster* Bark Extract | 0.100 |
| Water (and) Butylene Glycol (and) Dextran (and) Palmitoyl Tripeptide-8 | 0.300 |
| Butylene Glycol (and) Aqua (and) Cetyl Hydroxyethylcellulose (and) Rutin (and) Palmitoyl Tripeptide-1 (and) Palmitoyl Tetrapeptide-7 (and) *Phaseolus Lunatus* (Green Bean) Seed Extract | 0.100 |
| *Glycyrrhiza Glabra* (Licorice) Root Extract | 0.100 |
| Urea | 1.000 |
| *Salix Alba* Bark Extract | 0.001 |
| Aqua (and) *Petasites Japonicus* Root Extract | 0.001 |
| *Valerian Officinalis* Extract | 0.100 |
| *Tanacetum Parthenium* (Feverfew) Extract | 0.100 |
| *Corynanthe Yohimbe* Extract | 0.100 |
| Arginine | 0.001 |
| Amni Visnaga Oil | 0.001 |
| Bentofiamine | 0.001 |
| Hexapeptide 8 | 0.001 |
| Hexapeptide 30 | 0.001 |
| *Capsicum Frutescens* Fruit Extract | 0.001 |
| PHASE 6.1    Propanediol (and) Lecithin | 5.000 |
| PHASE 6.2    *Cannabis Sativa* Seed Oil | 0.125 |
| *Persea Gratissima* (Avocado) Oil | 0.125 |
| PHASE 6.3    Water/Aqua | 11.650 |
| PHASE 7    *Citrus Paradisi* (Pink Grapefruit) Oil | 0.500 |
| *Mentha Piperita* (Peppermint) Leaf Oil | 0.100 |
| *Melaluca Alternifolia* (Tea Tree) Leaf Oil | 0.001 |

Example 3: Example Arthritis Cream Formulation

| COMPONENT | % W/W |
|---|---|
| PHASE 1    Water/Aqua | 39.840 |
| Caprlyl Glycol (and) Ethylhexylglycerin | 1.200 |
| PHASE 2    Glycerin | 4.000 |
| Xanthan Gum | 0.250 |
| Propanediol | 4.000 |
| PHASE 3    Sodium Acrylate/Sodium Acryloyl Dimethyl Taurate Copolymer, Cetyl Alcohol, Glycol Stearate, Glyceryl Stearate, Caprylic/Capric Triglyceride | 5.000 |
| Caprylic/Capric Triglycerides | 2.000 |
| *Olea Europaea* (Olive) Fruit Oil | 2.000 |
| Dimethicone | 5.000 |
| Tocopherol | 0.100 |
| *Helianthus Annuus* Seed Oil (and) *Rosmarinus Officinalis* (Rosemary) Leaf Extract | 0.200 |
| Dimethyl Isosorbide | 2.000 |
| Ethoxydiglycol | 2.000 |
| *Physalis Angulata* Extract (and) Caprylic/Capric Triglyceride | 0.500 |
| Isopropyl Palmitate (1) Lecithin (2) Water (3) *Swertia Chirata* Extract(4) | 2.000 |
| *Simmondsia Chinensis* (Jojoba) Seed Oil | 1.000 |
| Menthol (and) Menthyl Lactate | 0.500 |
| *Oenothera Biennis* (Evening Primrose) Oil | 0.001 |
| PHASE 4    Polysorbate 20 (Naturally Derived) | 2.000 |
| PHASE 5    Aqua (and) Glycerin (and) PEG-8 (and) PEG-8/SMDI Copolymer (and) Palmitoyl myristyl serinate (and) Sodium polyacrylate | 2.000 |
| Biosaccharide Gum-1 | 3.000 |
| Glycol Acid | 0.100 |
| Glycerin (and) Water (Aqua) (and) Butylene Glycol (and) Carbomer (and) Polysorbate 20 (and) Palmitoyl Oligopeptide (and) Palmitoyl Tetrapeptide-7 | 0.100 |
| *Laminaria Japonica* Extract | 1.000 |
| *Chondrus Crispus* Extract (and) Sodium Hyaluronate | 1.000 |
| *Pinus Pinaster* Bark Extract | 0.100 |

| COMPONENT | % W/W |
|---|---|
| Water (and) Butylene Glycol (and) Dextran (and) Palmitoyl Tripeptide-8 | 0.300 |
| Butylene Glycol (and) Aqua (and) Cetyl Hydroxyethylcellulose (and) Rutin (and) Palmitoyl Tripeptide-1 (and) Palmitoyl Tetrapeptide-7 (and) *Phaseolus Lunatus* (Green Bean) Seed Extract | 0.100 |
| *Glycyrrhiza Glabra* (Licorice) Root Extract | 0.100 |
| Urea | 1.000 |
| *Salix Alba* Bark Extract | 0.001 |
| Aqua (and) *Petasites Japonicus* Root Extract | 0.001 |
| *Valerian Officinalis* Extract | 0.100 |
| *Tanacetum Parthenium* (Feverfew) Extract | 0.100 |
| Arginine | 0.001 |
| Ammi Visnaga Oil | 0.001 |
| Bentofiamine | 0.001 |
| Hexapeptide 8 | 0.001 |
| Hexapeptide 30 | 0.001 |
| *Capsicum Frutescens* Fruit Extract | 0.001 |
| PHASE 6.1 — Propanediol (and) Lecithin | 5.000 |
| PHASE 6.2 — *Cannabis Sativa* Seed Oil | 0.125 |
| *Persea Gratissima* (Avocado) Oil | 0.125 |
| PHASE 6.3 — Water/Aqua | 11.650 |
| PHASE 7 — *Citrus Paradisi* (Pink Grapefruit) Oil | 0.400 |
| *Mentha Piperita* (Peppermint) Leaf Oil | 0.100 |
| *Melaleuca Alternifolia* (Tea Tree) Leaf Oil | 0.001 |

Example 4: Example Neuropathy Cream Formulation

| | COMPONENT | % W/W |
|---|---|---|
| PHASE 1 | Water/Aqua | 40.140 |
| | Caprlyl Glycol (and) Ethylhexylglycerin | 1.200 |
| PHASE 2 | Glycerin | 4.000 |
| | Xanthan Gum | 0.250 |
| | Propanediol | 4.000 |
| PHASE 3 | Sodium Acrylate/Sodium Acryloyl Dimethyl Taurate Copolymer, Cetyl Alcohol, Glycol Stearate, Glyceryl Stearate, Caprylic/Capric Triglyceride | 5.000 |
| | Caprylic/Capric Triglycerides | 2.000 |
| | *Olea Europaea* (Olive) Fruit Oil | 2.000 |
| | Dimethicone | 5.000 |
| | Tocopherol | 0.100 |
| | *Helianthus Annuus* Seed Oil (and) *Rosmarinus Officinalis* (Rosemary) Leaf Extract | 0.200 |
| | Dimethyl Isosorbide | 2.000 |
| | Ethoxydiglycol | 2.000 |
| | *Physalis Angulata* Extract (and) Caprylic/Capric Triglyceride | 0.500 |
| | Isopropyl Palmitate (and) Lecithin (and) Water (and) *Swertia Chirata* Extract | 2.000 |
| | *Simmondsia Chinensis* (Jojoba) Seed Oil | 1.000 |
| | Menthol (and) Menthyl Lactate | 0.500 |
| | *Oenothera Biennis* (Evening Primrose) Oil | 0.001 |
| PHASE 4 | Polysorbate 20 (Naturally Derived) | 2.000 |
| PHASE 5 | Aqua (and) Glycerin (and) PEG-8 (and) PEG-8/SMDI Copolymer (and) Palmitoyl myristyl serinate (and) Sodium polyacrylate | 2.000 |
| | Biosaccharide Gum-1 | 3.000 |
| | Glycolic Acid | 0.100 |
| | Glycerin (and) Water (Aqua) (and) Butylene Glycol (and) Carbomer (and) Polysorbate 20 (and) Palmitoyl Oligopeptide (and) Palmitoyl Tetrapeptide-7 | 0.100 |
| | *Laminaria Japonica* Extract | 1.000 |
| | *Chondrus Crispus* Extract (and) Sodium Hyaluronate | 1.000 |
| | *Pinus Pinaster* Bark Extract | 0.100 |
| | Water (and) Butylene Glycol (and) Dextran (and) Palmitoyl Tripeptide-8 | 0.300 |
| | Butylene Glycol (and) Aqua (and) Cetyl Hydroxyethylcellulose (and) Rutin (and) Palmitoyl Tripeptide-1 (and) Palmitoyl Tetrapeptide-7 (and) *Phaseolus Lunatus* (Green Bean) Seed Extract | 0.100 |
| | Urea | 1.000 |
| | *Salix Alba* Bark Extract | 0.001 |
| | Aqua (and) *Petasites Japonicus* Root Extract | 0.001 |
| | Arginine | 0.001 |
| | Ammi Visnaga Oil | 0.001 |
| | Bentofiamine | 0.001 |

| | COMPONENT | % W/W |
|---|---|---|
| | Hexapeptide-8 | 0.001 |
| | Hexapeptide-30 | 0.001 |
| | *Capsicum Frutescens* Fruit Extract | 0.001 |
| PHASE 6.1 | Propanediol (and) Lecithin | 5.000 |
| PHASE 6.2 | *Cannabis Sativa* Seed Oil | 0.125 |
| | *Persea Gratissima* (Avocado) Oil | 0.125 |
| PHASE 6.3 | Water/Aqua | 11.650 |
| PHASE 7 | *Citrus Paradisi* (Pink Grapefruit) Oil | 0.400 |
| | *Mentha Piperita* (Peppermint) Leaf Oil | 0.100 |
| | *Melaleuca Alternifolia* (Tea Tree) Leaf Oil | 0.001 |

Example 5: Example PMS Cream Formulation

| | COMPONENT | % W/W |
|---|---|---|
| PHASE 1 | Water/Aqua | 36.041 |
| | Caprlyl Glycol (and) Ethylhexylglycerin | 1.200 |
| PHASE 2 | Glycerin | 4.000 |
| | Xanthan Gum | 0.250 |
| | Propanediol | 4.000 |
| PHASE 3 | Sodium Acrylate/Sodium Acryloyl Dimethyl Taurate Copolymer, Cetyl Alcohol, Glycol Stearate, Glyceryl Stearate, Caprylic/Capric Triglyceride | 5.000 |
| | Caprylic/Capric Triglycerides | 2.000 |
| | *Olea Europaea* (Olive) Fruit Oil | 2.000 |
| | Dimethicone | 5.000 |
| | Tocopherol | 0.100 |
| | *Helianthus Annuus* Seed Oil (and) *Rosmarinus Officinalis* (Rosemary) Leaf Extract | 0.200 |
| | Dimethyl Isosorbide | 2.000 |
| | Ethoxydiglycol | 2.000 |
| | *Physalis Angulata* Extract (and) Caprylic/Capric Triglyceride | 0.500 |
| | Isopropyl Palmitate (and) Lecithin (and) Water (and) *Swertia Chirata* Extract | 2.000 |
| | *Simmondsia Chinensis* (Jojoba) Seed Oil | 1.000 |
| | *Oenothera Biennis* (Evening Primrose) Oil | 0.001 |
| PHASE 4 | Polysorbate 20 (Naturally Derived) | 2.000 |
| PHASE 5 | Aqua (and) Glycerin (and) PEG-8 (and) PEG-8/SMDI Copolymer (and) Palmitoyl myristyl serinate (and) Sodium polyacrylate | 2.000 |
| | Biosaccharide Gum-1 | 3.000 |
| | Glycol Acid | 0.100 |
| | Glycerin (and) Water (Aqua) (and) Butylene Glycol (and) Carbomer (and) Polysorbate 20 (and) Palmitoyl Oligopeptide (and) Palmitoyl Tetrapeptide-7 | 0.100 |
| | *Laminaria Japonica* Extract | 1.000 |
| | *Chondrus Crispus* Extract (and) Sodium Hyaluronate | 1.000 |
| | *Pinus Pinaster* Bark Extract | 0.100 |
| | Water (and) Butylene Glycol (and) Dextran (and) Palmitoyl Tripeptide-8 | 0.300 |
| | Butylene Glycol (and) Aqua (and) Cetyl Hydroxyethylcellulose (and) Rutin (and) Palmitoyl Tripeptide-1 (and) Palmitoyl Tetrapeptide-7 (and) *Phaseolus Lunatus* (Green Bean) Seed Extract | 0.100 |
| | *Glycyrrhiza Glabra* (Licorice) Root Extract | 0.100 |
| | Urea | 1.000 |
| | *Salix Alba* Bark Extract | 0.001 |
| | Aqua (and) *Petasites Japonicus* Root Extract | 0.001 |
| | *Valerian Officinalis* Extract | 0.100 |
| | *Tanacetum Parthenium* (Feverfew) Extract | 0.100 |
| | *Corynanthe Yohimbe* Extract | 0.100 |
| | *Euphausia Superba* (Krill) Oil | 0.100 |
| | *Cimicifuga Racemosa* (Black Cohosh) Root Extract | 0.100 |
| | Arginine | 0.001 |
| | Amni Visnaga Oil | 0.001 |
| | Bentofiamine | 0.001 |
| | Hexapeptide 8 | 0.001 |
| | Hexapeptide 30 | 0.001 |
| | *Capsicum Frutescens* Fruit Extract | 0.001 |
| PHASE 6.1 | Propanediol (and) Lecithin | 5.000 |
| PHASE 6.2 | *Cannabis Sativa* Seed Oil | 0.125 |
| | *Persea Gratissima* (Avocado) Oil | 0.125 |
| PHASE 6.3 | Water/Aqua | 11.650 |
| PHASE 7 | *Citrus Paradisi* (Pink Grapefruit) Oil | 0.400 |
| | *Mentha Piperita* (Peppermint) Leaf Oil | 0.100 |

Example 6: Treatment of Pain, Arthritis, and Neuropathy

A human subject suffering from chronic pain, arthritis, and neuropathy used the creams for pain relief, arthritis relief, and neuropathy relief described in Examples 2, 3, and 4, respectively. The human subject experienced complete relief from symptoms within in 5 minutes of administration.

Example 7: Treatment of PMS

A human subject with severe PMS symptoms, including cramping and moodiness, used the PMS relief cream described in Example 5. She experienced immediate relief from her symptoms. In addition, she felt better overall and slept better than she does when not using the cream.

Example 8: Treatment of Migraines

A human subject with migraines treated their symptoms with prescription medication that caused them to feel "out of it" for a day or two after taking the medication. The human subject used the pain relief cream described in Example 2 and had relief from the migraine pain within 10 minutes. The pain relief lasted for a long time and allowed the human subject to sleep better.

Example 9: Treatment of Plantar Fasciitis Pain

A human subject suffering from severe pain associated with plantar fasciitis was unable to find any products that would relieve their pain. The pain was so severe that the human subject believed that that their foot might be broken and went to their doctor to have X-rays taken. However, the treatment options provided by their doctor did not alleviate the pain. The human subject used the pain relief cream described in Example 2 and within minutes experienced a reduction in pain. After three weeks of continued use, the human subject remains pain-free.

Example 10: Treatment of Chronic Neck and Joint Pain

A human subject had chronic neck and joint pain that had lasted for more than 10 years. They had been treating their symptoms with NSAIDs, but had been experiencing negative side effects from prolonged use. The human subject used the pain relief cream described in Example 2 and experienced relief from their pain. The human subject said that the product had changed their life.

A second human subject had knee pain that prevented them from walking or standing for an extended period of time. They applied the pain relief cream described in Example 2 and experienced results within minutes. Treatment with the product allowed them to walk without any pain.

Example 11: Treatment of Back Pain

A human subject used the pain relief cream described in Example 2 to treat their back pain. They suffered from lower back pain and could not find any products that would help. Within two hours of applying the cream, the human subject felt the pain subsiding. The human subject was free from pain later that day.

The disclosed subject matter is not to be limited in scope by the specific embodiments and examples described herein. Indeed, various modifications of the disclosure in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes. Other embodiments are within the following claims.

The invention claimed is:

1. A topical composition, the composition comprising:
   propanediol;
   dimethicone;
   glycerin;
   caprylic/capric triglycerides;
   *Olea europaea* fruit oil;
   biosaccharide gum-1;
   dimethyl isosorbide;
   ethoxydiglycol;
   polysorbate 20;
   a mixture consisting essentially of sodium acrylate/sodium acryloyl dimethyl taurate copolymer, cetyl alcohol, glycol stearate, and caprylic/capric triglycerides;
   a mixture consisting essentially of isopropyl palmitate, lecithin, water, and *Swertia chirata* extract;
   a mixture consisting essentially of propanediol and lecithin;
   a mixture consisting essentially of capryl glycol and ethylhexylglycerin;
   a mixture consisting essentially of water, glycerin, PEG-8, PEG-8/SMDI copolymer, palmitoyl myristyl serinate, and polyacrylate; and
   the balance of the composition comprises one or more components selected from the group consisting of cannabidiol, Δ9-tetrahydrocannabinol, cannabinol, cannabigerol, cannabidiolic acid, tetrahydrocannabinolic acid, cannabigerolic acid, cannabichromene, water, amni *visnaga* oil, *Petasites japonicus* root extract, arginine, bentofiamine, butylene glycol, cetyl hydroxyethylcellulose, rutin, palmitoyl tripeptide-1, palmitoyl tetrapeptide-7, *Phaseolus lunatus* seed extract, *cannabis* oil, *Capsicum frutescens* fruit extract, *chondrus* corpus extract, sodium hyaluronate, *Citrus paradisi* oil, *Corynanthe yohimbe* extract, butylene glycol, glycerin, carbomer, polysorbate 20, palmitoyl oligopeptide, glycolic acid, *Glycyrrhiza glabra* root extract, *Helianthis annuus* seed oil, *Rosmarinus officianalis* leaf extract, hexapeptide 30, hexapeptide 8, *Laminaria japonica* extract, *Melaluca alternifolia* leaf oil, *Mentha piperita* leaf oil, menthol, menthyl lactate, *Oenothera biennis* oil, *Persea gratissima* oil, *Physalis angulata* extract, capyrylic/capric triglycerides, *Pinus pinaster* bark extract, *Salix alba* bark extract, *Simmondsia chinensis* seed oil, *Tanacetum parthenium*, tocopherol, urea, *Valerian officinalis* extract, dextran, palmitoyl tripeptide-8, xanthan gum, *Euphausia superba* oil, and cimisifuga racemosa root extract.

2. The composition of claim 1, wherein the composition comprises:
   about 4% by weight propanediol;
   about 5% by weight dimethicone;
   about 4% by weight glycerin;
   about 2% by weight caprylic/capric triglycerides;

about 2% by weight *Olea europaea* fruit oil;
about 3% by weight biosaccharide gum-1;
about 2% by weight dimethyl isosorbide;
about 2% by weight ethoxydiglycol;
about 2% by weight polysorbate 20;
about 5% by weight of a mixture consisting essentially of sodium acrylate/sodium acryloyl dimethyl taurate copolymer, cetyl alcohol, glycol stearate, and caprylic/capric triglycerides;
about 2% by weight of a mixture consisting essentially of isopropyl palmitate, lecithin, water, and *Swertia chirata* extract;
about 5% by weight of a mixture consisting essentially of propanediol and lecithin;
about 1.2% by weight of a mixture consisting essentially of capryl glycol and ethylhexylglycerin;
about 2% by weight of a mixture consisting essentially of water, glycerin, PEG-8, PEG-8/SMDI copolymer, palmitoyl myristyl serinate, and polyacrylate; and
the balance of the composition comprises one or more components selected from the group consisting of cannabidiol, Δ9-tetrahydrocannabinol, cannabinol, cannabigerol, cannabidiolic acid, tetrahydrocannabinolic acid, cannabigerolic acid, cannabichromene, water, amni *visnaga* oil, *Petasites japonicus* root extract, arginine, bentofiamine, butylene glycol, cetyl hydroxyethylcellulose, rutin, palmitoyl tripeptide-1, palmitoyl tetrapeptide-7, *Phaseolus lunatus* seed extract, *cannabis* oil, *Capsicum frutescens* fruit extract, *chondrus corpus* extract, sodium hyaluronate, *Citrus paradisi* oil, *Corynanthe yohimbe* extract, butylene glycol, glycerin, carbomer, polysorbate 20, palmitoyl oligopeptide, glycolic acid, *Glycyrrhiza glabra* root extract, *Helianthis annuus* seed oil, *Rosmarinus officinalis* leaf extract, hexapeptide 30, hexapeptide 8, *Laminaria japonica* extract, *Melaluca alternifolia* leaf oil, *Mentha piperita* leaf oil, menthol, menthyl lactate, *Oenothera biennis* oil, *Persea gratissima* oil, *Physalis angulata* extract, capyrylic/capric triglycerides, *Pinus pinaster* bark extract, *Salix alba* bark extract, *Simmondsia chinensis* seed oil, *Tanacetum parthenium*, tocopherol, urea, *Valerian officinalis* extract, dextran, palmitoyl tripeptide-8, xanthan gum, *Euphausia superba* oil, and *cimisifuga racemosa* root extract.

3. The composition of claim 1, wherein the *cannabis* oil comprises from about 0.001% to about 10% by weight cannabidiol, or from about 0.001% to about 25% by weight Δ9-tetrahydrocannabinol.

4. The composition of claim 1, wherein the balance of the mixture comprises:
about 0.001% by weight amni *visnaga* oil;
about 0.001% by weight of a mixture consisting essentially of *Petasites japonicus* root extract and water;
about 0.001% by weight arginine;
about 0.001% by weight bentofiamine;
about 0.1% by weight of a mixture consisting essentially of butylene glycol, cetyl hydroxyethylcellulose, rutin, palmitoyl tripeptide-1, palmitoyl tetrapeptide-7, *Phaseolus lunatus* seed extract, and water;
about 0.125% by weight of a component selected from the group consisting of *cannabis* oil, cannabidiol, Δ9-tetrahydrocannabinol, cannabinol, cannabigerol, cannabidiolic acid, tetrahydrocannabinolic acid, cannabigerolic acid, and cannabichromene;
about 0.001% by weight *Capsicum frutescens* fruit extract;
about 1% by weight of a mixture consisting essentially of *chondrus corpus* extract and sodium hyaluronate;
about 0.5% by weight *Citrus paradisi* oil;
about 0.1% by weight *Corynanthe yohimbe* extract;
about 0.1% by weight of a mixture consisting essentially of glycerin, water, butylene glycol, carbomer, polysorbate 20, palmitoyl oligopeptide, and palmitoyl tetrapeptide-7;
about 0.1% by weight glycolic acid;
about 0.1% by weight *Glycyrrhiza glabra* root extract;
about 0.2% by weight of a mixture consisting essentially of *Helianthis annuus* seed oil and *Rosmarinus officinalis* leaf extract;
about 0.001% by weight hexapeptide 30;
about 0.001% by weight hexapeptide 8;
about 1% by weight of *Laminaria japonica* extract;
about 0.001% by weight *Melaluca alternifolia* leaf oil;
about 0.1% by weight *Mentha piperita* leaf oil;
about 0.5% by weight of a mixture consisting essentially of menthol and menthyl lactate;
about 0.001% by weight *Oenothera biennis* oil;
about 0.125% by weight *Persea gratissima* oil;
about 0.5% by weight of a mixture consisting essentially of *Physalis angulata* extract and capyrylic/capric triglycerides;
about 0.1% by weight *Pinus pinaster* bark extract;
about 0.001% by weight *Salix alba* bark extract;
about 1% by weight *Simmondsia chinensis* seed oil;
about 0.1% by weight *Tanacetum parthenium*;
about 0.1% by weight tocopherol;
about 1% by weight urea;
about 0.1% by weight *Valerian officinalis* extract;
about 0.3% by weight of a mixture consisting essentially of water, butylene glycol, dextran, and palmitoyl tripeptide-8;
about 0.25% by weight xanthan gum; and
water.

5. The composition of claim 1, wherein the balance of the mixture comprises:
about 0.001% by weight amni *visnaga* oil;
about 0.001% by weight of a mixture consisting essentially of *Petasites japonicus* root extract and water;
about 0.001% by weight arginine;
about 0.001% by weight bentofiamine;
about 0.1% by weight of a mixture consisting essentially of butylene glycol, cetyl hydroxyethylcellulose, rutin, palmitoyl tripeptide-1, palmitoyl tetrapeptide-7, *Phaseolus lunatus* seed extract, and water;
about 0.125% by weight of a component selected from the group consisting of *cannabis* oil, cannabidiol, Δ9-tetrahydrocannabinol, cannabinol, cannabigerol, cannabidiolic acid, tetrahydrocannabinolic acid, cannabigerolic acid, and cannabichromene;
about 0.001% by weight *Capsicum frutescens* fruit extract;
about 1% by weight of a mixture consisting essentially of *chondrus corpus* extract and sodium hyaluronate;
about 0.4% by weight *Citrus paradisi* oil;
about 0.1% by weight of a mixture consisting essentially of glycerin, water, butylene glycol, carbomer, polysorbate 20, palmitoyl oligopeptide, and palmitoyl tetrapeptide-7;
about 0.1% by weight glycolic acid;
about 0.1% by weight *Glycyrrhiza glabra* root extract;
about 0.2% by weight of a mixture consisting essentially of *Helianthis annuus* seed oil and *Rosmarinus officinalis* leaf extract;

about 0.001% by weight hexapeptide 30;
about 0.001% by weight hexapeptide 8;
about 1% by weight of *Laminaria japonica* extract;
about 0.001% by weight *Melaluca alternifolia* leaf oil;
about 0.1% by weight *Mentha piperita* leaf oil;
about 0.5% by weight of a mixture consisting essentially of menthol and menthyl lactate;
about 0.001% by weight *Oenothera biennis* oil;
about 0.125% by weight *Persea gratissima* oil;
about 0.5% by weight of a mixture consisting essentially of *Physalis angulata* extract and capyrylic/capric triglycerides;
about 0.1% by weight *Pinus pinaster* bark extract;
about 0.001% by weight *Salix alba* bark extract;
about 1% by weight *Simmondsia chinensis* seed oil;
about 0.1% by weight *Tanacetum parthenium;*
about 0.1% by weight tocopherol;
about 1% by weight urea;
about 0.1% by weight *Valerian officinalis* extract;
about 0.3% by weight of a mixture consisting essentially of water, butylene glycol, dextran, and palmitoyl tripeptide-8;
about 0.25% by weight xanthan gum; and
water.

6. The composition of claim 1, wherein the balance of the mixture comprises:
about 0.001% by weight amni *visnaga* oil;
about 0.001% by weight of a mixture consisting essentially of *Petasites japonicus* root extract and water;
about 0.001% by weight arginine;
about 0.001% by weight bentofiamine;
about 0.1% by weight of a mixture consisting essentially of butylene glycol, cetyl hydroxyethylcellulose, rutin, palmitoyl tripeptide-1, palmitoyl tetrapeptide-7, *Phaseolus lunatus* seed extract, and water;
about 0.125% by weight of a component selected from the group consisting of *cannabis* oil, cannabidiol, Δ9-tetrahydrocannabinol, cannabinol, cannabigerol, cannabidiolic acid, tetrahydrocannabinolic acid, cannabigerolic acid, and cannabichromene;
about 0.001% by weight *Capsicum frutescens* fruit extract;
about 1% by weight of a mixture consisting essentially of *chondrus corpus* extract and sodium hyaluronate;
about 0.4% by weight *Citrus paradisi* oil;
about 0.1% by weight of a mixture consisting essentially of glycerin, water, butylene glycol, carbomer, polysorbate 20, palmitoyl oligopeptide, and palmitoyl tetrapeptide-7;
about 0.1% by weight glycolic acid;
about 0.2% by weight of a mixture consisting essentially of *Helianthis annuus* seed oil and *Rosmarinus officianalis* leaf extract;
about 0.001% by weight hexapeptide 30;
about 0.001% by weight hexapeptide 8;
about 1% by weight of *Laminaria japonica* extract;
about 0.001% by weight *Melaluca alternifolia* leaf oil;
about 0.1% by weight *Mentha piperita* leaf oil;
about 0.5% by weight of a mixture consisting essentially of menthol and menthyl lactate;
about 0.001% by weight *Oenothera biennis* oil;
about 0.125% by weight *Persea gratissima* oil;
about 0.5% by weight of a mixture consisting essentially of *Physalis angulata* extract and capyrylic/capric triglycerides;
about 0.1% by weight *Pinus pinaster* bark extract;
about 0.001% by weight *Salix alba* bark extract;
about 1% by weight *Simmondsia chinensis* seed oil;
about 0.1% by weight *Tanacetum parthenium;*
about 0.1% by weight tocopherol;
about 1% by weight urea;
about 0.3% by weight of a mixture consisting essentially of water, butylene glycol, dextran, and palmitoyl tripeptide-8;
about 0.25% by weight xanthan gum; and
water.

7. The composition of claim 1, wherein the balance of the mixture comprises:
about 0.001% by weight amni *visnaga* oil;
about 0.001% by weight of a mixture consisting essentially of *Petasites japonicus* root extract and water;
about 0.001% by weight arginine;
about 0.001% by weight bentofiamine;
about 0.1% by weight of a mixture consisting essentially of butylene glycol, cetyl hydroxyethylcellulose, rutin, palmitoyl tripeptide-1, palmitoyl tetrapeptide-7, *Phaseolus lunatus* seed extract, and water;
about 0.125% by weight of a component selected from the group consisting of *cannabis* oil, cannabidiol, Δ9-tetrahydrocannabinol, cannabinol, cannabigerol, cannabidiolic acid, tetrahydrocannabinolic acid, cannabigerolic acid, and cannabichromene;
about 0.001% by weight *Capsicum frutescens* fruit extract;
about 1% by weight of a mixture consisting essentially of *chondrus corpus* extract and sodium hyaluronate;
about 0.1% by weight *Cimicifuga racemosa* root extract;
about 0.4% by weight *Citrus paradisi* oil;
about 0.1% by weight *Corynanthe yohimbe* extract;
about 0.1% by weight *Euphausia superba* oil;
about 0.1% by weight of a mixture consisting essentially of glycerin, water, butylene glycol, carbomer, polysorbate 20, palmitoyl oligopeptide, and palmitoyl tetrapeptide-7;
about 0.1% by weight glycolic acid;
about 0.1% by weight *Glycyrrhiza glabra* root extract;
about 0.2% by weight of a mixture consisting essentially of *Helianthis annuus* seed oil and *Rosmarinus officianalis* leaf extract;
about 0.001% by weight hexapeptide 30;
about 0.001% by weight hexapeptide 8;
about 1% by weight of *Laminaria japonica* extract;
about 0.1% by weight *Mentha piperita* leaf oil;
about 0.001% by weight *Oenothera biennis* oil;
about 0.125% by weight *Persea gratissima* oil;
about 0.5% by weight of a mixture consisting essentially of *Physalis angulata* extract and capyrylic/capric triglycerides;
about 0.1% by weight *Pinus pinaster* bark extract;
about 0.001% by weight *Salix alba* bark extract;
about 1% by weight *Simmondsia chinensis* seed oil;
about 0.1% by weight *Tanacetum parthenium;*
about 0.1% by weight tocopherol;
about 1% by weight urea;
about 0.3% by weight of a mixture consisting essentially of water, butylene glycol, dextran, and palmitoyl tripeptide-8;
about 0.25% by weight xanthan gum; and
water.

8. The composition of claim 1, wherein the composition forms nanolipids, wherein the nanolipids are 150 nm to 250 nm in size.

9. The composition of claim 1, wherein the composition forms liposomes, wherein the liposomes are optionally 150 nm to 800 nm in size.

\* \* \* \* \*